(12) United States Patent
Rodriguez et al.

(10) Patent No.: US 9,752,145 B2
(45) Date of Patent: Sep. 5, 2017

(54) COMPOSITIONS AND METHODS FOR REDUCING C/EBP HOMOLOGOUS PROTEIN ACTIVITY IN MYELOID-DERIVED SUPPRESSOR CELLS

(71) Applicant: Board of Supervisors of Louisiana State University and Agricultural and Mechanical College, Baton Rouge, LA (US)

(72) Inventors: Paulo Cesar Rodriguez, New Orleans, LA (US); Augusto C. Ochoa, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/125,737

(22) PCT Filed: Mar. 16, 2015

(86) PCT No.: PCT/US2015/020692
§ 371 (c)(1),
(2) Date: Sep. 13, 2016

(87) PCT Pub. No.: WO2015/142713
PCT Pub. Date: Sep. 24, 2015

(65) Prior Publication Data
US 2017/0002351 A1    Jan. 5, 2017

Related U.S. Application Data

(60) Provisional application No. 61/954,072, filed on Mar. 17, 2014.

(51) Int. Cl.
*C12N 15/113*    (2010.01)
*A61K 9/127*    (2006.01)

(52) U.S. Cl.
CPC .......... *C12N 15/113* (2013.01); *A61K 9/1271* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 2003/0157030 A1 | 8/2003 | Davis et al. | |
| 2005/0221432 A1 | 10/2005 | Rycyzyn et al. | |
| 2005/0250127 A1* | 11/2005 | Fisher | C07K 14/54 435/6.14 |
| 2011/0268722 A1* | 11/2011 | Siegelin | A61K 31/40 424/130.1 |
| 2012/0225038 A1 | 9/2012 | Bronte et al. | |
| 2012/0276004 A1 | 11/2012 | Epstein et al. | |
| 2013/0323835 A1* | 12/2013 | Mcdonald | A61K 31/5375 435/375 |

FOREIGN PATENT DOCUMENTS

| | | |
|---|---|---|
| WO | 9616988 A1 | 6/1996 |
| WO | 2007097751 A1 | 8/2007 |
| WO | 2012054747 A2 | 4/2012 |

OTHER PUBLICATIONS

International Search Report for PCT/US2015/020692 mailed Jun. 29, 2015.
Chang, et al., "Vitamin D Suppresses Th17 Cytokine Production by Inducing C/EBP Homologous Protein (CHOP) Expression", J. Biol. Chem. 2010, 285:38751-38755, doi: 10.1074/jbc.C110.185777 originally published online Oct. 25, 2010.
Condamine, et al., "Can the Suppressive Activity of Myeloid-Derived Suppressor Cells Be "Chop" ped?", Immunity Previews, CellPress, Immunity 41, Sep. 18, 2014, pp. 341-342.
Thevenot, et al., "The stress-response sensor chop regulates the function and accumulation of myeloid-derived suppressor cells in tumors", Immunity, Sep. 18, 2014; 41(3): 389-401, doi:10.1016/j.immuni.2014.08.015.
Gabrilovich, D. I., S. Ostrand-Rosenberg, and V. Bronte. 2012. Coordinated regulation of myeloid cells by tumours. Nat. Rev. Immunol. 12: 253-268, pp. 1-32.
Raber, P., A. C. Ochoa, and P. C. Rodriguez. 2012. Metabolism of L-arginine by myeloid-derived suppressor cells in cancer: mechanisms of T cell suppression and therapeutic perspectives. Immunol. Invest 41: 614-634, pp. 1-19.
Gabrilovich, D. I., and S. Nagaraj. 2009. Myeloid-derived suppressor cells as regulators of the immune system. Nat. Rev. Immunol. 9: 162-174, pp. 1-26.
De, S. C., P. Serafini, I. Marigo, L. Dolcetti, M. Bolla, S. P. Del, C. Melani, C. Giuducci, M. P. Colombo, M. Iezzi, P. Musiani, P. Zanovello, and V. Bronte. 2005. Nitroaspirin corrects immune dysfunction in tumor-bearing hosts and promotes tumor eradication by cancer vaccination. Proc. Natl. Acad. Sci. U. S. A 102: 4185-4190.

(Continued)

*Primary Examiner* — Jennifer McDonald
(74) *Attorney, Agent, or Firm* — Thomas | Horstemeyer, LLP

(57) ABSTRACT

Provided are compositions and methods of use thereof that modulate C/EBP homologous stress-related protein (Chop) activity in Myeloid-derived Suppressor Cells (MDSCs). Chop is a key point in the response of MDSCs to tumor-generated stress factors. In turn, the MDSCs release cytokines and other factors that function as immune suppressors, thereby allowing the tumors to thrive and expand. By inhibiting the level of Chop activity, the immunosuppressive function of MDSCs is disrupted. It has also been unexpectedly found that there is a concomitant increase in the ability of MDSCs to act as antigen-presenting and cytokine producing cells so as to act in increasing the efficacy of anti-tumor immune-based therapies.

13 Claims, 27 Drawing Sheets

(56) References Cited

OTHER PUBLICATIONS

Rodriguez, P. C., D. G. Quiceno, J. Zabaleta, B. Ortiz, A. H. Zea, M. B. Piazuelo, A. Delgado, P. Correa, J. Brayer, E. M. Sotomayor, S. Antonia, J. B. Ochoa, and A. C. Ochoa. 2004. Arginase I production in the tumor microenvironment by mature myeloid cells inhibits T-cell receptor expression and antigen-specific T-cell responses. Cancer Res. 64: 5839-5849.
Srivastava, M. K., L. Zhu, M. Harris-White, U. K Kar, M. Huang, M. F. Johnson, J. M. Lee, D. Elashoff, R. Strieter, S. Dubinett, and S. Sharma. 2012. Myeloid suppressor cell depletion augments antitumor activity in lung cancer. PLoS. One. 7: e40677, pp. 1-13.
Marigo, I., E. Bosio, S. Solito, C. Mesa, A. Fernandez, L. Dolcetti, S. Ugel, N. Sonda, S. Bicciato, E. Falisi, F. Calabrese, G. Basso, P. Zanovello, E. Cozzi, S. Mandruzzato, and V. Bronte. 2010. Tumor-induced tolerance and immune suppression depend on the C/EBPbeta transcription factor. Immunity. 32: 790-802.
Bruchard, M., G. Mignot, V. Derangere, F. Chalmin, A. Chevriaux, F. Vegran, W. Boireau, B. Simon, B. Ryffel, J. L. Connat, J. Kanellopoulos, F. Martin, C. Rebe, L. Apetoh, and F. Ghiringhelli. 2013. Chemotherapy-triggered cathepsin B release in myeloid-derived suppressor cells activates the NIrp3 inflammasome and promotes tumor growth. Nat. Med. 19: 57-64.
Diaz-Montero, C. M., M. L. Salem, M. L Nishimura, E. Garrett-Mayer, D. J. Cole, and A. J. Montero. 2009. Increased circulating myeloid-derived suppressor cells correlate with clinical cancer stage, metastatic tumor burden, and doxorubicin-cyclophosphamide chemotherapy. Cancer Immunol. Immunother. 58: 49-59, pp. 1-21.
Harding, H. P., Y. Zhang, H. Zeng, I. Novoa, P. D. Lu, M. Calfon, N. Sadri, C. Yun, B. Popko, R. Paules, D. F. Stojdl, J. C. Bell, T. Hettmann, J. M. Leiden, and D. Ron. 2003. An integrated stress response regulates amino acid metabolism and resistance to oxidative stress. Mol. Cell 11: 619-633.
Rzymski, T., and A. L. Harris. 2007. The unfolded protein response and integrated stress response to anoxia. Clin. Cancer Res. 13: 2537-2540.
Rouschop, K M., B. T. van den, L. Dubois, H. Niessen, J. Bussink, K. Savelkouls, T. Keulers, H. Mujcic, W. Landuyt, J. W. Voncken, P. Lambin, A. J. van der Kogel, M. Koritzinsky, and B. G. Wouters. 2010. The unfolded protein response protects human tumor cells during hypoxia through regulation of the autophagy genes MAP1LC3B and ATG5. J. Clin. Invest 120: 127-141.
Ye, J., M. Kumanova, L. S. Hart, K. Sloane, H. Zhang, D. N. De Panis, E. Bobrovnikova-Marjon, J. A. Diehl, D. Ron, and C. Koumenis. 2010. The GCN2-ATF4 pathway os critical for tumour cell survivak abd prodiferation in response to nutrient deprivation. EMBO J. 29: 2082-2096.
Wang, S., and R. J. Kaufman. 2012. The impact of the unfolded protein response on human disease. J. Cell Biol. 197: 857-867.
Mahadevan, N. R., V. Anufreichik, J. J. Rodvold, K. T. Chiu, H. Sepulveda, and M. Zanetti. 2012. Cell-extrinsic effects of tumor ER stress imprint myeloid dendritic cells and impair CD8(+) T cell priming. PLoS. One. 7: e51845, pp. 1-13.
Mahadevan, N. R., J. Rodvold, H. Sepulveda, S. Rossi, A. F. Drew, and M. Zanetti. 2011. Transmission of endoplasmic reticulum stress and pro-inflammation from tumor cells to myeloid cells. Proc. Natl. Acad. Sci. U. S. A 108: 6561-6566.
Youn, J. I., V. Kumar, M. Collazo, Y. Nefedova, T. Condamine, P. Cheng, A. Villagra, S. Antonia, J. C. McCaffrey, M. Fishman, A. Samaik, P. Homa, E. Sotomayor, and D. I. Gabrilovich. 2013. Epigenetic silencing of retinoblastoma gene regulates pathologic differentiation of myeloid cells in cancer. Nat. Immunol. 14: 211-220 pp. 1-26.
Highfill, S. L., P. C. Rodriguez, Q. Zhou, C. A. Goetz, B. H. Koehn, R. Veenstra, P. A. Taylor, A. Panoskaltsis-Mortari, J. S. Serody, D. H. Munn, J. Tolar, A. C. Ochoa, and B. R. Blazar. 2010. Bone marrow myeloid-derived suppressor cells (MDSCs) inhibit graft-versus-host disease (GVHD) via an arginase-1-dependent mechanism that is up-regulated by interleukin-13. Blood 116: 5738-5747.
Hattori, T., N. Ohoka, H. Hayashi, and K. Onozaki. 2003. C/EBP homologous protein (CHOP) up-regulates IL-6 transcription by trapping negative regulating NF-IL6 isoform. FEBS Lett. 541: 33-39.
Hattori, T., N. Ohoka, Y. Inoue, H. Hayashi, and K. Onozaki. 2003. C/EBP family transcription factors are degraded by the proteasome but stabilized by forming dimer. Oncogene 22: 1273-1280.
Chiribau, C. B., F. Gaccioli, C. C. Huang, C. L. Yuan, and M. Hatzoglou. 2010. Molecular symbiosis of CHOP and C/EBP beta isoform LIP contributes to endoplasmic reticulum stress-induced apoptosis. Mol. Cell Biol. 30: 3722-3731.
Landen, C. N., Jr., A. Chavez-Reyes, C. Bucana, R. Schmandt, M. T. Deavers, G. Lopez-Berestein, and A. K. Sood. 2005. Therapeutic EphA2 gene targeting in vivo using neutral liposomal small interfering RNA delivery. Cancer Res. 65: 6910-6918.
Merritt, W. M., Y. G. Lin, W. A. Spannuth, M. S. Fletcher, A. A. Kamat, L. Y. Han, C. N. Landen, N. Jennings, G. K. De, R. R. Langley, G. Villares, A. Sanguino, S. K. Lutgendorf, G. Lopez-Berestein, M. M. Bar-Eli, and A. K. Sood. 2008. Effect of interleukin-8 gene silencing with liposome-encapsulated small interfering RNA on ovarian cancer cell growth. J. Natl. Cancer Inst. 100: 359-372.
Hernandez, C. P., K. Morrow, L. A. Lopez-Barcons, J. Zabaleta, R. Sierra, C. Velasco, J. Cole, and P. C. Rodriguez. 2010. Pegylated arginase I: a potential therapeutic approach in T-ALL. Blood 115: 5214-5221.
Morrow, K, C. P. Hernandez, P. Raber, V. L. Del, A. M. Wilk, S. Majumdar, D. Wyczechowska, K. Reiss, and P. C. Rodriguez. 2013. Anti-leukemic mechanisms of pegylated arginase I in acute lymphoblastic T-cell leukemia. Leukemia 27: 569-577.
Nagaraj, S., K. Gupta, V. Pisarev, L. Kinarsky, S. Sherman, L. Kang, D. L. Herber, J. Schneck, and D. I. Gabrilovich. 2007. Altered recognition of antigen is a mechanism of CD8+ T cell tolerance in cancer. Nat. Med. 13: 828-835.
Sinha, P., O. Chornoguz, V. K. Clements, K. A. Artemenko, R. A. Zubarev, and S. Ostrand-Rosenberg. 2011. Myeloid-derived suppressor cells express the death receptor Fas and apoptose in response to T cell-expressed FasL. Blood 117: 5381-5390.
Zhao, X., L. Rong, X. Zhao, X. Li, X. Liu, J. Deng, H. Wu, X. Xu, U. Erben, P. Wu, U. Syrbe, J. Sieper, and Z. Qin. 2012. TNF signaling drives myeloid-derived suppressor cell accumulation. J. Clin. Invest 122: 4094-4104.
Mukherjee, D., K. H. Kaestner, K. K. Kovalovich, and L. E. Greenbaum. 2001. Fas-induced apoptosis in mouse hepatocytes is dependent on C/EBPbeta. Hepatology 33: 1166-1172.
Li, J., M. Ni, B. Lee, E. Barron, D. R. Hinton, and A. S. Lee. 2008. The unfolded protein response regulator GRP78/BiP is required for endoplasmic reticulum integrity and stress-induced autophagy in mammalian cells. Cell Death. Differ. 15: 1460-1471.
Li, J. B Lee, and A. S. Lee. 2006. Endoplasmic reticulum stress-induced apoptosis: multiple pathways and activation of p53-up-regulated modulator of apoptosis (PUMA) and NOXA by p53. J. Biol. Chem. 281: 7260-7270.
Engel, T., A. Sanz-Rodgriguez, E. M. Jimenez-Mateos, C. G. Concannon, A. Jimenez-Pacheco, C. Moran, G. Mesuret, E. Petit, N. Delanty, M. A. Farrell, D. F. O'Brien, J. H. Prehn, J. J. Lucas, and D. C. Henshall. 2013. CHOP regulates the p53-MDM2 axis and is required for neuronal survival after seizures. Brain 136: 577-592.
Guo, G., L. Marrero, P. Rodriguez, V. L. Del, A. Ochoa, and Y. Cui. 2013. Trp53 inactivation in the tumor microenvironment promotes tumor progression by expanding the immunosuppressive lymphoid-like stromal network. Cancer Res. 73: 1668-1675.
Laurent, A., C. Nicco, C. Chereau, C. Goulvestre, J. Alexandre, A. Alves, E. Levy, F. Goldwasser, Y. Panis, O Soubrane, B. Weill, and F. Batteux. 2005. Controlling tumor growth by modulating endogenous production of reactive oxygen species. Cancer Res. 65: 948-956.
Rodriguez, P. C., C. P. Hernandez, D. Quiceno, S. M. Dubinett, J. Zabaleta, J. B. Ochoa, J. Gilbert, and A. C. Ochoa. 2005. Arginase I in myeloid suppressor cells is induced by COX-2 in lung carcinoma. J. Exp. Med. 202: 931-939.
Jayaraman, R, F. Parikh, E. Lopez-Rivera, Y. Hailemichael, A. Clark, G. Ma, D. Cannan, M. Ramacher, M. Kato, W. W. Overwijk,

(56) References Cited

OTHER PUBLICATIONS

S. H. Chen, V. Y. Umansky, and A. G. Sikora. 2012. Tumor-expressed inducible nitric oxide synthase controls induction of functional myeloid-derived suppressor cells through modulation of vascular endothelial growth factor release. J. Immunol. 188: 5365-5376.

Lu, T., R. Ramakrishnan, S. Altiok, J. I. Youn, P. Cheng, E. Celis, V. Pisarev, S. Sherman, M. B. Sporn, and D. Gabrilovich. 2011. Tumor-infiltrating myeloid cells induce tumor cell resistance to cytotoxic T cells in mice. J. Clin. Invest 121: 4015-4029.

Calcinotto, A., P. Filipazzi, M. Grioni, M. Iero, M. A. De, A. Ricupito, A. Cova, R. Canese, E. Jachetti, M. Rossetti, V. Huber, G. Parmiani, L. Generoso, M. Santinami, M. Borghi, S. Fais, M. Bellone, and L. Rivoltini. 2012. Modulation of microenvironment acidity reverses anergy in human and murine tumor-infiltrating T lymphocytes. Cancer Res. 72: 2746-2756.

Munn, D. H., M. D. Sharma, B. Baban, H. P. Harding, Y. Zhang, D. Ron, and A. L. Mellor. 2005. GCN2 kinase in T. cells mediates proliferative arrest and anergy induction in response to indoleamine 2,3-dioxygenase. Immunity. 22: 633-642.

Rodriguez, P. C., A. H. Zea, J. DeSalvo, K. S. Culotta, J. Zabaleta, D. G. Quiceno, J. B. Ochoa, and A. C. Ochoa. 2003. L-arginine consumption by macrophages modulates the expression of CD3zeta chain in T lymphocytes. J. Immunol. 171: 1232-1239.

Srivastava, M. K., P. Sinha, V. K. Clements, P. Rodriguez, and S. Ostrand-Rosenberg. 2010. Myeloid-derived suppressor cells inhibit T-cell activation by depleting cystine and cysteine. Cancer Res. 70: 68-77.

Rodriguez, P. C., D. G. Quiceno, and A. C. Ochoa. 2007. L-arginine availability regulates T-lymphocyte cell-cycle progression. Blood 109: 1568-1573.

Scheuner, D., B. Song, E. McEwen, C. Liu, R. Laybutt, P. Gillespie, T. Saunders, S. Bonner-Weir, and R. J. Kaufman. 2001. Translational control is required for the unfolded protein response and in vivo glucose homeostasis. Mol. Cell 7: 1165-1176.

Rodriguez, P. C., C. P. Hernandez, K. Morrow, R. Sierra, J. Zabaleta, D. D. Wyczechowska, and A. C. Ochoa. 2010. L-arginine deprivation regulates cyclin D3 mRNA stability in human T cells by controlling HuR expression. J. Immunol. 185: 5198-5204.

Chitnis, N. S., D. Pytel, E. Bobrovnikova-Marjon, D. Pant, H. Zheng, N. L. Maas, B. Frederick, J. A. Kushner, L. A. Chodosh, C. Koumenis, S. Y. Fuchs, and J. A. Diehl. 2012. miR-211 is a prosurvival microRNA that regulates chop expression in a PERK-dependent manner. Mol. Cell 48: 353-364.

Bunpo, P., A. Dudley, J. K. Cundiff, D. R. Cavener, R. C. Wek, and T. G. Anthony. 2009. GCN2 protein kinase is required to activate amino acid deprivation responses in mice treated with the anti-cancer agent L-asparaginase. J. Biol. Chem. 284: 32742-32749.

Mehrotra, S., A. A. Al-Khami, J. Klarquist, J. Husain, O. Naga, J. M. Eby, A. K. Murali, G. E. Lyons, M. Li, N. D. Spivey, H. Norell, P. T. Martins da, G. Onicescu, C. M. az-Montero, E. Garrett-Mayer, D. J. Cole, P. Le, I, and M. I. Nishimura. 2012. A Coreceptor-Independent Transgenic Human TCR Mediates Anti-Tumor and Anti-Self Immunity in Mice. J. Immunol. 189: 1627-1638.

Loinard, C., Y. Zouggari, P. Rueda, B. Ramkhelawon, C. Cochain, J. Vilar, A. Recalde, A. Richart, D. Charue, M. Duriez, M. Mori, F. renzana-Seisdedos, B. I. Levy, C. Heymes, and J. S. Silvestre. 2012. C/EBP homologous protein-10 (CHOP-10) limits postnatal neovascularization through control of endothelial nitric oxide synthase gene expression. Circulation 125: 1014-1026.

Hernandez, C. P., K. Morrow, C. Velasco, D. D. Wyczechowska, A. S. Naura, and P. C. Rodriguez. 2013. Effects of cigarette smoke extract on primary activated T cells. Cell Immunol. 282: 38-43.

Kibe, R., S. Zhang, D. Guo, L. Marrero, F. Tsien, P. Rodriguez, S. Khan, A. Zieske, J. Huang, W. Li, S. K. Durum, T. Iwakuma, and Y. Cui. 2012. IL-7Ralpha deficiency in p53null mice exacerbates thymocyte telomere erosion and lymphomagenesis. Cell Death. Differ. 19: 1139-1151.

\* cited by examiner

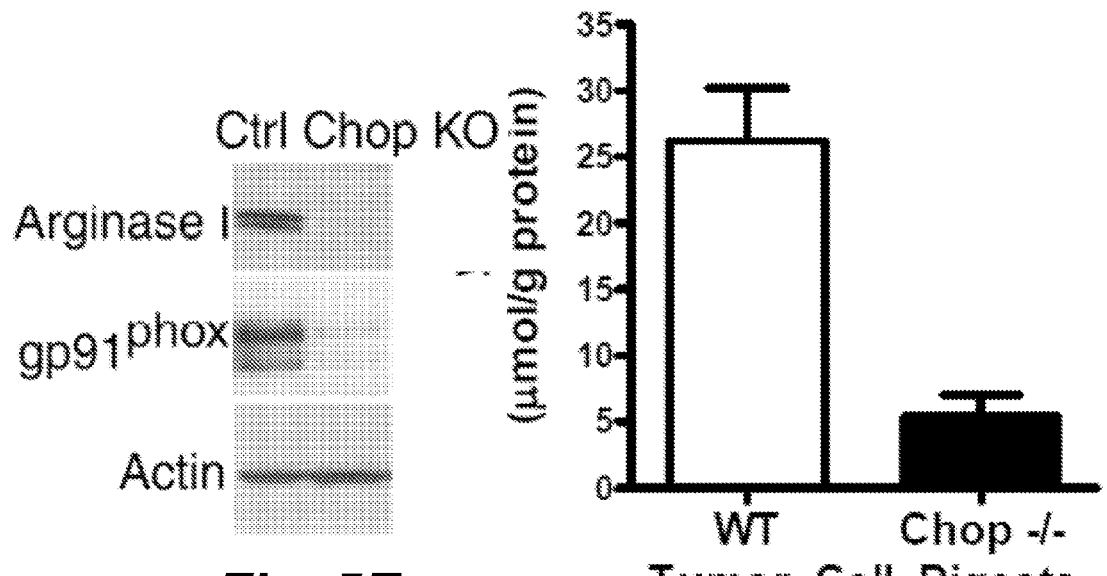
*Fig. 5E*
*Fig. 5F*
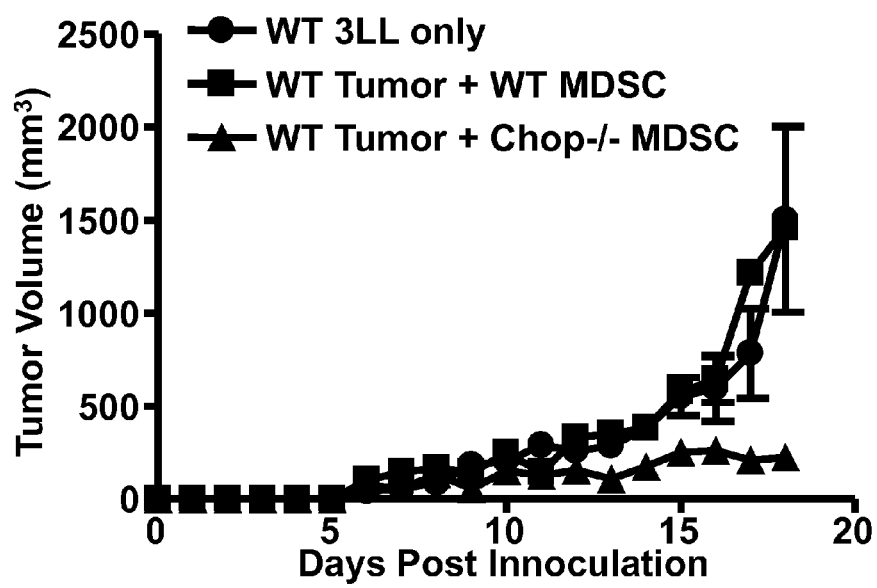
*Fig. 6A*

SEQUENCE LISTING

<160> NUMBER OF SEQ ID NOS: 28

<210> SEQ ID NO 1
<211> LENGTH: 21
<212> TYPE: DNA
<213> ORGANISM: Artificial sequence
<220> FEATURE:
<223> OTHER INFORMATION: siRNA #2 First Strand

<400> SEQUENCE: 1
ccaacagagg ucacacgcat t                                              21

<210> SEQ ID NO 2
<211> LENGTH: 20
<212> TYPE: DNA
<213> ORGANISM: Artificial sequence
<220> FEATURE:
<223> OTHER INFORMATION: Murine Chop Forward PCR Primer

<400> SEQUENCE: 2
ggagctggaa gcctggtatg                                                20

<210> SEQ ID NO 3
<211> LENGTH: 20
<212> TYPE: DNA
<213> ORGANISM: Artificial sequence
<220> FEATURE:
<223> OTHER INFORMATION: Murine Chop Reverse PCR Primer

<400> SEQUENCE: 3
ggatgtgcgt gtgacctctg                                                20

<210> SEQ ID NO 4
<211> LENGTH: 20
<212> TYPE: DNA
<213> ORGANISM: Artificial sequence
<220> FEATURE:
<223> OTHER INFORMATION: Atf4 Forward PCR Primer

<400> SEQUENCE: 4
gcctgactct gctgcttaca                                                20

<210> SEQ ID NO 5
<211> LENGTH: 20

```
<212> TYPE: DNA
<213> ORGANISM: Artificial sequence
<220> FEATURE:
<223> OTHER INFORMATION: Atf4 Reverse PCR Primer

<400> SEQUENCE: 5
cttgccttac ggacctcttc                                              20

<210> SEQ ID NO 6
<211> LENGTH: 20
<212> TYPE: DNA
<213> ORGANISM: Artificial sequence
<220> FEATURE:
<223> OTHER INFORMATION: C/EBPbeta Forward PCR Primer

<400> SEQUENCE: 6
gacaagctga gcgacgagta                                              20

<210> SEQ ID NO 7
<211> LENGTH: 20
<212> TYPE: DNA
<213> ORGANISM: Artificial sequence
<220> FEATURE:
<223> OTHER INFORMATION: C/EBPbeta Reverse PCT Primer

<400> SEQUENCE: 7
agctgctcca ccttcttctg                                              20

<210> SEQ ID NO 8
<211> LENGTH: 24
<212> TYPE: DNA
<213> ORGANISM: Artificial sequence
<220> FEATURE:
<223> OTHER INFORMATION: Actb Forwrad PCR Primer

<400> SEQUENCE: 8
tgtgatggtg ggaatgggtc agaa                                         24

<210> SEQ ID NO 9
<211> LENGTH: 24
<212> TYPE: DNA
<213> ORGANISM: Artificial sequence
<220> FEATURE:
<223> OTHER INFORMATION: Actb Reverse PCR Primer

<400> SEQUENCE: 9
tgtggtgcca gatcttctcc atgt                                         24

<210> SEQ ID NO 10
<211> LENGTH: 21
<212> TYPE: DNA
<213> ORGANISM: Artificial sequence
<220> FEATURE:
<223> OTHER INFORMATION: siRNA #1 First Strand

<400> SEQUENCE: 10
ggaagaacua ggaaacggat t                                            21

<210> SEQ ID NO 11
<211> LENGTH: 21
<212> TYPE: DNA
<213> ORGANISM: Artificial sequence
<220> FEATURE:
<223> OTHER INFORMATION: siRNA #1 Second Strand

<400> SEQUENCE: 11
```
uccguuuccu aguucuuccu t                                              21

<210> SEQ ID NO 12
<211> LENGTH: 21
<212> TYPE: DNA
<213> ORGANISM: Artificial sequence
<220> FEATURE:
<223> OTHER INFORMATION: siRNA #2 Second Strand

<400> SEQUENCE: 12
ugcgugugac cucuguuggt t                                              21

<210> SEQ ID NO 13
<211> LENGTH: 21
<212> TYPE: DNA
<213> ORGANISM: Artificial sequence
<220> FEATURE:
<223> OTHER INFORMATION: siRNA #3 First Strand

<400> SEQUENCE: 13
gucagaguuc uauggcccat t                                              21

<210> SEQ ID NO 14
<211> LENGTH: 21
<212> TYPE: DNA
<213> ORGANISM: Artificial sequence
<220> FEATURE:
<223> OTHER INFORMATION: siRNA #3 Second Strand

<400> SEQUENCE: 14
ugggccauag aacucugact t                                              21

<210> SEQ ID NO 15
<211> LENGTH: 21
<212> TYPE: DNA
<213> ORGANISM: Artificial sequence
<220> FEATURE:
<223> OTHER INFORMATION: siRNA #4 First Strand

<400> SEQUENCE: 15
cggaaagugg cacagcuagt t                                              21

<210> SEQ ID NO 16
<211> LENGTH: 21
<212> TYPE: DNA
<213> ORGANISM: Artificial sequence
<220> FEATURE:
<223> OTHER INFORMATION: siRNA #4 Second Strand

<400> SEQUENCE: 16
cuagcugugc cacuuuccgt t                                              21

<210> SEQ ID NO 17
<211> LENGTH: 21
<212> TYPE: DNA
<213> ORGANISM: Artificial sequence
<220> FEATURE:
<223> OTHER INFORMATION: siRNA #5 First Strand

<400> SEQUENCE: 17
gaagaacuag gaaacggaat t                                              21

<210> SEQ ID NO 18
<211> LENGTH: 21
<212> TYPE: DNA
<213> ORGANISM: Artificial sequence

```
<220> FEATURE:
<223> OTHER INFORMATION: siRNA #5 Second Strand

<400> SEQUENCE: 18
uuccguuucc uaguucuuct t                                                 21

<210> SEQ ID NO 19
<211> LENGTH: 21
<212> TYPE: DNA
<213> ORGANISM: Artificial sequence
<220> FEATURE:
<223> OTHER INFORMATION: siRNA #6 First Strand

<400> SEQUENCE: 19
gucccuagcu uggcugacat t                                                 21

<210> SEQ ID NO 20
<211> LENGTH: 21
<212> TYPE: DNA
<213> ORGANISM: Artificial sequence
<220> FEATURE:
<223> OTHER INFORMATION: siRNA #6 Second Strand

<400> SEQUENCE: 20
ugucagccaa gcuagggact t                                                 21

<210> SEQ ID NO 21
<211> LENGTH: 21
<212> TYPE: DNA
<213> ORGANISM: Artificial sequence
<220> FEATURE:
<223> OTHER INFORMATION: siRNA #7 First Strand

<400> SEQUENCE: 21
gucacacgca caucccaaat t                                                 21

<210> SEQ ID NO 22
<211> LENGTH: 21
<212> TYPE: DNA
<213> ORGANISM: Artificial sequence
<220> FEATURE:
<223> OTHER INFORMATION: siRNA #7 Second Strand

<400> SEQUENCE: 22
uuugggaugu gcgugugact t                                                 21

<210> SEQ ID NO 23
<211> LENGTH: 21
<212> TYPE: DNA
<213> ORGANISM: Artificial sequence
<220> FEATURE:
<223> OTHER INFORMATION: siRNA #8 First Strand

<400> SEQUENCE: 23
cucuccagau uccagucagt t                                                 21

<210> SEQ ID NO 24
<211> LENGTH: 21
<212> TYPE: DNA
<213> ORGANISM: Artificial sequence
<220> FEATURE:
<223> OTHER INFORMATION: siRNA #8 Second Strand

<400> SEQUENCE: 24
cugacuggaa ucuggagagt t                                                 21
```

```
<210> SEQ ID NO 25
<211> LENGTH: 21
<212> TYPE: DNA
<213> ORGANISM: Artificial sequence
<220> FEATURE:
<223> OTHER INFORMATION: siRNA #9 First Strand

<400> SEQUENCE: 25
gagcaaggaa gaacuaggat t                                            21

<210> SEQ ID NO 26
<211> LENGTH: 21
<212> TYPE: DNA
<213> ORGANISM: Artificial sequence
<220> FEATURE:
<223> OTHER INFORMATION: siRNA #9 Second Strand

<400> SEQUENCE: 26
uccuaguucu uccuugcuct t                                            21

<210> SEQ ID NO 27
<211> LENGTH: 21
<212> TYPE: DNA
<213> ORGANISM: Artificial sequence
<220> FEATURE:
<223> OTHER INFORMATION: siRNA #10 First Strand

<400> SEQUENCE: 27
caacagaggu cacacgcact t                                            21

<210> SEQ ID NO 28
<211> LENGTH: 21
<212> TYPE: DNA
<213> ORGANISM: Artificial sequence
<220> FEATURE:
<223> OTHER INFORMATION: siRNA #10 Second Strand

<400> SEQUENCE: 28
gugcguguga ccucuguugt t                                            21
```

COMPOSITIONS AND METHODS FOR REDUCING C/EBP HOMOLOGOUS PROTEIN ACTIVITY IN MYELOID-DERIVED SUPPRESSOR CELLS

CROSS-REFERENCE TO RELATED APPLICATION

This application is the 35 U.S.C. §371 national stage application of PCT Application No. PCT/US2015/020692, filed Mar. 16, 2015, where the PCT claims priority to U.S. Provisional Application No. 61/954,072, entitled "METHOD TO TREAT HUMAN DISEASE BY REDUCING MDSC-ASSOCIATED IMMUNOSUPPRESSION" filed on Mar. 17, 2014, both of which are herein incorporated by reference in their entirety.

STATEMENT REGARDING FEDERALLY SPONSORED RESEARCH OR DEVELOPMENT

This Invention was made with Government support under Grant Nos. R21CA162133, P20 GM103501 and 1R01CA184185, awarded by the National Institutes of Health. The Government has certain rights in the Invention.

FIELD OF DISCLOSURE

The present disclosure relates to agents that inhibit the C/EBP homologous stress-related protein (Chop) or Chop-upstream mediators in Myeloid-derived Suppressor Cells (MDSCs). The disclosure further relates to compounds or agents that can increase immune responses to a tumor.

SEQUENCE LISTING

The present disclosure includes a sequence listing incorporated herein by reference in its entirety.

BACKGROUND

Myeloid cells are an important group of immune cells that represent the first line of defense against different pathogens and can be divided into granulocytic and monocytic sub-populations. Granulocytic myeloid cells (polymorphonu-clear granulocytes or neutrophils, eosinophil granulocytes, and basophil granulocytes) are the first line of immune defense during bacterial, viral or parasitic infections. Among them, polymorphonuclear cells (PMN) play an essential role in the defense against extracellular bacteria, while eosinophils regulate immune defense against parasites. In addition, eosinophil granulocytes and basophil granulocytes are involved in the development of allergic reactions. Monocytic myeloid cells (dendritic cells, macrophages) play an essential role in phagocytosis and in the processing and presentation of antigens.

Under pathological conditions, the differentiation homeostasis of myeloid cells is impaired, leading to the accumulation of Myeloid-derived suppressor cells (MDSCs), a heterogeneous population of immature myeloid cells characterized by their suppressive actions on innate and adaptive immune cells such as T cells, dendritic cells, and natural killer (NK) cells. MDSC inhibit T- and NK cell responses through several pathways including the increased expression of arginase I, inducible nitric oxide synthase (iNOS), and gp91$^{phox}$, and the high release of reactive oxygen species (ROS), peroxynitrites (PNT), and prostaglandin E2 (PGE$_2$).

In addition to their immunoregulatory activity, MDSC also promote tumor angiogenesis and metastasis. MDSCs can be divided into granulocytic and monocytic subsets based on different markers and morphological features. Both types of cells are also produced during tissue damage caused either by trauma (surgical or other), chronic infectious diseases, and by the growth of tumors. In the first case, both granulocytic and monocytic cells play an essential role in the healing of the damaged tissues. In other forms of chronic disease such as cancer, autoimmunity or chronic infection, these cells are also produced initially with the goal of "healing" damaged tissues, however the chronic nature of these diseases and the inability of the myeloid cells to heal the damage turns these cells into chronic inflammatory cells which in turn suppress the T- and B cell immune response.

Multiple pro-inflammatory mediators present in the tumor microenvironment induce the generation and accumulation of MDSCs. The numbers of MDSCs increase with cancer burden, a problematic event since MDSCs are also shown to inhibit immune cancer therapeutics and immunotherapy. The inhibitory role of MDSC is widely accepted as a major obstacle for immunotherapy. They not only represent a major obstacle in the successful development of different forms of immunotherapy, but are also an attractive therapeutic target. Minimizing MDSC-mediated immunosuppression is important not only to developing novel therapeutics, but also in increasing the effectiveness of therapeutics currently used.

MDSC produce several factors that can block the immune function, factors which normally function to minimize unwanted tissue damage. Unfortunately, this often prevents a protective immune response mediated by T cells, NK calls and B cells, for example. Among these factors that inhibit the immune function are Arginase (I and II) that consume arginine in the microenvironment, nitric oxide synthase (NOS) which consumes arginine and makes nitric oxide, nitric oxide (NO) which is able to induce apoptosis of T cells and inhibit the function of cellular receptors in T cells, and hydrogen peroxide (H$_2$O$_2$) that also induces T cell apoptosis. In cancer, for example, great efforts have been made to block one or more of these different immunosuppressive mediators with the goal of preventing unwanted immunosuppression and allowing the immune system to eliminate the malignant cells. Unfortunately, the multiple redundant pathways that MDSC use to block the immune response and the ability of the bone marrow to produce up to 10$^{e11}$ MDSC daily have prevented these approaches from having any significant effect.

SUMMARY

One aspect of the disclosure encompasses embodiments of a method of modulating the level of activity of C/EBP-homologous protein (Chop) in a myeloid-derived suppressor cell (MDSC) or population of said cells, said method comprising delivering to a recipient MDSC or population of said recipient cells a composition comprising an agent that inhibits the activity of Chop in the cell(s) or reduces the expression of a Chop or a derivative thereof, and a vehicle for delivery of the agent to the interior of the recipient cell.

In some embodiments of this aspect of the disclosure, the agent can be an siRNA and result in gene silencing of the Chop gene in the recipient MDSC or population of MDSCs.

In some embodiments of this aspect of the disclosure, the siRNA can be an isolated double-stranded ribonucleic acid (dsRNA) molecule having either no overhang regions or at least one overhang region, wherein each overhang region contains six or fewer nucleotides, and wherein the dsRNA inhibits expression by a cell of a Chop protein, and wherein a first strand of the dsRNA is substantially identical to the sequence according to SEQ ID NO: 1, and a second strand is substantially complementary to the first.

In some embodiments of this aspect of the disclosure, the first strand of the dsRNA can have a nucleotide sequence according to SEQ ID NO: 1.

In some embodiments of this aspect of the disclosure, the composition is administered to the recipient animal or human subject intravenously or directly into a tumor of said subject.

Another aspect of the disclosure encompasses embodiments of a composition comprising an agent that when delivered to a myeloid-derived suppressor cell (MDSC) or population of said cells reduces the level of expression of a Chop-encoding gene, thereby reducing the level of Chop in the cell or cells.

In some embodiments of this aspect of the disclosure, the siRNA can be an isolated double-stranded ribonucleic acid (dsRNA) molecule having either no overhang regions or at least one overhang region, wherein each overhang region contains six or fewer nucleotides, and wherein the dsRNA inhibits expression by a cell of a Chop protein, and wherein a first strand of the dsRNA is substantially identical to the sequence according to SEQ ID NO: 1, and a second strand is substantially complementary to the first.

In some embodiments of this aspect of the disclosure, the first strand of the dsRNA has a nucleotide sequence according to SEQ ID NO: 1.

Another aspect of the disclosure encompasses embodiments of a method of increasing the efficacy of an immune system-based treatment of a tumor comprising the steps of: (a) delivering to an animal or human subject a pharmaceutically acceptable composition providing a T cell based immunotherapeutic reduction in a tumor; (b) reducing the level of activity of C/EBP-homologous protein (Chop) in a population of myeloid-derived suppressor cells (MDSCs) in the animal or human subject, said method comprising delivering to said subject a pharmaceutically acceptable composition comprising an effective dose of an siRNA, a pegylated-liposome vehicle for delivery of the siRNA to the interior of the MDSCs, and a pharmaceutically acceptable carrier, wherein the siRNA is an isolated double-stranded ribonucleic acid (dsRNA) molecule having either no overhang regions or at least one overhang region, wherein each overhang region contains six or fewer nucleotides, and wherein the dsRNA inhibits expression by a cell of a Chop protein, and wherein a first strand of the dsRNA is substantially identical to the sequence according to SEQ ID NO: 1, and a second strand is substantially complementary to the first, and results in gene silencing of the Chop gene in the recipient MDSCs; thereby increasing the efficacy of the T cell based immunotherapy directed against the tumor.

BRIEF DESCRIPTION OF THE DRAWINGS

Many aspects of the disclosure can be better understood with reference to the following drawings.

FIG. 1A illustrates the expression of mRNA levels for ISR-related gene Chop.

FIG. 1B is a digital image of a gel analysis of Chop protein expression in G-M DSC and M-MDSC subsets.

FIG. 1C illustrates the expression of mRNA levels for ISR-related gene PERK.

FIG. 1D illustrates the expression of mRNA levels for ISR-related gene Atf4.

FIGS. 3A and 3B illustrate tumor growth in Chop KO (FIG. 3B) and wild-type (FIG. 3A) mice bearing 3LL cells, which received twice a week 0.5 mg anti-CD4 or anti-CD8 antibodies.

FIG. 3C illustrates the accumulation of $CD8^+$ cells in tumors measured 17 days after tumor injection.

FIG. 3D illustrates the accumulation of $CD4^+Foxp3^+$ cells in spleen measured 17 days after tumor injection.

FIG. 3E illustrates flow cytometry of spleen cells activated (anti-CD3/CD28) and also IFNγ production.

FIG. 3F illustrates CD3ζ levels in samples from FIG. 3C.

FIG. 4A illustrates tumor volume changes in wild-type and Chop KO mice-bearing 3LL-OVA tumors for 7 days receiving $1 \times 10^6$ OT-1 cells, followed by immunization with SIINFEKL, and tumor growth monitoring.

FIG. 4B illustrates spleens tested for IFNγ using Elispot (48 h). Spleens were collected 8 days after vaccination and challenged with SIINFEKL.

FIGS. 5A-5F illustrate that Chop controls global function of tumor-infiltrating MDSC.

FIG. 5A illustrates the accumulation of MDSC, G-MDSC, and M-MDSC in spleens of wild-type and Chop KO mice.

FIG. 5B illustrates the accumulation of MDSC, G-MDSC, and M-MDSC in tumors of wild-type and Chop KO mice.

FIG. 5C illustrates T cells proliferation when $CD11b^+ Gr1^+$ cells from tumors were co-cultured in different ratios with anti-CD3/CD28-activated T cells.

FIG. 5D illustrates IFNγ expression when $CD11b^+Gr1^+$ cells from tumors were co-cultured in different ratios with anti-CD3/CD28-activated T cells.

FIG. 5E illustrates the expression of MDSC-suppressive factors in tumor-MDSCs.

FIG. 5F illustrates the expression of PNT in tumor-MDSCs.

FIGS. 6A-6C illustrate that adoptive transfer of Chop KO MDSC prevents tumor growth.

FIGS. 6A and 6B illustrate that injection of Chop KO MDSCs prevented tumor growth in wild-type mice, while wild-type MDSC partially restored tumor growth in Chop KO mice.

FIG. 6C illustrates when tumor-isolated $CD11b^+Gr1^+$ cells from Chop KO and controls were co-cultured with LDH-labeled 3LL cells and tumor toxicity was measured.

FIG. 8A illustrates Chop in in vitro-generated MDSCs cultured in the presence of different stress factors present in tumors.

FIG. 8B illustrates acidosis and PNT increased suppressive activity in MDSCs.

FIG. 9A illustrates decreased binding of LAP/LAP*, but not LIP, to a consensus DNA sequence in Chop KO MDSC.

FIG. 9B illustrates expression of LIP, LAP, and LAP* in MDSC-extracts from Chop KO and wild-type mice bearing 3LL tumors.

FIG. 10A illustrates Chop mRNA in 3LL cells transfected with different Chop-siRNA and treated with tunicamycin.

FIG. 10B illustrates Fam-labeled siRNA distribution in 3LL tumors after a single i.p. injection.

FIG. 10C illustrates the silencing of Chop in tumors after 3 days of i.p. injection of 5 mg/kg of PEG-liposomes Chop siRNA #2 (n=5).

FIG. 12A illustrates Chop levels in specific stromal cell populations sorted by flow cytometry from single-cell suspensions of s.c. 3LL tumors 18 days after injection.

FIG. 12B illustrates Chop expression in splenic and tumor MDSCs recovered from mice bearing s.c. 3LL lung carcinoma, B16 melanoma, EL-4 thymoma, or MCA-38 colon carcinoma. Immature myeloid cells (iMCs) were obtained by sorting CD11b$^+$Gr1$^+$ cells from spleens of mice without tumors.

FIG. 12C illustrates immunofluorescence detection of Chop and CD33$^+$ in a panel of biopsies from advanced colon carcinoma patients. A representative slide from 24 patients.

FIG. 12D illustrates tumor growth kinetics in wild-type (WT; closed square) and Ddit3$^{-/-}$ (closed triangle) mice bearing s.c. 3LL lung carcinoma, B16 melanoma, EL-4 thymoma, or MCA-38 colon carcinoma. Average kinetics±SEM of ten mice per group from two replicates.

FIG. 13A illustrates CFSE-labeled CD3$^+$ T cells activated with anti-CD3/CD28 were co-cultured at different ratios with MDSCs isolated from wild-type and Ddit3$^{-/-}$ mice bearing s.c. 3LL tumors for 17 days. Proliferation and IFN-g expression in T cells was monitored 72 h later. Results are expressed as mean±SEM from ten mice per group from two independent experiments. p<0.01, *p<0.001

FIG. 13B illustrates CD3$^+$ T cells were activated with plate-bound anti-CD3/CD28 and co-cultured in a ratio of 1:1/4 with MDSCs sorted from wild-type, Ddit3$^{-/-}$, or Ddit3$^{-/-}$ bone marrow chimeric mice bearing 3LL cells for 17 days. Mean±SEM from three experiments. p<0.01, *p<0.001

FIG. 13C illustrates an immunoblot for arginase I and inducible nitric oxide synthase in isolated MDSCs. ELISA for PNT in MDSCs protein lysates. Assay of superoxide production in isolated MDSCs. All assessments performed on MDSCs isolated from wild-type or Ddit3$^{-/-}$ 3LL tumor-bearing mice 18 days after s.c. injection. Data plotted are pooled values from three experiments (n=5). p<0.01, *p<0.001

FIG. 13D illustrates IFN-g Elispot (representative images in left panel) of SIINFEKL-challenged lymph node cells from wild-type CD45.1$^+$ mice that received i.v. transfer of CD45.2$^+$ OT-I cells, SIINFEKL-loaded DCs, and SIINFEKL-pulsed MDSCs from wild-type or Ddit3$^{-/-}$ mice. Data are expressed as mean±SEM from three experiments having five independent samples. p<0.01, *p<0.001

FIG. 14A illustrates tumor growth in wild-type (left panel, closed symbols) and Ddit3$^{-/-}$ (right panel, open symbols) mice injected with 3LL cells alone (closed and open squares) or co-injected with tumor MDSCs from wild-type (closed and open diamonds) or Ddit3$^{-/-}$ (closed and open triangles) mice. Co-injected cells were mixed at a 1:1 ratio. Plots are from ten mice from two experiments. ***p<0.001.

FIG. 14B illustrates tumor growth kinetics in control wild-type mice (3LL alone, squares) or mice receiving i.v. transfer of wild-type (diamonds) or Ddit3$^{-/-}$ (circles) MDSCs (3×10$^6$) on days 3 and 6 after 3LL injection. ***p<0.001.

FIG. 14C illustrates LDH cytotoxicity assay of 3LL tumor cells after 6 h of co-culture with MDSCs from wild-type or Ddit3$^{-/-}$ mice bearing s.c. 3LL tumors for 17 days. Results are from three replicates (n=10). ***p<0.001.

FIG. 14D illustrates proliferation of CFSE-labeled CD8$^+$ OT-I cells after 72 h of priming with SIINFEKL-pulsed MDSCs from wild-type or Ddit3$^{-/-}$ mice (2 mg/ml for 4 h). Results are from three replicate experiments. ***p<0.001.

FIG. 15A illustrates percentage of CD45$^+$CD3$^+$CD8$^+$ T cells in single-cell suspensions of 3LL tumors from wild-type and Ddit3$^{-/-}$ mice after 17 days of tumor injection.

FIG. 15B illustrates tumor growth in 3LL tumor-bearing wild-type and Ddit3$^{-/-}$ mice treated with antibodies against CD8$^+$ or CD4$^+$ T cells (isotype, square; anti-CD4, triangle; anti-CD8, circle). Data from five mice per group.

FIG. 15C illustrates wild-type and Ddit3$^{-/-}$ (CD45.2$^+$) mice bearing s.c. 3LL-OVA tumors for 7 days, which were left untreated or received adoptive transfer with naive CD45.1$^+$CD8$^+$ OT-I cells (5×10$^6$), followed by immunization with SIINFEKL. Then, they were followed for tumor growth. Closed square, wild-type (WT) no adoptive transfer; open square, WT plus OT-I adoptive transfer; closed triangle, Ddit3$^{-/-}$ no adoptive transfer; open triangle, Ddit3$^{-/-}$ plus OT-I adoptive transfer.

FIG. 16A illustrates Chop expression in BM MDSCs±40% TES with or without the addition of 2 mM L-NAC, 100 mM PTIO, or 100 mM MnTBAP. Data are expressed as mean±SEM from a representative experiment of three replicates. ***p<0.001.

FIG. 16B illustrates Chop and arginase I expression in MDSCs from 3LL-bearing mice treated daily i.p. with PBS or 1 mg/kg L-NAC. Data are expressed as mean±SEM from a representative experiment of three replicates. ***p<0.001.

FIG. 16C illustrates tumor progression in mice with PBS or 1 mg/kg L-NAC. n=10 from 2 experiments. Data are expressed as mean±SEM from a representative experiment of three replicates. ***p<0.001.

FIG. 16D illustrates proliferation of CFSE-labeled T cells 72 h after co-culture with different numbers of tumor MDSCs recovered from PBS- or L-NAC-treated 3LL tumor-bearing mice. Data are expressed as mean±SEM from a representative experiment of three replicates. ***p<0.001.

FIG. 16E illustrates expression of Chop in TES-treated wild-type and $Gp91^{phox-/-}$ BM MDSCs. Data are expressed as mean±SEM from a representative experiment of three replicates. ***p<0.001.

DETAILED DESCRIPTION OF DISCLOSURE

Figure 1A:
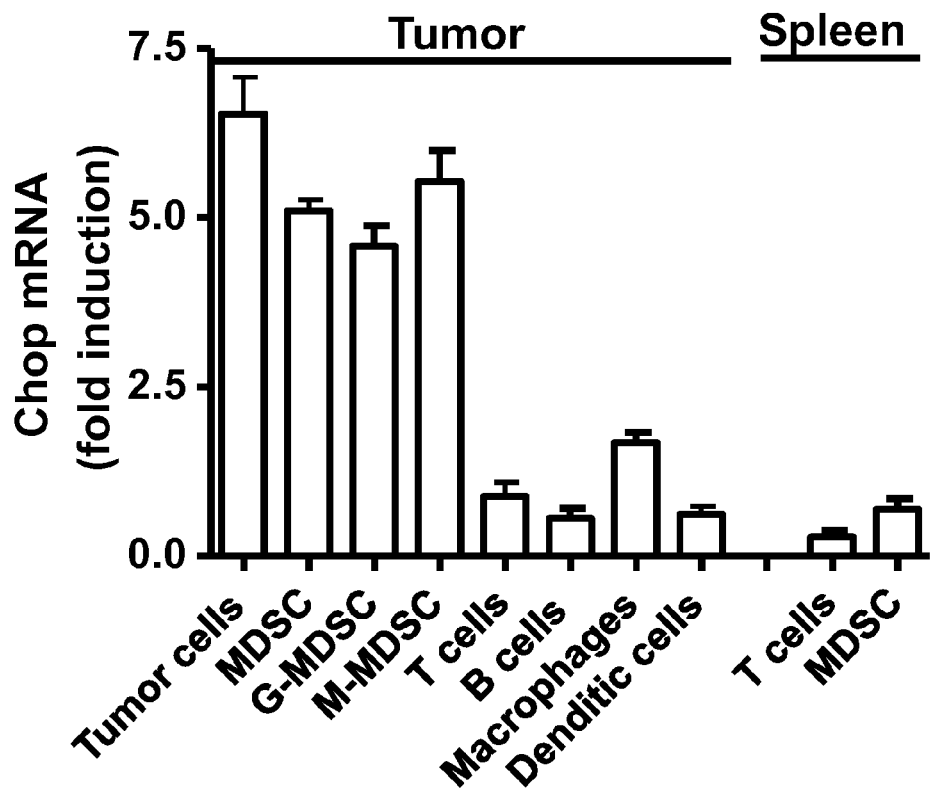
FIGS. 1A-1D illustrate integrated stress response (ISR) levels in cellular populations from 3LL tumors.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Abbreviations

Chop, C/EBP homologous stress-related protein; MDSC(s), Myeloid-derived Suppressor Cell(s); iNOS, inducible nitric oxide synthase; ROS, reactive oxygen species; PNT, peroxynitrites; $PGE_2$, prostaglandin E2; dsRNA, double-strand RNA; siRNA, small interfering RNA; iRNA, RNA interference; ISR, integrated stress response; KO, knockout (mouse); G-MDSC, granulocyte-Myeloid-derived Suppressor Cell, M-MDSC, monocyte-Myeloid-derived Suppressor Cell; BM, bone marrow; TES, tumor explant supernatants.

Definitions

In describing and claiming the disclosed subject matter, the following terminology will be used in accordance with the definitions set forth below.

The terms "administering" and "administration" as used herein refer to introducing a composition (e.g., a therapeutic composition) of the present disclosure into a subject. While an advantageous route of administration of a composition can be intravenous, any route of administration, such as oral, topical, subcutaneous, peritoneal, intra-arterial, inhalation, vaginal, rectal, nasal, introduction into the cerebrospinal fluid, or instillation into body compartments, can be used and may be formulated, alone or together, in suitable dosage unit formulations containing conventional non-toxic pharmaceutically acceptable carriers, adjuvants and vehicles appropriate for each route of administration.

The term "cancer", as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult. Benign tumors have less of a tendency to invade and are less likely to metastasize.

The term "cell or population of cells" as used herein refers to an isolated cell or plurality of cells excised from a tissue or grown in vitro by tissue culture techniques. Most particularly, a population of cells refers to cells in vivo in a tissue of an animal or human.

The term "C/EBP Homologous Stress-Related Protein (Chop)" as used herein refers to DNA damage-inducible transcript 3, a transcription factor that is encoded by the DDIT3 gene. The human and mouse variants of the Chop protein are encoded by mRNAs having the GenBank Accession Nos. NM_001195053 and NM_001290183, respectively. The human and mouse variants of the Chop protein have the amino acid sequences having the GenBank Accession Nos. NP_001181982 and NP_001277112, respectively.

The term "coding sequence" as used herein refers to a sequence which "encodes" a selected polypeptide and is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

The term "complementary" as used herein refers to a sufficient number of matching base pairs in an oligonucleotide sequence to interact specifically (hybridize) with the target nucleic acid sequence to be amplified or detected. In the art, a very high degree of complementarity is needed for hybridization specificity and sensitivity, although it need not be 100%.

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

When a compound of the present disclosure is used contemporaneously with one or more other drugs, a pharmaceutical composition containing such other drugs in addition to the compound of the present disclosure is contemplated. Accordingly, the pharmaceutical compositions of the present disclosure include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used. Thus, for example, but not intended to be limiting, when a compound of the present disclosure is combined with another agent, the weight ratio of the compound of the present disclosure to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used. In such combinations the compound of the present disclosure and other active agents may be administered separately or in conjunction. In addition, the administration of one element may be prior to, concurrent to, or subsequent to the administration of other agent(s).

A compound of the disclosure of the disclosure may be formulated into a pharmaceutical composition for administration to a subject by appropriate methods known in the art. A composition of the disclosure may be sterilized by, for example, filtration through a bacteria retaining filter, addition of sterilizing agents to the composition, irradiation of the composition, or heating the composition. Alternatively, the compounds or compositions of the present disclosure may be provided as sterile solid preparations e.g. lyophilized powder, which are readily dissolved in sterile solvent immediately prior to use.

The term "contacting a cell or population of cells" as used herein refers to delivering a composition according to the present disclosure (i.e. an agent that modulates the activity or expression of the Chop protein) to an isolated or cultured cell or population of cells, or administering the probe in a suitable pharmaceutically acceptable carrier to the target tissue of an animal or human. Administration may be, but is not limited to, intravenous delivery, intraperitoneal delivery, intramuscularly, subcutaneously, or by any other method known in the art. One advantageous method is to deliver directly into a blood vessel leading into a target organ or tissue such as a prostate, and so reducing dilution of the probe in the general circulatory system.

The term "delivering to a cell" as used herein can further refer to the direct targeting of a cell with a small molecule compound, a nucleic acid, a peptide or polypeptide, or a nucleic acid capable of expressing an inhibitory nucleic acid or polypeptide by systemic targeted delivery for in vivo administration, or by incubation of the cell or cells with said effector ex vivo or in vitro.

The terms "effective amount," "therapeutically-effective amount," and "therapeutically effective dose" as used herein refer to the amount of a compound, material, or composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated or a reduction in a side-effect due to an administered pharmaceutical agent.

The terms "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, an amino acid sequence or a portion thereof.

The term "formulation" as used herein refers to a composition that may be a stock solution of the components, or a composition, preferably including a dilutant such as water or other pharmaceutically acceptable carrier that may be available for distribution including to a patient or physician.

The term "gene" as used herein refers to a functional protein-, polypeptide-, or peptide-encoding nucleic acid unit, e.g., a Chop-encoding nucleic acid. As will be understood by those in the art, this functional term includes genomic sequences, cDNA sequences, probes, oligonucleotides or fragments thereof (and combinations thereof), as well as gene products, including those that may have been designed and/or altered by the user. Purified genes, nucleic acids, protein and the like are used to refer to these entities when identified and separated from at least one contaminating nucleic acid or protein with which it is ordinarily associated.

The term "gene silencing" as used herein refers to a process by which the expression of a specific gene product is lessened or attenuated. As used herein, gene silencing refers to decreases in gene product expression that results from RNA interference (RNAi), a defined, though partially characterized pathway whereby small inhibitory RNA (siRNA) act in concert with host proteins (e.g., the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g., DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g., fluorescent properties (e.g., GFP) or enzymatic activity (e.g., alkaline phosphatases), or several other procedures.

The term "hybridization" as used herein refers to the process of association of two nucleic acid strands to form an anti-parallel duplex stabilized by hydrogen bonding between opposing strands. The terms "hybridizing" and "binding" are used interchangeably and is meant the formation of complementary A-T and C-G base pairs between the nucleotide sequences of two polynucleotide segments. The hybridized strands are called a "duplex."

The terms "hybridization affinity" and "hybridizing affinity" as used herein refers to the property of an oligonucleotide to complement with and hybridize to another nucleotide sequence to form a nucleic acid duplex.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "identity" as used herein refers to a relationship between two or more polypeptide sequences, as determined by comparing the sequences. In the art, "identity" also refers to the degree of sequence relatedness between polypeptides as determined by the match between strings of such sequences. "Identity" and "similarity" can be readily calculated by known methods, including, but not limited to, those described in Computational Molecular Biology, Lesk, A. M., Ed., Oxford University Press, N Y, 1988; Biocomputing: Informatics and Genome Projects, Smith, D. W., Ed., Academic Press, N Y, 1993; Computer Analysis of Sequence Data, Part I, Griffin, A. M. & and Griffin, H. G., Eds., Humana Press, N J, 1994; Sequence Analysis in Molecular Biology, von Heinje, G., Academic Press, 1987; Sequence Analysis Primer, Gribskov, M. & Devereux, J., Eds., M Stockton Press, N Y, 1991; and Carillo & Lipman (1988) *SIAM J. Applied Math.,* 48: 1073.

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison, Wis.) that incorporates the Needelman & Wunsch ((1970) *J. Mol. Biol.*, 48: 443-453) algorithm (e.g., NBLAST and XBLAST). The default parameters are used to determine the identity for the polypeptides of the present disclosure.

The term "isolated" as used herein refers to material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material includes material in native and recombinant form.

The term "liposome" as used herein refers to a spherical lipid and phospholipid particle in which individual lipid molecules cooperatively interact to create a bipolar lipid membrane that encloses and isolates a portion of the medium in which it was formed. A liposome may further encompass structures that envelop or encapsulate a probe according to the disclosure for delivery to a recipient human or non-human animal subject, whereupon the siRNA of the disclosure may be released from the liposome. It is further contemplated that the liposomes of the disclosure may optionally include polyethylene glycol moieties attached thereto.

The term "modify the level of gene expression" as used herein refers to generating a change, either a decrease or an increase in the amount of a transcriptional or translational product of a gene. The transcriptional product of a gene is herein intended to refer to a messenger RNA (mRNA) transcribed product of a gene and may be either a pre- or post-spliced mRNA. Alternatively, the term "modify the level of gene expression" may refer to a change in the amount of a protein, polypeptide or peptide generated by a cell as a consequence of interaction of an siRNA with the contents of a cell. For example, but not limiting, the amount of a polypeptide derived from a gene may be reduced if the corresponding mRNA species is subject to degradation as a result of association with an siRNA introduced into the cell.

The term "modulate" refers to the activity of a composition to affect (e.g., to promote or retard) an aspect of cellular function, including, but not limited to, cell growth, proliferation, apoptosis, and the like.

The term "nucleic acid sequence," encompass a polynucleotide. A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone.

The term "oligonucleotide" as used herein refers to a series of linked nucleotide residues. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use. The term "pharmaceutically acceptable carrier" as used herein refers to a medium which does not interfere with the effectiveness or activity of an active ingredient and which is not toxic to the hosts to which it is administered.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "primer" as used herein refers to an oligonucleotide complementary to a DNA segment to be amplified or replicated. Typically primers are used in PCR. A primer hybridizes with (or "anneals" to) the template DNA and is used by the polymerase enzyme as the starting point for the replication/amplification process. By "complementary" it is meant that the primer sequence can form a stable hydrogen bond complex with the template.

The term "short interfering RNA" as used herein means a nucleic acid sequence that mediates the cleavage of a target gene transcript. Short interfering RNAs (siRNAs) may be double stranded or of the short hairpin type. Double stranded siRNAs may be comprised of two individual, antiparallel, annealed RNA strands or annealed nucleic acid strands which contain both RNA and DNA (e.g. 5'-TTTTUUUU-3' annealed to 5'-TTTTUUUU-3' or 5'-TTTT-3' annealed to 5'-UUUU-3'). siRNAs of the short hairpin type may be comprised of a single RNA strand or a single RNA:DNA hybrid strand capable of forming a stem-and-loop structure or other secondary structure effective as an siRNA. Those skilled in the art will recognize that siRNAs may comprise other modifications such as nucleoside analogs, backbone modifications, and other modifications that still permit the modified siRNA nucleic acid to mediate the cleavage of a target gene transcript.

siRNA may be divided into five (5) groups (non-functional, semi-functional, functional, highly functional, and hyper-functional) based on the level or degree of gene silencing that they induce in cultured cell lines. As used herein, these definitions are based on a set of conditions where the siRNA is transfected into said cell line at a concentration of 100 nM and the level of silencing is tested at a time of roughly 24 hours after transfection, and not exceeding 72 hours after transfection. In this context, "non-functional siRNA" are defined as those siRNA that induce less than 50% (<50%) target silencing. "Semi-functional siRNA" induce 50-79% target silencing. "Functional siRNA" are molecules that induce 80-95% gene silencing. "Highly-functional siRNA" are molecules that induce greater than 95% gene silencing. "Hyperfunctional siRNA" are a special class of molecules. For purposes of this document, hyperfunctional siRNA are defined as those molecules that: (1) induce greater than 95% silencing of a specific target when they are transfected at subnanomolar concentrations (i.e., less than one nanomolar); and/or (2) induce functional (or better) levels of silencing for greater than 96 hours. These relative functionalities (though not intended to be absolutes) may be used to compare siRNAs to a particular target for applications such as functional genomics, target identification and therapeutics.

The term "similarity" as used herein refers to the exact amino acid to amino acid comparison of two or more polypeptides at the appropriate place, where amino acids are identical or possess similar chemical and/or physical properties such as charge or hydrophobicity. A "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

The primers herein are selected to be "substantially" complementary to different strands of a target DNA sequence, but they need not reflect the exact sequence of the template. For example, a non-complementary nucleotide fragment may be attached to the 5' end of the primer or, alternatively, non-complementary bases can be interspersed into a primer, as long as there are sufficient complementary bases to hybridize the primer and to initiate extension.

The term "subject" as used herein refers to humans, other mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, and especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals, particularly pets such as dogs and cats. For diagnostic or research applications, a wide variety of mammals will be suitable subjects, including rodents (e.g., mice, rats, hamsters), rabbits, primates, and swine such as inbred pigs and the like.

The phrase "substantially similar" refers to a similarity of at least 90% with respect to the identity of the bases of the sequence.

The term "therapeutic effect" as used herein refers to an effect of a composition of the disclosure, in particular a formulation or dosage form, or method disclosed herein. A therapeutic effect may be a sustained therapeutic effect that correlates with a continuous concentration of a compound of the disclosure over a dosing period, in particular a sustained dosing period. A therapeutic effect may be a statistically significant effect in terms of statistical analysis of an effect of a compound of the disclosure versus the effects without the compound.

The term "therapeutically effective amount" relates to the amount or dose of an active compound of the disclosure or composition comprising the same that will lead to one or more desired effects, in particular, one or more therapeutic effects or beneficial pharmacokinetic profiles. A therapeutically effective amount of a substance can vary according to factors such as the disease state, age, sex, and weight of the subject, and the ability of the substance to elicit a desired response in the subject. A dosage regimen may be adjusted to provide the optimum therapeutic response or pharmacokinetic profile. For example, several divided doses may be administered daily or the dose may be proportionally reduced as indicated by the exigencies of the therapeutic situation.

The terms "treat" or "treatment" as used herein refer to both therapeutic treatment and prophylactic or preventative measures, where the object is to prevent or slow down (lessen) an undesired physiological change or disorder resulting from a seizure including, but not limited to, cellular apoptosis or cell death, and especially, but not limited to, a reduction in the viability of a neural cell. Beneficial or desired clinical results include, but are not limited to, alleviation of symptoms, diminishment of the extent of disease, stabilized (i.e., not worsening) state of disease, and delay or slowing of progression of the symptoms recognized as originating from a stroke. The term "treatment" can also refer to prolonging survival as compared to expected survival if not receiving treatment. Those in need of treatment include those already with the condition or disorder as well as those prone to have the condition or disorder or those in which the condition or disorder is to be prevented or onset delayed.

Description

The present disclosure provides compositions and methods of use thereof that modulate the activity of C/EBP homologous stress-related protein (Chop) in Myeloid-derived Suppressor Cells (MDSCs). The novel data of the disclosure indicate that Chop is a key point in the response of MDSCs to tumor-generated stress factors. In turn, the MDSCs release cytokines and other factors that function as immune suppressors, thereby allowing the tumors to thrive and expand. Additionally, the MDSCs release angiogenic factors that lead to an increase in tumor vascularization, nourishing the tumor mass and facilitating metastasis.

The central role played by Chops in MDSC response to tumors provides a potential focus for regulation of the interaction between MDSCs and tumors. Most advantageously, by inhibiting the level of Chop activity, the immunosuppressive function of MDSCs is disrupted. It has also been unexpectedly found that there is a concomitant increase in the ability of MDSCs to act as antigen-presenting cells so as to act in increasing the efficacy of anti-tumor immune-based therapies.

One especially advantageous method of reducing the activity of Chop in MDSCs has now been found to be the introduction into MDSCs of small-interfering RNAs (siRNA) that can reduce the expression of the Chop protein. The disclosure, therefore, encompasses a composition that comprises an siRNA that is effective in reducing the level of Chop expression by a recipient cell (gene-silencing). It has been found that such an agent may be delivered to the interior (cytoplasm) of MDSCs by enclosing the siRNA in a vehicle such as, but not limited to, a liposome, and most advantageously in a pegylated liposome. It is contemplated that it is within the scope of the present disclosure for other vehicles well-known in the art to be used for delivery of an siRNA to a MDSCs. For example, but not intended to be limiting, a pegylated liposome may further include a targeting moiety that specifically targets MDSCs and therefore, when delivered to a recipient subject intravenously, will allow the vehicle/siRNA composition to be substantially delivered to MDSCs and not to other cells in the subject. Suitable targeting moieties may include, for example, liposome-bound cell-surface receptor ligands, most advantageously ligands of MDSC-specific receptors.

The disclosure further encompasses the use of such Chop-directed agents to reduce the level of Chop activity in MDSCs. For example, it is intended that the compositions of the disclosure may be delivered to MDSCs that have been removed from a subject, contacted with a pharmaceutically acceptable composition comprising such as liposomes carrying anti-Chop siRNAs, allowing the liposomes to deliver the siRNA to the cytoplasm of the cells to inhibit the expression of the Chop protein. It is contemplated that such treated cells may be substantially purified before treatment, and also may be returned to the parent animal or human subject whereupon they may circulate to a tumor and facilitate an anti-tumor response.

It is further contemplated that the Chop activity-regulating agent such as an siRNA of the disclosure may be included in a pharmaceutically acceptable composition that further comprises a pharmaceutically acceptable carrier so that the agent may be administered to an animal or human subject for delivery to the site of a tumor. It is within the scope of the disclosure for such compositions to be delivered systemically such as by an intravenous route, whereby the vehicle/agent composition is generally dispersed throughout the subject's body but the anti-Chop agent is effective only in those cells expressing Chop, such as MDSCs. General dispersion may be limited by including with the vehicle an MDSC-targeting moiety that allows concentration of the vehicle/agent in MDSCs. Also advantageous is the direct delivery of the vehicle/agent compositions to a tumor by such means as injection into the tumor mass or by injection into a blood vessel leading into a tumor mass. However, it should be considered within the scope of the disclosure to deliver the compositions of the disclosure by any route that is advantageous to the recipient subject and which allows an effective amount of the anti-Chop agent to enter into and suppress the activity of Chop.

Further encompassed by the disclosure is a method of increasing the efficacy of immune-based therapies, and most advantageously T cell-based therapies that are directed against tumors. It has been found that reducing or eliminating the Chop activity of MDSCs increases the proliferation of T cells and promotes T cell anti-tumor activity. Accordingly, one aspect of the disclosure is a method of enhancing an anti-tumor therapy by eliminating Chop activity in tumor-associated MDSCs while increasing the population of T-cells directed against said tumor.

Sensing and responding to microenvironment stress signals are fundamental for the survival and growth of tumor cells. However, the major mediators of the stress response, and the effect of these mediators, on anti-tumor immunity remain unknown. Results described herein identify C/EBP homologous stress-related protein (Chop) as a master regulator of Myeloid-derived Suppressor Cell (MDSC) function. Therefore the inhibition of Chop or the upstream pathways that activate and sustain its expression are attractive targets for reducing or inhibiting MDSC-mediated immunosuppression. Supporting the notion of Chop as a master MDSC regulator and therapeutic target, data demonstrate that deletion of Chop in stroma delayed tumor growth, restored protective anti-tumor T cell responses, blocked MDSC-suppressive pathways, and switched MDSC into myeloid cells with the ability to prime T cells. Equally important is the knowledge that suppressing transcription factors such as Atf4, which in turn binds and activates Chop can also be a novel approach to blocking the accumulation of MDSC, or preventing the development of their immunosuppressive function. Most generally, the compositions and methods of the present disclosure may be usefully applied for the treatment of various diseases or disorders by inhibiting or reducing MDSC immunosuppression. It is also contemplated that embodiments of the aspects of the disclosure may be most advantageously used in the treatment of various cancers, including, but certainly not limited to, cancers of the breast, lung, colon, skin, and metastatic cancers.

MDSCs accumulate as a result of stress factors released in a microenvironment due to various conditions such as cancer, infections, and autoimmune disease, all of which are linked with chronic inflammation. For example, a link between inflammation, high numbers of MDSC, and immune suppression has been made in chronic infectious diseases, sepsis, trauma, and autoimmunity.

The compositions and methods of the present disclosure are advantageous, therefore, to reduce or inhibit MDSC-associated immunosuppression by inhibiting or reducing Chop. These methods include, but certainly are not limited to, genetic approaches such as siRNA or anti-sense oligonucleotides delivered by such vehicles as such as pegylated liposomes. By reducing Chop activity, it is now shown to be possible to promote protective responses, such as T cell responses.

Chop is regulated by various upstream factors, such as eIF2α and the activating transcription factor 4 (ATF4). Inhibition of such factors upstream of Chop may prevent the induction and/or activation of Chop and reduce or inhibit MDSC-associated immunosuppression. Similarly, inhibition of factors downstream of Chop may also mediate the suppressive activity of MDSC. Thus, embodiments of the present disclosure may also comprise the inhibition or activation of factors upstream or downstream of Chop.

MDSC are also known to "protect" tumors from their anti-tumor effect. The mechanisms of this are poorly understood, however depletion of MDSC from a mouse by using an anti-GR1 antibody increases the efficacy of standard chemotherapeutic agents and radiation therapy. Therefore, inhibition of Chop or Atf4, which will lead to inhibition of the suppressive function of MDSC, can then result in an increased therapeutic activity of chemotherapy and radiation therapy.

Figure 12A:
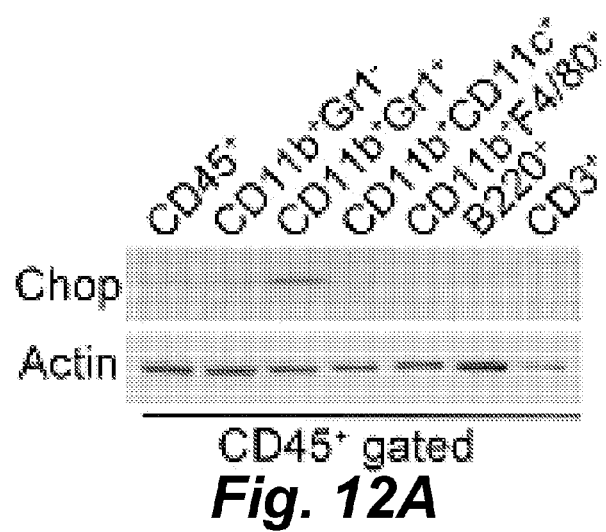
FIGS. 12A-12D illustrate that stromal Chop deletion delays tumor progression in a MDSC-dependent manner.
Figure 12B:
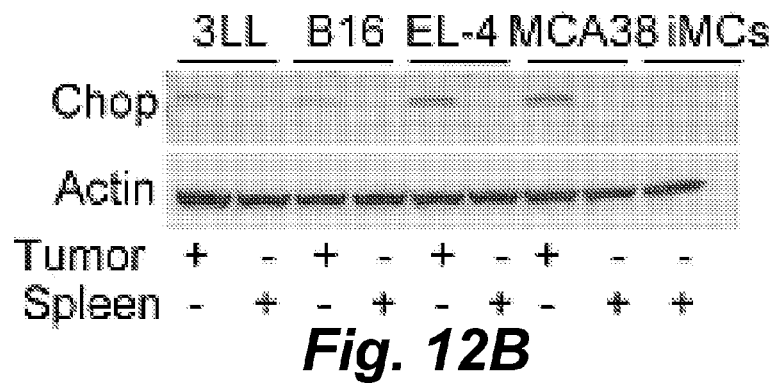

Expression of Chop in Tumor-Infiltrating MDSCs Regulates Tumor Growth:

The expression of Chop in spleens and tumors from mice s.c. injected with 3LL lung carcinoma was examined. An increased expression of Chop was found at the tumor site, compared to the spleen, and was shared by the malignant cells and infiltrating CD45$^+$ leukocytes. To identify the distribution of Chop among the tumor-linked leukocytes, CD45$^+$ populations from 3LL tumors were sorted and monitored for their expression of Chop. Higher amounts of Chop were found in MDSCs (CD11b$^+$Gr1$^+$) compared to other cell populations, including CD11b$^+$Gr1$^+$ myeloid cells, CD11b$^+$CD11c$^+$ dendritic cells, CD11b$^+$F4/80$^+$ macrophages, B220$^+$ B lymphocytes or pDCs, and CD3$^+$ T cells, as shown in FIG. 12A. The increased expression of Chop in tumor-linked MDSCs, compared to splenic MDSCs or immature myeloid cells (iMCs) was validated in different tumor models, including 3LL, B16 (melanoma), EL-4 (thymoma), and MCA-38 (colon carcinoma) (FIG. 12B), and correlated with the MDSC ability to block T cell proliferation.

Figure 12C:
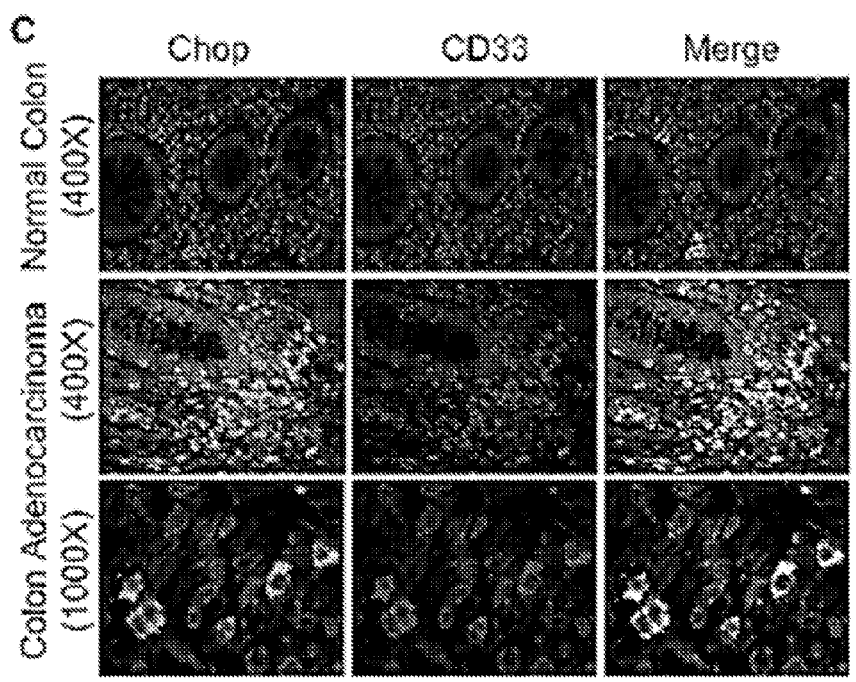

Whether human MDSCs infiltrating tumors displayed an increased expression of Chop was tested. Using a panel of colon carcinoma samples, preferential Chop up-regulation in CD33$^+$ myeloid cells was found in minimal numbers in normal colon tissues, as shown in FIG. 12C. In addition, Chop expression in colon tumors was restricted to CD66b$^+$ HLA-DR populations, demonstrating the expression of Chop in human MDSCs.

Figure 12D:
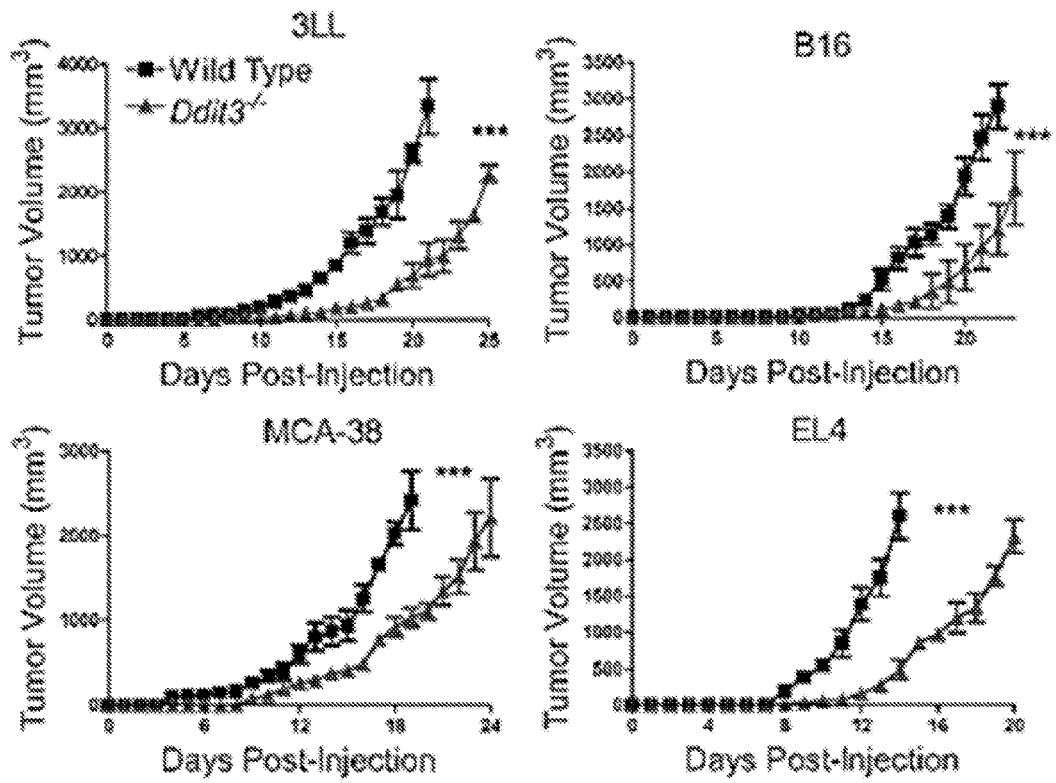

To determine the effect of stromal Chop in tumor growth, C57BL/6 controls and Chop-deficient mice (referred hereinafter as Ddit3$^{-/-}$) were injected s.c. with different tumors carrying functional Chop, after which tumor growth kinetics and survival were monitored. In all tested tumor models, a decreased tumor growth (FIG. 12D) and an extended survival were seen in Ddit3$^{-/-}$ mice, compared to wild-type controls. In addition, increased tumor cell necrosis and decreased angiogenesis were observed in tumors from Ddit3$^{-/-}$ mice. Because MDSCs were the major source of Chop in the tumor stroma, their role in the antitumor effects found in Ddit3$^{-/-}$ mice was established using a bone marrow (BM) chimeric model as described by Loinard et al., (2012) *Circulation* 125: 1014-1026. In brief, lethally irradiated CD45.1$^+$ mice were reconstituted with BM cells isolated from CD45.2$^+$Ddit3$^{-/-}$ mice or controls.

Additionally, lethally irradiated CD45.2$^+$Ddit3$^{-/-}$ mice were transplanted with CD45.1$^+$ wild-type BM cells. Greater than 90% chimerism and equal numbers of CD11b$^+$ Gr1$^+$ cells were found in all conditions 7 weeks after transplant. A similar delay in tumor growth was found in Ddit3$^{-/-}$ BM chimeric mice and systemic Ddit3$^{-/-}$ mice, as compared to controls. In addition, reconstitution of Ddit3$^{-/-}$ mice with wild-type BM resulted in a similar tumor growth as that observed in wild-type controls, suggesting the key role of MDSC-linked Chop in tumor growth.

To further demonstrate the role of MDSCs in the antitumor effects found in Ddit3$^{-/-}$ mice, MDSCs were depleted by treatment with anti-Gr1 antibodies as described by Mundy-Bosse et al., (2011) *Cancer Res.* 71: 5101-110. Pharmacological depletion of MDSCs induced antitumor effects in wild-type mice, while it resulted in a partial recovery of tumor growth in 3LL-bearing Ddit3$^{-/-}$ mice, suggesting a functional difference between MDSCs from tumor-bearing wild-type and Ddit3$^{-/-}$ mice. Thus, the results suggest that tumor MDSCs display a preferential increased expression of Chop and that deletion of Chop induced antitumor effects in a MDSC-dependent manner.

Chop Regulates the Proliferation, Turnover, and Immune-Inhibitory Activity of MDSCs:

The impact of Chop in the accumulation, turnover, and immune inhibitory function of MDSCs was tested. Similar percentages of MDSCs were found in the spleen and BM of wild-type and Ddit3$^{-/-}$ mice both with and without tumors. In contrast, an elevated percentage of MDSCs was detected in tumors from Ddit3$^{-/-}$ mice, compared to controls, with both G-MDSCs and M-MDSCs showing increases. The accumulation of tumor MDSCs in Ddit3$^{-/-}$ mice did not extend to other myeloid populations, such as DCs (CD11b$^+$ Gr1$^-$CD11c$^+$) and macrophages (CD11b$^+$Gr1$^-$F4/80$^+$).

To test the specific role of Chop in MDSC accumulation in tumors, BM MDSCs were harvested from 3LL-bearing wild-type and Ddit3$^{-/-}$ mice, labeled with high and low concentrations of CFSE, mixed in a 1:1 ratio, and adoptively transferred into wild-type mice bearing 3LL cells. At 24 h after transfer, similar amounts of transferred wild-type and Ddit3$^{-/-}$ MDSCs in spleen were found, while higher numbers of Ddit3$^{-/-}$ MDSCs were noted in tumors.

To further understand the increased accumulation of Ddit3$^{-/-}$ MDSCs in tumors, the effect of Chop in the proliferation and decay of MDSCs was investigated. A similar proliferation of spleen and bone marrow MDSCs was found in wild-type and Ddit3$^{-/-}$ mice, as tested by BrdU uptake but an elevated tumor MDSC proliferation was noted in Ddit3$^{-/-}$ mice compared to controls. Decreased expression of the apoptosis markers annexin V and cleaved caspase 3 were detected in tumor MDSCs from Ddit3$^{-/-}$ mice, compared to wild-type MDSCs. Thus, Chop deletion increased proliferation and reduced turnover of tumor MDSCs.

Figure 13A:
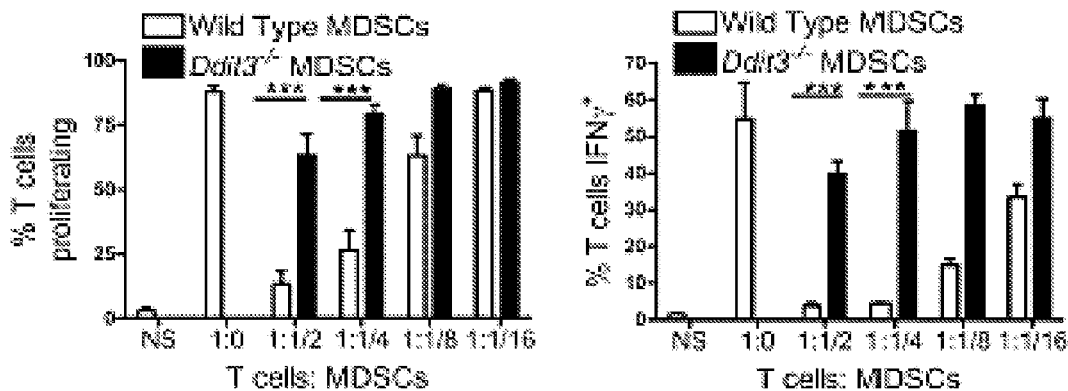
FIGS. 13A-13D illustrate that Chop deletion in MDSCs decreases turnover, increases proliferation, and blocks immune tolerogenic function.
Figure 13B:
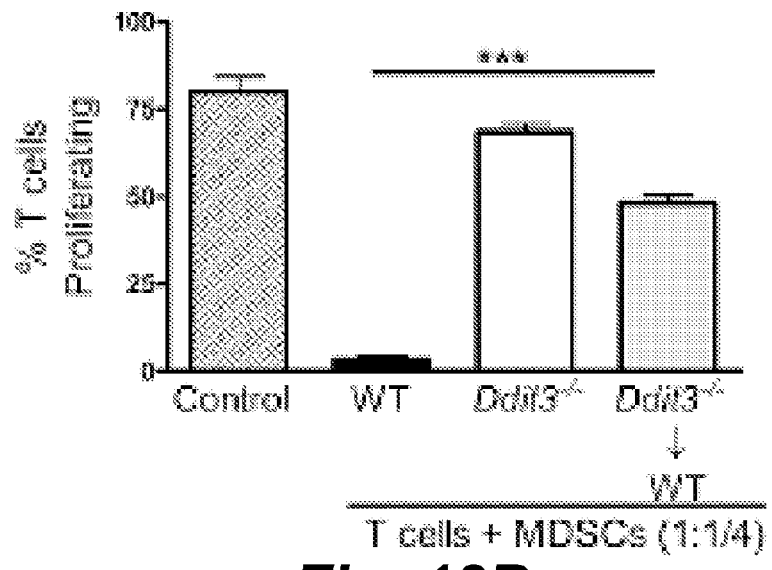
Figure 13C:
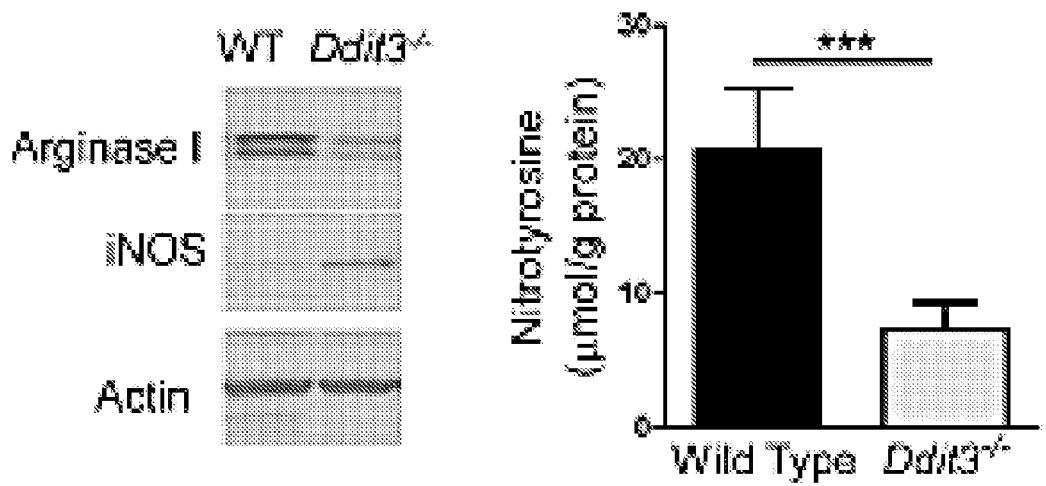
Figure 13C:
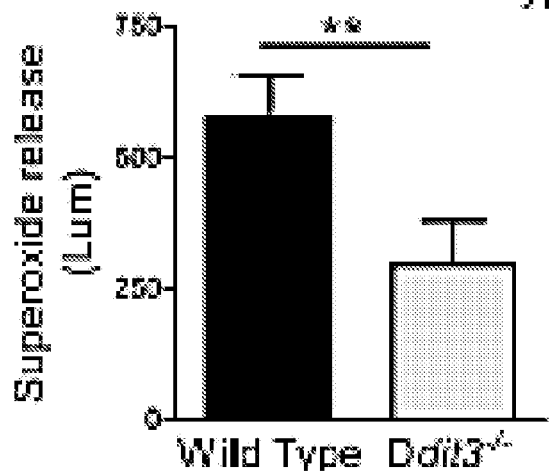

Whether Chop deletion affected the immune-inhibitory ability of MDSCs was examined. Tumor-sorted MDSCs from Ddit3$^{-/-}$ mice had a reduced capacity to block activated T cell proliferation and IFN-γ production, as compared to those from control mice (FIG. 13A). A similar decreased inhibitory function was also detected in MDSCs from tumor-bearing Ddit3$^{-/-}$ BM chimeras (FIG. 13B). The low regulatory potential of Ddit3$^{-/-}$ MDSCs correlated with an impaired synthesis of major molecules linked to MDSC activity, including arginase I, PNT, and superoxide, but an increased iNOS expression (FIG. 13C).

Figure 13D:
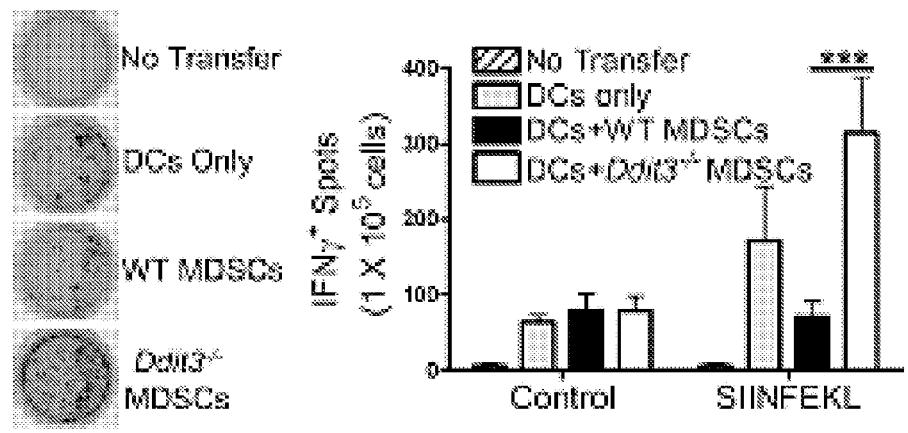

To test the role of Chop in the tolerogenic activity of MDSCs in vivo, CD45.2$^+$ anti-OVA$_{257-264}$ (SIINFEKL) transgenic CD8$^+$ OT-I cells were adoptively transferred into CD45.1$^+$ mice, followed by immunization with wild-type DCs loaded with SIINFEKL. Tumor MDSCs from wild-type or Ddit3$^{-/-}$ mice pulsed with SIINFEKL were transferred the same day as immunization, as well as 5 days later. Transferred MDSCs had a similar low contamination with CD11c$^+$ DCs and F4/80$^+$ macrophages. At 12 days after vaccination, lymph nodes were harvested, challenged with SIINFEKL, and tested for IFN-γ production by Elispot. A significant decrease in the production of IFN-γ was found in mice transferred with SIINFEKL-loaded DCs and wild-type MDSCs (FIG. 13D). Conversely, transfer of Ddit3$^{-/-}$ MDSCs further enhanced the numbers of IFN-γ$^+$ cells induced by the SIINFEKL-DCs vaccine, suggesting that Chop deletion not only blocked the tolerogenic activity of MDSCs, but also allowed MDSCs to increase T cell function.

Figure 14A:
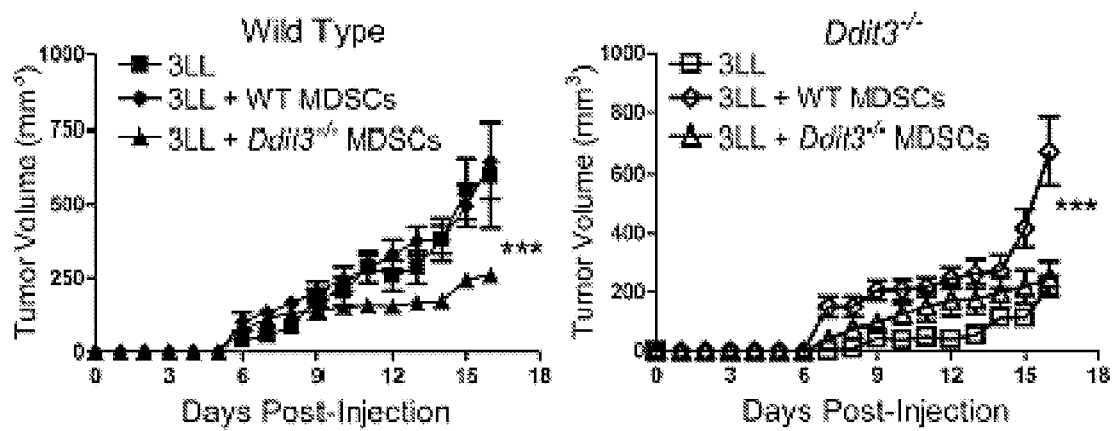
FIGS. 14A-14D illustrate that Chop-deficient MDSCs delay tumor growth and promote T cell function.

Chop-Deficient MDSCs Induce Antitumor Responses and Prime T-Cell Proliferation:

3LL cells were mixed 1:1 with MDSCs isolated from wild-type or Ddit3$^{-/-}$ mice bearing 3LL tumors and injected s.c. into wild-type or Ddit3$^{-/-}$ mice. Coinjection of Ddit3$^{-/-}$ MDSCs into wild-type mice significantly delayed tumor growth, whereas coinjection of wild-type MDSCs into Ddit3$^{-/-}$ mice partially restored tumor growth (FIG. 14A).

Figure 14B:
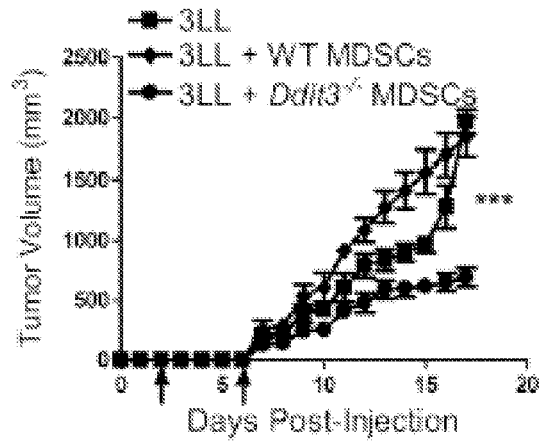
Figure 14C:
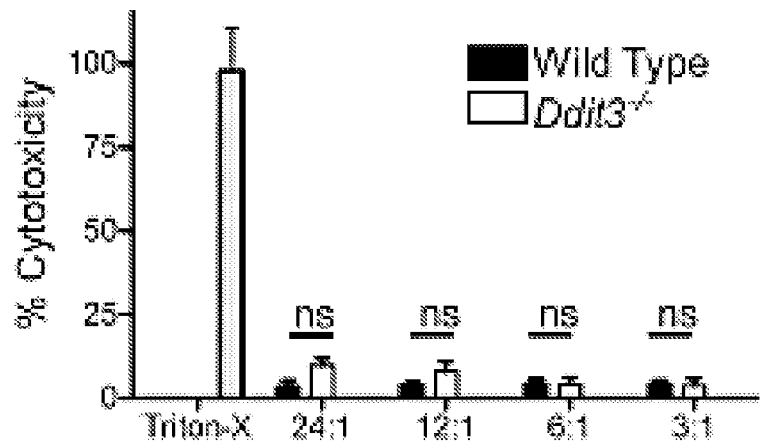

The therapeutic effect of Ddit3$^{-/-}$ MDSCs in established tumors was evaluated. Adoptive transfer of Ddit3$^{-/-}$ MDSCs after 3 and 6 days of 3LL injection delayed tumor growth, while transfer of wild-type MDSCs accelerated 3LL growth (FIG. 14B). A low antitumor cytotoxicity was displayed by wild-type and Ddit3$^{-/-}$ MDSCs (FIG. 14C), ruling out a direct antitumor effect of Ddit3$^{-/-}$ MDSCs.

Figure 7A:
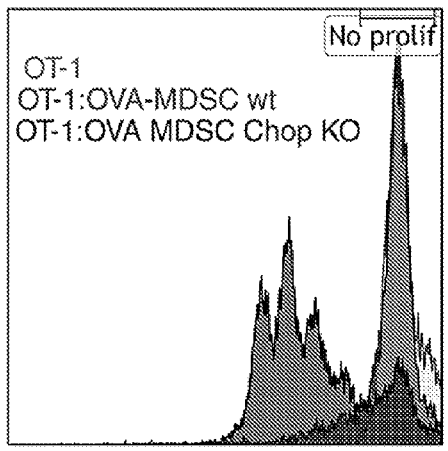
FIG. 7A illustrates that Chop KO MDSC-primed antigen-specific T cells.
Figure 7B:
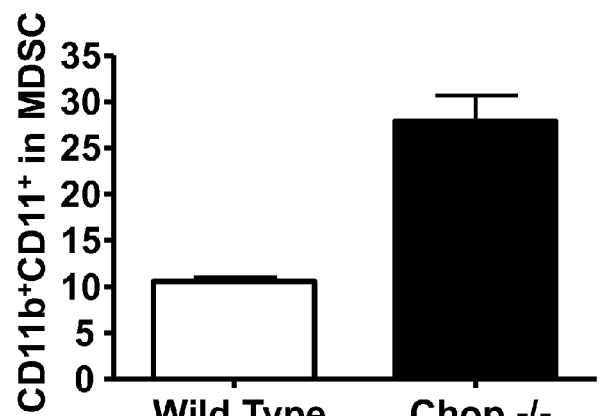
FIG. 7B illustrates that Chop KO MDSC-primed antigen-specific T cells had a higher expression of CD11c.
Figure 7C:
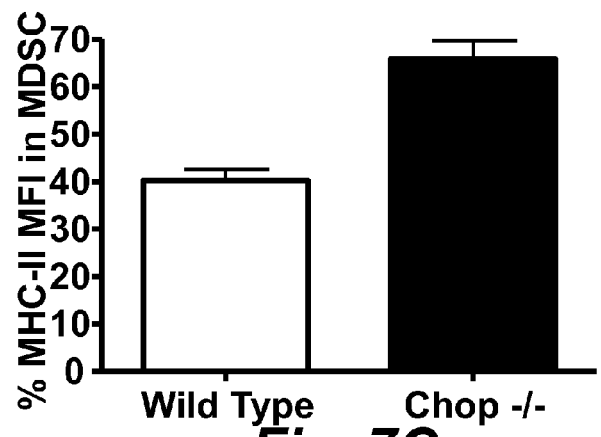
FIG. 7C illustrates that Chop KO MDSC-primed antigen-specific T cells had a higher expression of MHC II.
Figure 7D:
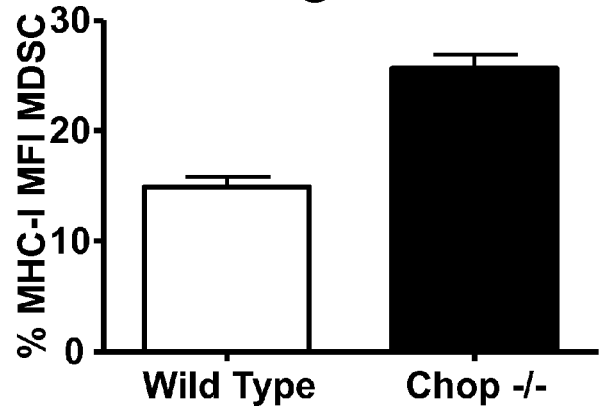
FIG. 7D illustrates that Chop KO MDSC-primed antigen-specific T cells had a higher expression of MHC I.
Figure 14D:
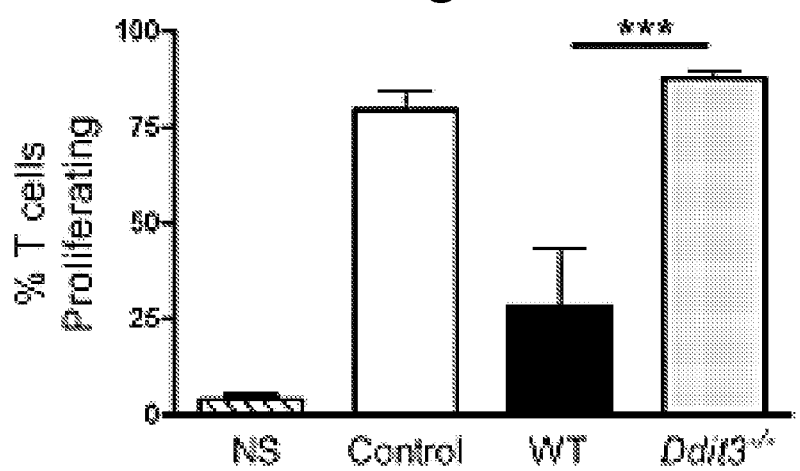

Whether Chop deletion allowed MDSCs to prime T cell responses was also tested. Thus, MDSCs were sorted from wild-type and Ddit3$^{-/-}$ mice bearing 3LL tumors, after which they were loaded with SIINFEKL, washed, and co-cultured with CFSE-labeled naive OT-I cells. A higher proliferation was observed in OT-I cells co-cultured with Ddit3$^{-/-}$ MDSCs, compared to those co-cultured with wild-type MDSCs (FIG. 14D), suggesting that Chop deletion enabled MDSCs to induce T cell proliferation. Ddit3$^{-/-}$ MDSCs displayed a higher expression of major histocompatibility complex (MHC) class I and II (FIGS. 7C and 7D). Thus, Chop-deficient MDSCs induced antitumor effects and had the ability to activate T cell responses.

Figure 15A:
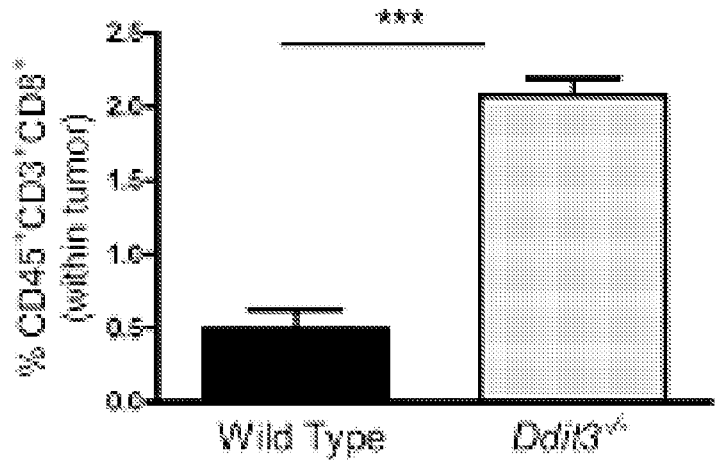
FIGS. 15A-15C illustrate that Chop deletion overcomes tumor-induced T-Cell tolerance and enhances T cell immunotherapy.
Figure 15B:
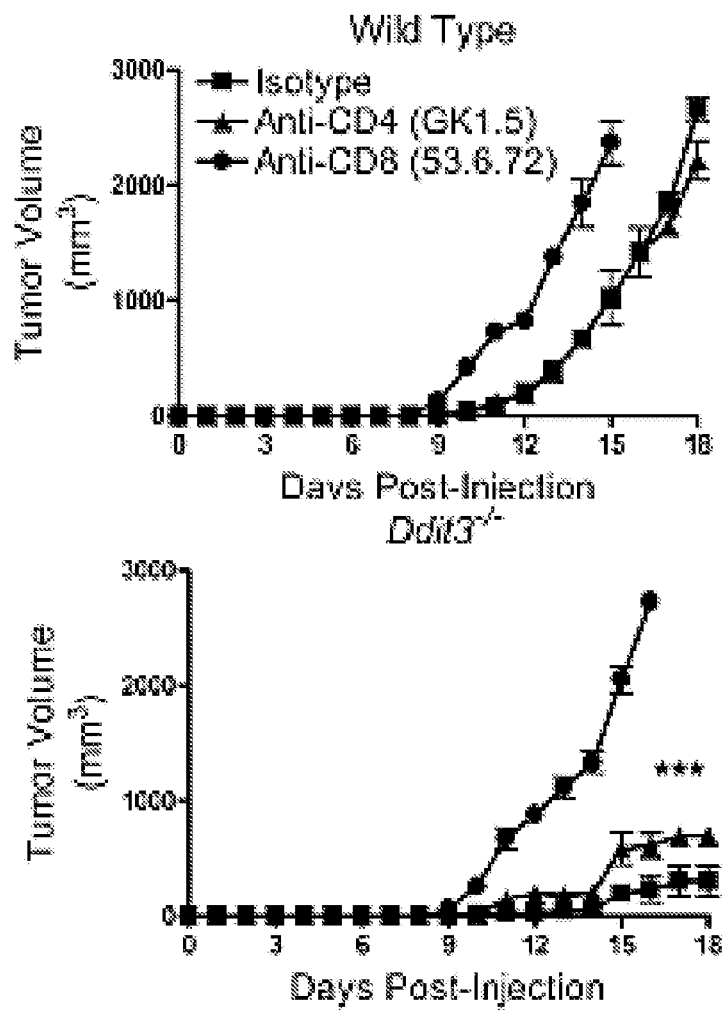
Figure 15C:
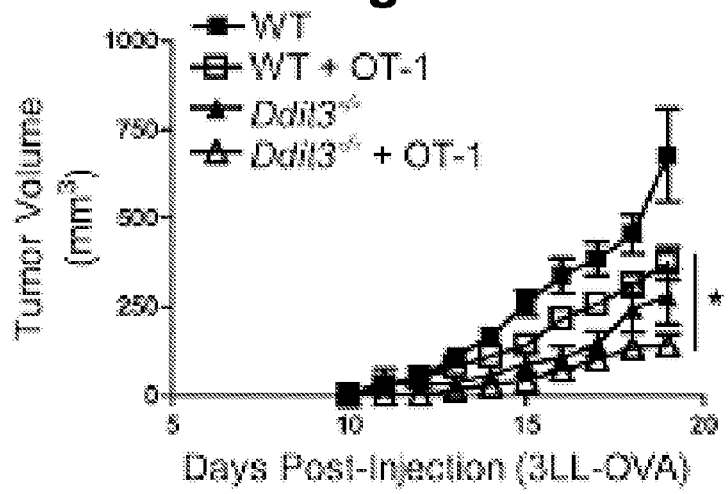

Chop in MDSCs is a Central Mediator of Tumor-Induced Tolerance:

Whether the deletion of stromal Chop impacted the suppression of T cell responses in tumors was determined. Tumor-bearing Ddit3$^{-/-}$ mice showed an increased infiltration of CD45$^+$ cells and CD8$^+$ T cells in the tumors (FIG. 15A) and an elevated number of CD8$^+$ T cells producing IFN-γ after activation (FIG. 15C). Furthermore, a partial recovery of CD3ζ chain expression, a key protein for T cell activation, was observed in T cells from 3LL-bearing Ddit3$^{-/-}$ mice, compared to those from controls with tumors.

Although T cells infiltrating tumors were negative for Chop expression (FIG. 12A), their effect as mediators of the antitumor responses found in Ddit3$^{-/-}$ mice was tested. Depletion of CD8$^+$ T cells, but not CD4$^+$ T cells, restored tumor growth in 3LL-bearing Ddit3$^{-/-}$ mice (FIG. 15B), indicating a role of CD8$^+$ T cells in the antitumor responses induced by Chop deletion.

To address the role of Chop in tumor-induced tolerance, wild-type and Ddit3$^{-/-}$ mice (CD45.2$^+$) were injected s.c. with 3LL tumors expressing the model tumor antigen ovalbumin (OVA). Seven days later, 5×10$^6$ CD45.1$^+$CD8$^+$ OT-I cells were adoptively transferred into the mice, followed by vaccination with SIINFEKL. A higher antitumor effect was noted in Ddit3$^{-/-}$ mice receiving OT-I cells, as compared to wild-type controls transferred with the same number of T cells (FIG. 15C). In addition, elevated numbers of T cells producing IFN-γ were detected in the spleens of vaccinated tumor-bearing Ddit3$^{-/-}$ mice after activation ex vivo with SIINFEKL, which correlated with a higher total yield of transferred CD45.1$^+$ OT-I cells in both the spleens and tumors.

Because these results could be explained by a low suppression driven by the smaller tumors observed in Ddit3$^{-/-}$ mice, the experiment was repeated in wild-type and Ddit3$^{-/-}$ mice bearing similar sized 3LL-OVA tumors (approximately 100 mm$^3$, day 8 for wild-type and day 15 for Ddit3$^{-/-}$ mice). An increased production of IFN-γ$^+$ after SIINFEKL activation and higher numbers of CD45.1$^+$ OT-I T cells in the spleens and tumors were detected in tumor-bearing Ddit3$^{-/-}$ mice, compared to controls, indicating a role of Chop in tumor-induced tolerance and the potential benefit of its deletion for T cell-based immunotherapy.

Mediators of Chop Expression in MDSCs:

The role of the tumor environment in the induction of Chop in MDSCs and the effect of Chop in the promotion of MDSC function by tumors was investigated. BM MDSCs were treated with 3LL tumor explant supernatants (TES), after which MDSCs were tested for the induction of Chop and the ability to block T cell proliferation. TES treatment induced Chop expression in MDSCs and increased MDSC regulatory activity.

Figure 16A:
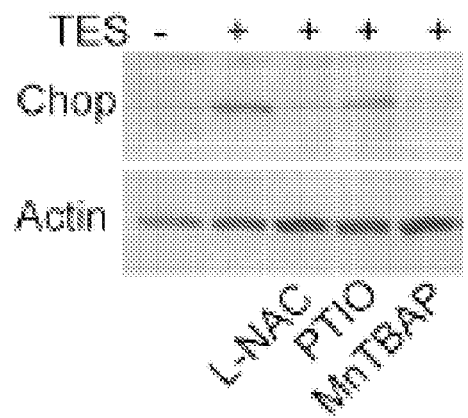
FIGS. 16A-16E illustrate that tumor-derived stress factors trigger Chop expression in MDSCs.

Ddit3$^{-/-}$ BM MDSCs failed to increase inhibitory function after TES treatment, suggesting the role of Chop in the regulation of MDSC function by tumors. To identify the major mediators leading to the expression of Chop in MDSCs, the effects of ROS and PNT were tested. Higher amounts of PNT and ROS were found in tumors, compared to spleens of 3LL-bearing mice and controls, and in tumor MDSCs compared to spleen MDSCs and iMCs. In addition, treatment of BM MDSCs with PNT, and to a lesser extent with H$_2$O$_2$, led to a similar induction of Chop as that induced by TES. In agreement with these data, inhibition of Chop up-regulation was noted in TES-treated BM MDSCs after the addition of the antioxidant N-acetyl cysteine (L-NAC) and PNT scavenger MNTBAP, but not nitric oxide scavenger PTIO (FIG. 16A).

Figure 16B:
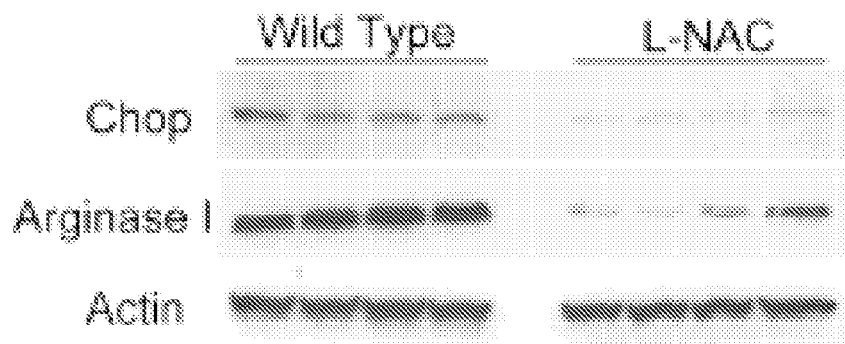
Figure 16C:
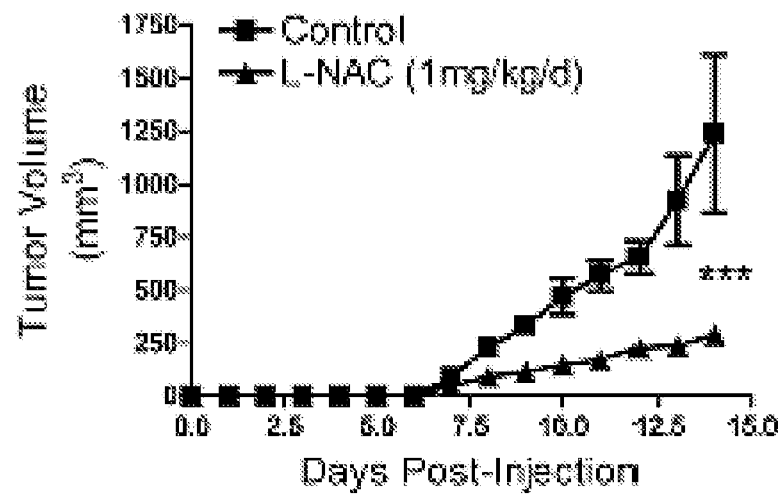
Figure 16D:
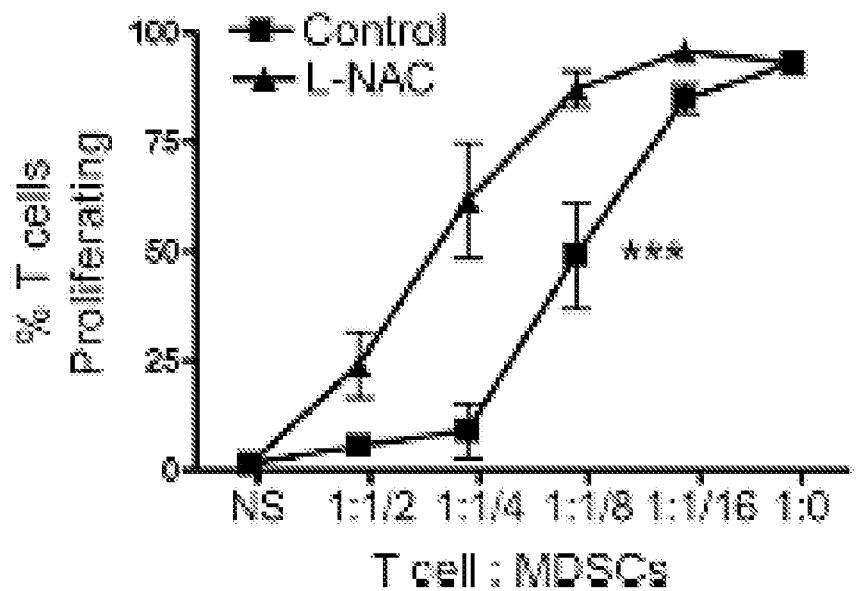

Furthermore, treatment of tumor-bearing mice with L-NAC resulted in a lower expression of Chop in tumor MDSCs (FIG. 16B) and a similar effect as that induced by Chop deletion, including a delayed tumor growth (FIG. 16C), an impaired MDSC inhibitory function (FIG. 16D), and reduced levels of arginase I (FIG. 16B).

Figure 16E:
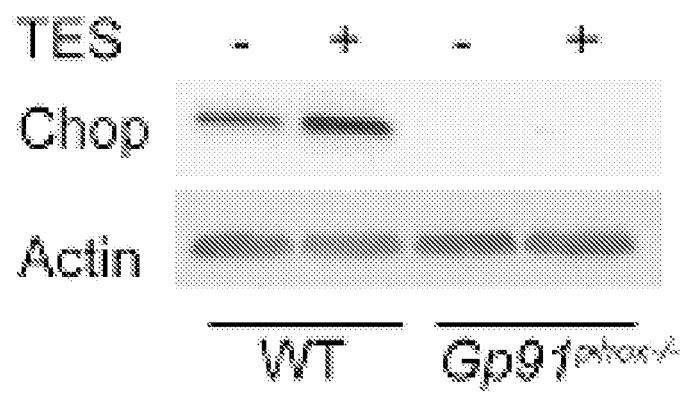

Because MDSCs were a major source of PNT in tumors, it was determined whether the endogenous production of ROS or PNT in MDSCs modulated Chop. Deletion of Gp91$^{phox}$, a key component in the production of ROS and PNT by MDSCs blocked Chop up-regulation in TES-treated BM MDSCs (FIG. 16E), suggesting the endogenous role of ROS or PNT in MDSCs in the induction of Chop by tumors.

Chop Expression in MDSCs is Mediated by Atf4:

ISRs are characterized by the expression of phospho-eIF2α and signaling through Atf4 protein. Accordingly, the role of ISR in the induction of Chop in MDSCs was determined. Increased expression of phospho-eIF2α and Atf4 were noted in MDSCs from tumors and TES-treated BM MDSCs. Furthermore, the elevated expression of Chop in tumor-linked MDSCs correlated with a higher endogenous binding of Atf4 to Chop promoter, as tested by ChIP assays.

To confirm the role of Atf4 in the induction of Chop in MDSCs from tumors, Atf4$^{+/-}$ mice were used, because Atf4$^{-/-}$ mice showed low survival. Treatment of Atf4$^{+/-}$ BM MDSCs with TES resulted in an impaired induction of Chop. In addition, MDSCs isolated from 3LL-bearing Atf4$^{+/-}$ mice showed a 50% decrease in Atf4 induction and a reduction in the expression of Chop, suggesting the role of Atf4 as a major mediator of Chop induction in MDSCs from tumors. A partial deletion of Atf4 triggered a similar antitumor effect as that found in Ddit3$^{-/-}$ mice. Thus, the induction of Chop in tumor MDSCs was mediated by induction of Atf4.

Chop Regulates MDSC Activity by Modulating IL-6:

Similar levels of C/EBPβ mRNA were found in wild-type and Ddit3$^{-/-}$ MDSCs from tumors. Conversely, a higher expression of the inhibitory form C/EBPb LIP, without changes in C/EBPβ LAP and LAP*, was found in Ddit3$^{-/-}$ MDSCs, compared to controls. A similar elevation of C/EBPβ LIP was also noted in MDSCs from L-NAC-treated mice, suggesting the role of ROS or PNT as mediators of this pathway.

Translation of C/EBPβ LIP in MDSCs is favored by the expression of microRNA 142-3p (miR-142-3p) (Sonda et al., (2013) *Immunity* 38: 1236-1249). Higher levels of miR-142-3p were detected in Ddit3$^{-/-}$ MDSCs, compared to controls. Furthermore, Ddit3$^{-/-}$ MDSCs had decreased C/EBPβ activity, as tested by DNA-binding ELISA, and inhibited endogenous binding of C/EBPβ to IL-6 and arginase I promoters, measured by ChIP assay. The reduced binding of C/EBPβ to IL-6 promoter in Ddit3$^{-/-}$ MDSCs translated into a decreased production of IL-6 and lower expression of IL-6 receptor-linked protein, phospho-STAT3.

To determine the significance of the low expression of IL-6 in the antitumor effects induced by Chop deletion, 3LL cells over-expressing IL-6 (3LL-IL-6) were injected into wild-type and Ddit3$^{-/-}$ mice. Ectopic expression of IL-6 restored tumor growth in Ddit3$^{-/-}$ mice. In addition, MDSCs from Ddit3$^{-/-}$ mice bearing 3LL-IL-6 tumors were equally suppressive as control MDSCs from 3LL or 3LL-IL-6-bearing mice. Furthermore, the decreased levels of phospho-STAT3 observed in Ddit3$^{-/-}$ MDSCs were partially restored after ectopic expression of IL-6 in tumor cells. These data indicate the relevance of IL-6 in the antitumor effects induced by MDSC-Chop deletion.

The interaction between tumor-linked stress and antitumor immunity has now been determined. The data indicate a role of Chop as a mediator of tumor-induced anergy through the modulation of MDSC function and accumulation.

Chop expression is typically associated with pathways leading to cellular apoptosis. Thus, silencing of Chop in tumor cells induced resistance to cell death by various chemotherapy agents (Schonthal A. H. (2013) *Biochem. Pharmacol.* 85: 653-666). Now it has been shown that Chop deletion inhibits MDSC turnover and also changes MDSC immune-suppressive function into one that promotes antitumoral T cell responses, indicating the role of Chop as a central mediator of the inflammatory function in MDSCs.

Although there are no current therapies to block Chop, some therapeutic possibilities include the inhibition or scavenging of ROS and/or PNT (Bronte et al., (2005) *J. Exp. Med.* 201: 1257-1268; Corzo et al., (2009) *J. Immunol.* 182: 5693-5701; De Santo et al., (2005) *Proc. Natl. Acad. Sci. U.S.A.* 102: 4185-4190; Lu et al., (2011) *J. Clin. Invest.* 121: 4015-4029; Sawant et al., (2013) *Cancer Res.* 73: 6609-6620). However, the data of the present disclosure now demonstrate the central role of Chop in MDSC suppressive activity and suggest the advantage of overcoming tumor-induced MDSC suppression by directly reducing Chop activity by contact with an inhibitory agent or by reducing expression of Chop by a heterologous agent, thereby offering a novel method of increasing immunological attack against a tumor.

Chop Mediates Tumor Growth:

Preliminary evidence in different cancer models supports a role for Chop in tumor growth. Wild-type and Chop-null mice were injected with different tumor cells that have functional Chop, including 3LL (Lewis Lung Carcinoma), EL-4 (thymus), MCA-38 (colon), and B16 (melanoma) cells, and tumor growth was monitored. By injecting Chop-null mice with Chop-positive tumor cells, the effect of Chop exclusively in the stromal cells (i.e., the cells surrounding the tumor) could be monitored. Importantly, a decrease in tumor growth of all cancer types was observed in Chop-null mice, as compared to wild-type mice. Simply stated, in the absence of stromal Chop, tumor growth is reduced. A similar result is found after injection of tumors in Chop null bone marrow chimeric mice. The results demonstrate for the first time the importance of stromal Chop, and specifically MDSC, for tumor growth. However, the mechanism by which stromal Chop influences tumor growth remains unclear.

MDSCs are the most commonly found cell types in the tumor stroma, and specifically accumulate in the tumor microenvironment as a result of the expression of several tumor-derived factors. The presence of stromal MDSCs in the tumor microenvironment has been linked to a robust inhibition of anti-tumor immunity, consequently promoting of tumor progression. As stromal Chop and stromal MDSCs both play a key role in tumor growth, it is possible that Chop is involved in MDSC-related tumor growth and development.

A previous study has suggested the role of the CCAAT/enhancer binding protein β (C/EBPβ), a transcription factor that controls granulopoiesis during inflammation, in the modulation of global MDSC activity. However, the mechanisms regulating C/EBPβ signaling in MDSC are unknown. Multiple suppressive pathways in tumors, including exposure to high levels of reactive species, starvation of nutrients, hypoxia, and acidosis, are characterized by the induction of a cellular process known collectively as integrated stress response (ISR). ISR is characterized by the activation of endoplasmic reticulum (ER) proteins such as PKR-like ER-related kinase (PERK), the phosphorylation of the eukaryotic translation initiation factor 2 alpha (eIF2α), and the induction of the transcription factors Atf4 and Chop. Although an adequate ISR in tumor cells is fundamental for their growth and survival, and promotes suppressive pathways in immune cells, limited information is known on the direct effects of ISR on MDSC. Without being unnecessarily limited by this hypothesis, we propose that Chop may be a master regulator of the inhibitory function of tumor-infiltrating MDSC through the regulation of C/EBPβ signaling, and the inhibiting the Chop:C/EBPβ axis may restore anti-tumor immunity and enhance the efficacy of immunotherapy in cancer.

Multiple lines of preliminary evidence support a role for Chop in tumor-associated MDSCs, and implicate Chop in the ISR pathway. First, a role for Chop in MDSC cells is suggested by the observed increase in expression of Chop mRNA in granulocytic MDSC and monocytic MDSC, as compared to T- and B cells, macrophages, and dendritic cells. Secondly, the expression of Chop in MDSC occurred at the tumor site, but not at the spleen, suggesting the role of the tumor proximity in the induction of Chop in MDSC. Notably, tumor cells also demonstrate increased Chop expression. Finally, the higher levels of Chop in MDSC correlated with the induction of other ISR markets such as PERK, ATF4, and phospho-eIF2α.

Chop Mediates Immune Suppression in Tumors:

Several stress pathways converge upon the translation initiation factor 2α (eIF2α), which when phosphorylated conserves cellular resources by arresting translation, while activating Chop. In fact, treatments with several stress-related products including hydrogen peroxide, peroxynitrites, pH 6.5, or PGE2 showed induction of Chop in MDSC. With the knowledge that Chop promotes tumor growth, Chop is expressed in MDSCs, and MDSCs mediate immunosuppression to promote tumor growth, it is possible that Chop is the key mediator of MDSC immunosuppression and tumor growth. Multiple lines of evidence support this notion. First, depletion of CD8$^+$ T cells, but not CD4$^+$ cells, restored tumor growth in Chop-null mice, suggesting a potential role for the immune system, specifically CD8$^+$ T cells, in the Chop-MDSC anti-tumor effect. In accordance with this, an increased percentage of CD8$^+$ cells in tumors and elevated numbers of T cells procuring IFNγ were found in Chop-null mice, as compared to tumor-bearing controls. Secondly, Chop-null MDSCs are less suppressive of T cell proliferation than wild-type MDSCs. Finally, Chop-null MDSCs demonstrate significant decrease in the production of reactive oxygen/nitrogen species, key mediators of immunosuppression, relative to wild-type MDSCs.

Surprisingly, inhibition of the MDSC-immunosuppressive pathway prevents MDSC from being immunosuppressive and instead turns them into myeloid cells that can drive an anti-tumor response and increase T cell function after vaccines. In addition, the anti-tumor responses observed in Chop null mice were dependent of effect CD8$^+$ T cell responses.

Chop Mediates Accumulation of MDSC in Tumors:

Preliminary evidence suggests a role for Chop in MDSC-mediated immunosuppression and tumor growth. As tumor growth is reduced in Chop-null mice, one would expect there to be a parallel reduction in MDSC levels at the tumor site in these mice. Surprisingly, Chop-null mice injected with Chop-positive tumor cells had increased MDSC proliferation at the tumor site relative to wild-type mice. Furthermore, there is a marked increase in MDSC affinity for the tumor tissue in the Chop-null mice relative to the wild-type mice. The increase in proliferation and affinity lead to the net accumulation of MDSC cells at the tumor site in the Chop-null mice. However these Chop negative MDSC at the site of the tumor were not immunosuppressive and were instead able to stimulate T cells, which is the normal function of myeloid cells.

One aspect of the disclosure, therefore, encompasses embodiments of a method of modulating the level of activity of C/EBP-homologous protein (Chop) in a myeloid-derived suppressor cell (MDSC) or population of said cells, said method comprising delivering to a recipient MDSC or population of said recipient cells a composition comprising an agent that inhibits the activity of Chop in the cell(s) or reduces the expression of a Chop or a derivative thereof, and a vehicle for delivery of the agent to the interior of the recipient cell.

In some embodiments of this aspect of the disclosure, the agent can be an siRNA and result in gene silencing of the Chop gene in the recipient MDSC or population of MDSCs.

In some embodiments of this aspect of the disclosure, the siRNA can be an isolated double-stranded ribonucleic acid (dsRNA) molecule having either no overhang regions or at least one overhang region, wherein each overhang region contains six or fewer nucleotides, and wherein the dsRNA inhibits expression by a cell of a Chop protein, and wherein a first strand of the dsRNA is substantially identical to the sequence according to SEQ ID NO: 1, and a second strand is substantially complementary to the first.

In some embodiments of this aspect of the disclosure, the first strand of the dsRNA can have a nucleotide sequence according to SEQ ID NO: 1.

In some embodiments of this aspect of the disclosure, the vehicle can be a liposome or a nanoparticle.

In some embodiments of this aspect of the disclosure, the composition can further comprise a pharmaceutically acceptable carrier.

In some embodiments of this aspect of the disclosure, the recipient MDSC or population of said recipient cells can be isolated from an animal or human subject.

In some embodiments of this aspect of the disclosure, the isolated MDSC or population of said recipient cells can be cultured cells.

In some embodiments of this aspect of the disclosure, the composition is administered to the recipient animal or human subject intravenously or directly into a tumor of said subject.

In some embodiments of this aspect of the disclosure, the composition can be administered to the recipient animal or human subject intravenously or directly into a tumor of said subject, and wherein reducing the activity of Chop in the MDSC(s) of the tumor increases an antitumor immune response.

In some embodiments of this aspect of the disclosure, the composition can be administered to the recipient animal or human subject intravenously or directly into a tumor of said subject, and wherein reducing the activity of Chop in the MDSC(s) of the tumor decreases the volume of the tumor.

Another aspect of the disclosure encompasses embodiments of a method of increasing the efficacy of an immune system-based treatment of a tumor comprising the steps of: (a) delivering to an animal or human subject a pharmaceutically acceptable composition providing a T cell based immunotherapeutic reduction in a tumor; (b) reducing the level of activity of C/EBP-homologous protein (Chop) in a population of myeloid-derived suppressor cells (MDSCs) in the animal or human subject, said method comprising delivering to said subject a pharmaceutically acceptable composition comprising an effective dose of an siRNA, a pegylated-liposome vehicle for delivery of the siRNA to the interior of the MDSCs, and a pharmaceutically acceptable carrier, wherein the siRNA is an isolated double-stranded ribonucleic acid (dsRNA) molecule having either no overhang regions or at least one overhang region, wherein each overhang region contains six or fewer nucleotides, and wherein the dsRNA inhibits expression by a cell of a Chop protein, and wherein a first strand of the dsRNA is substantially identical to the sequence according to SEQ ID NO: 1, and a second strand is substantially complementary to the first, and results in gene silencing of the Chop gene in the recipient MDSCs; thereby increasing the efficacy of the T cell based immunotherapy directed against the tumor.

In some embodiments of this aspect of the disclosure, the first strand of the dsRNA has a nucleotide sequence according to SEQ ID NO: 1.

Another aspect of the disclosure encompasses embodiments of a composition comprising an agent that when delivered to a myeloid-derived suppressor cell (MDSC) or population of said cells reduces the level of expression of a Chop-encoding gene, thereby reducing the level of Chop in the cell or cells.

In some embodiments of this aspect of the disclosure, the composition can further comprise a vehicle suitable for the delivery of the agent to the interior of the cell or cells.

In some embodiments of this aspect of the disclosure, the vehicle can be a liposome.

In some embodiments of this aspect of the disclosure, the agent can be an siRNA.

In some embodiments of this aspect of the disclosure, the siRNA can be an isolated double-stranded ribonucleic acid (dsRNA) molecule having either no overhang regions or at least one overhang region, wherein each overhang region contains six or fewer nucleotides, and wherein the dsRNA inhibits expression by a cell of a Chop protein, and wherein a first strand of the dsRNA is substantially identical to the sequence according to SEQ ID NO: 1, and a second strand is substantially complementary to the first.

In some embodiments of this aspect of the disclosure, the first strand of the dsRNA has a nucleotide sequence according to SEQ ID NO: 1.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Differential Expression of ISR-Related Genes in Cellular Populations from Tumors Up-regulation of ISR-related genes in tumors is induced after chemotherapy, radiotherapy, or as the result of the hostile milieu present in the tumor microenvironment. However, the distribution of the ISR-linked genes within tumors remains poorly characterized. The expression of the ISR marker gene, Chop, in different cellular populations sorted from s.c. 3LL tumors was compared.

Figure 1B:
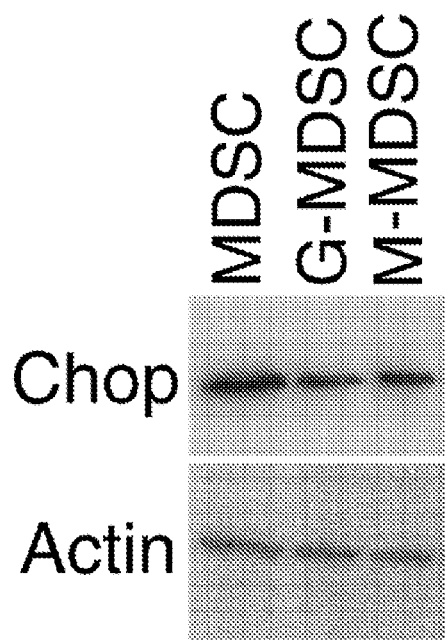
Figure 1C:
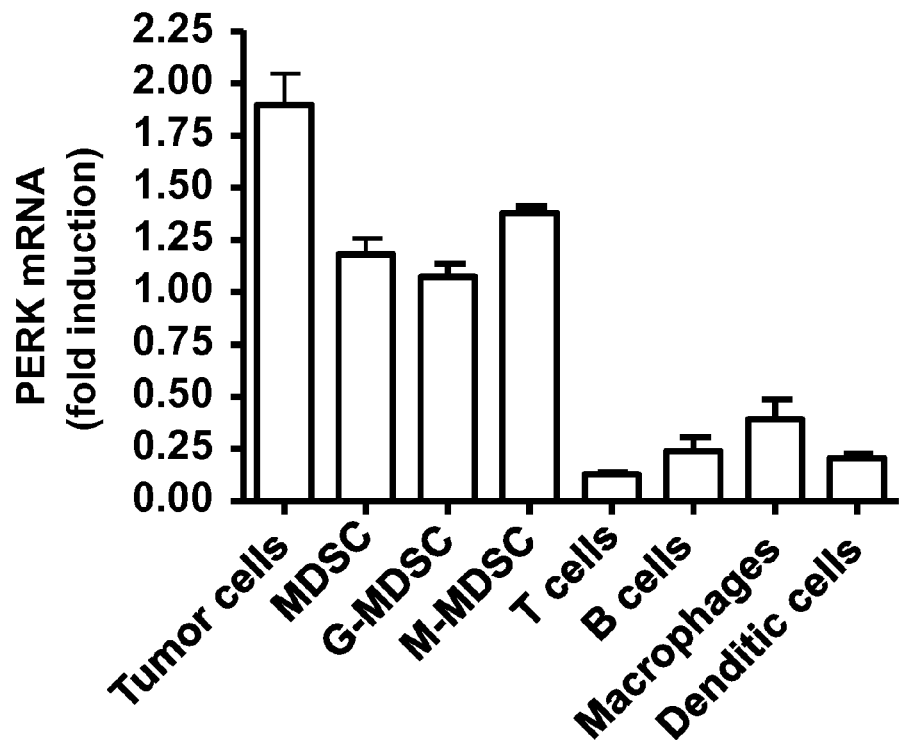
Figure 1D:
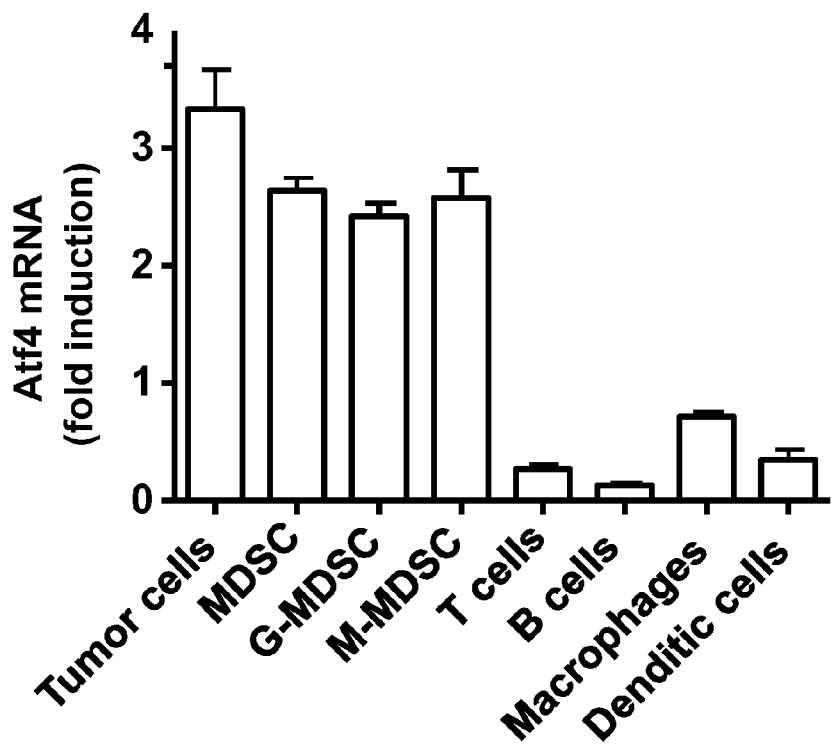
Figure 2A:
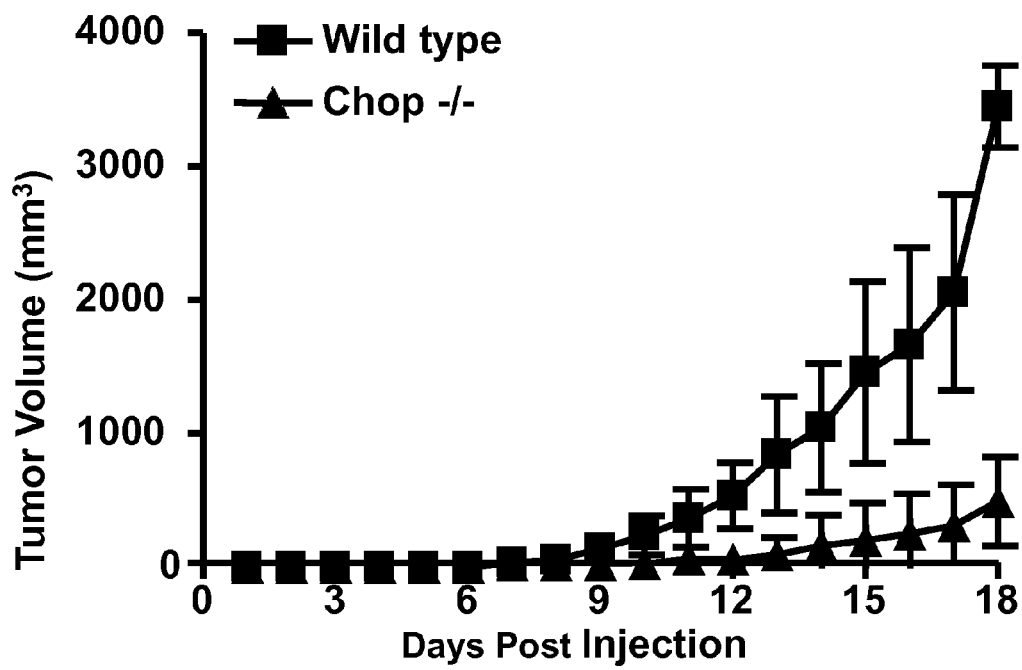
FIG. 2A illustrates the deletion of Chop in stromal cells prevents the growth of 3LL tumors.
Figure 2B:
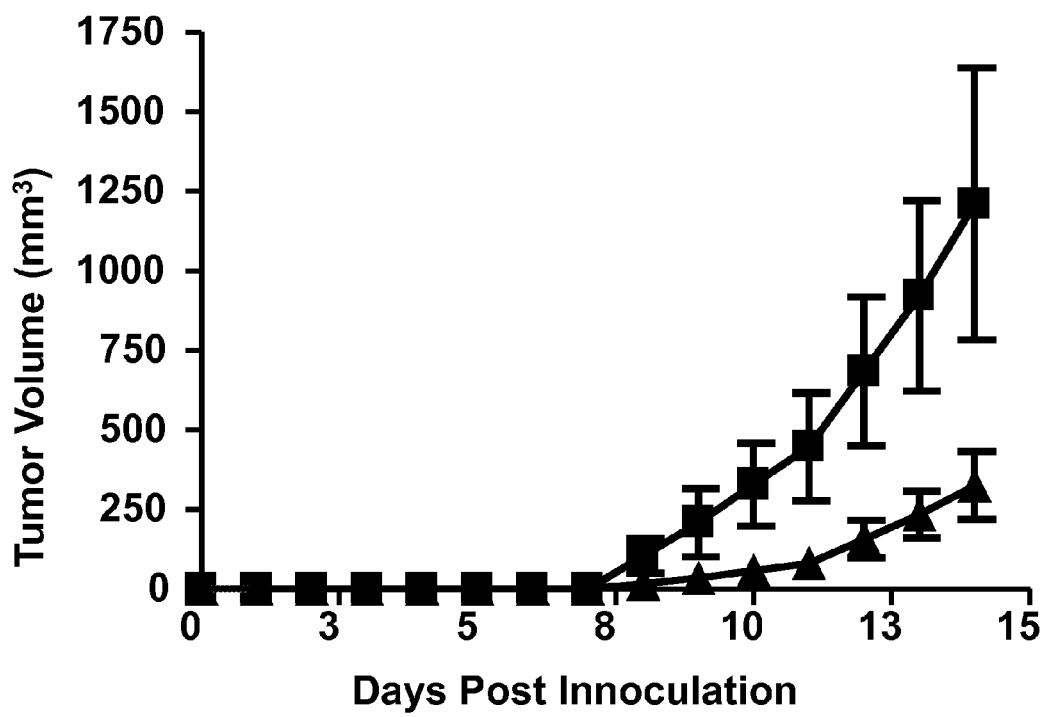
FIG. 2B illustrates the deletion of Chop in stromal cells prevents the growth of EL-4 tumors.
Figure 2C:
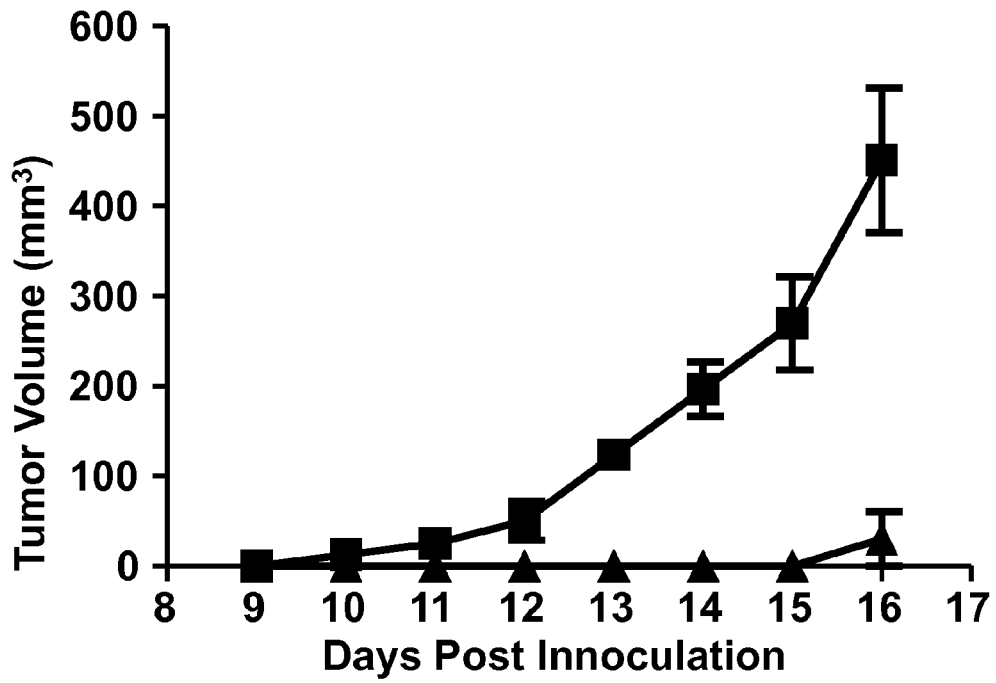
FIG. 2C illustrates the deletion of Chop in stromal cells prevents the growth of B16 tumors.
Figure 2D:
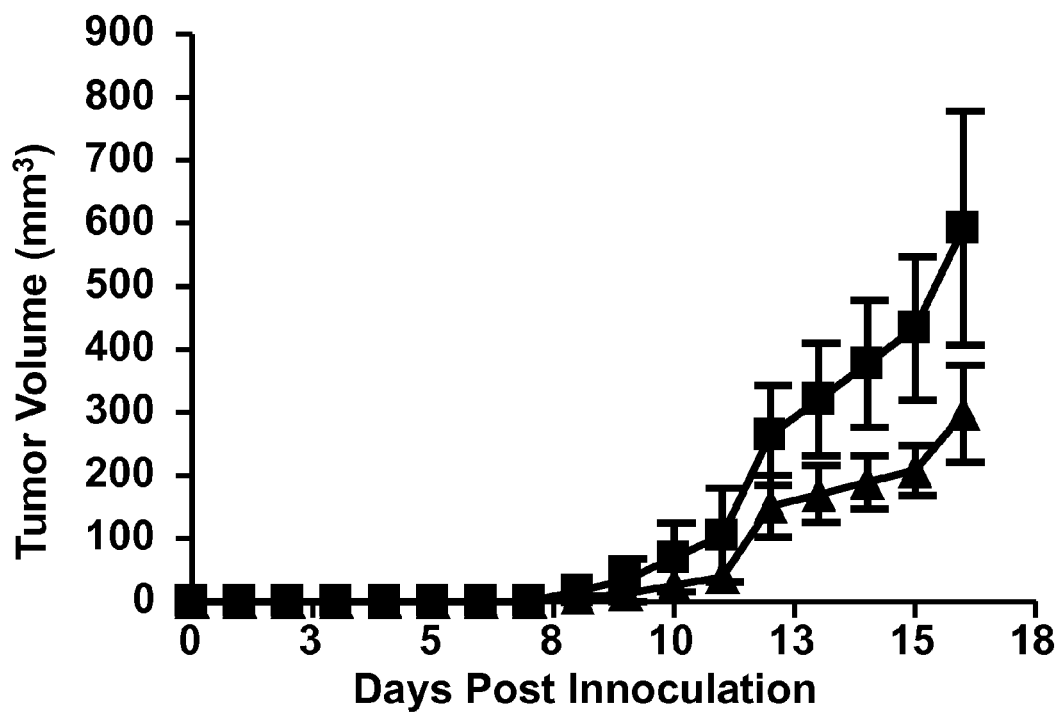
FIG. 2D illustrates the deletion of Chop in stromal cells prevents the growth of MCA-38 tumors.

A higher expression of Chop mRNA was preferentially found in tumor cells ($CD45^{neg}$ $CD49f^+$) and MDSC ($CD11b^+Gr1^+$), as compared to T- and B cells, macrophages, and dendritic cells (FIG. 1A). The increased accumulation of Chop was equally found in granulocytic MDSC (G-MDSC, $CD11b^+Ly6G^{high}Ly6C^{low}$), and monocytic MDSC (M-MDSC, $CD11b^+Ly6G^{neg}Ly6C^{high}$) (FIG. 1A-B). In addition, the higher levels of Chop in MDSC correlated with the induction of other ISR markers such as PERK, Atf4 (FIG. 1C-D), and phospho-eIF2α (data not shown). Also, the expression of Chop in MDSC occurred at the tumor site, but not at the spleen, suggesting the role of the tumor proximity in the induction of Chop in MDSC (FIG. 1A).

Example 2

Deletion of Chop in Stromal Cells Prevents Tumor Growth in Different Models

The possibility of the prevention of stress responses in stromal cells, in particular Chop, in preventing tumor growth was examined. Wild type and Chop null mice were injected with different tumors that have a functional Chop, including 3LL, EL-4, MCA-38, and B16, after which tumor growth was monitored. This model allowed testing the effect of Chop exclusively in the stromal cells. A decrease in tumor growth in all tested models was noticed in Chop null mice, as compared to wild-type mice (FIG. 2), suggesting for the first time the role of stromal Chop in tumor growth.

Example 3

The Anti-Tumor Effect Induced by Chop Knockdown is Mediated by $CD8^+$ T Cells

Figure 3A:
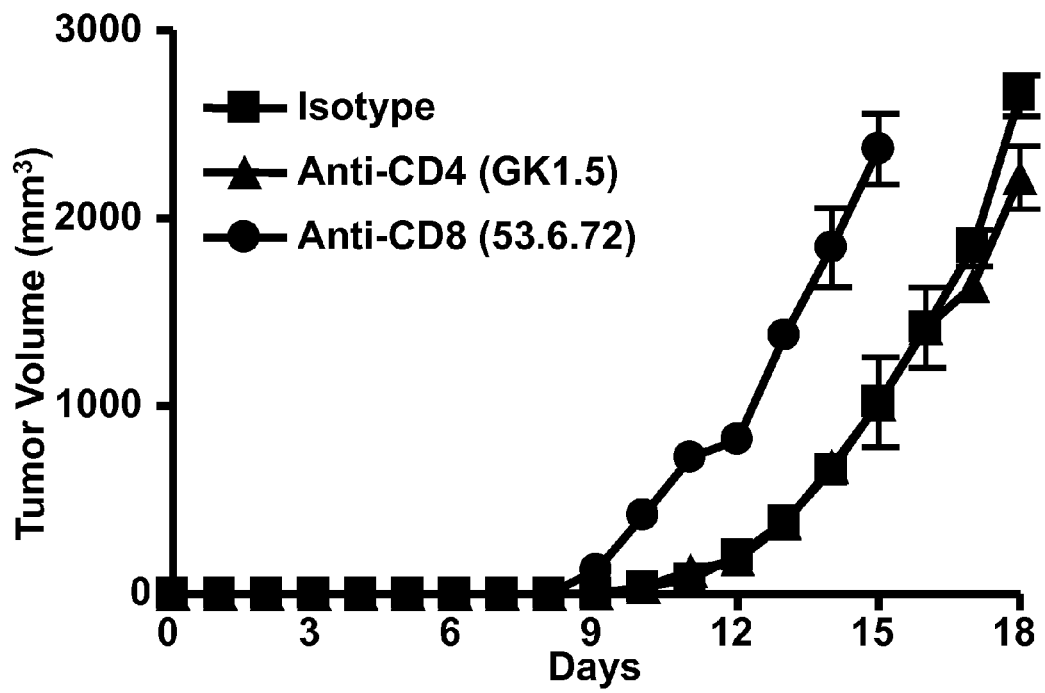
FIGS. 3A-3F illustrate the anti-tumor effects found in Chop KO mice are mediated by $CD8^+$ T cells.
Figure 3B:
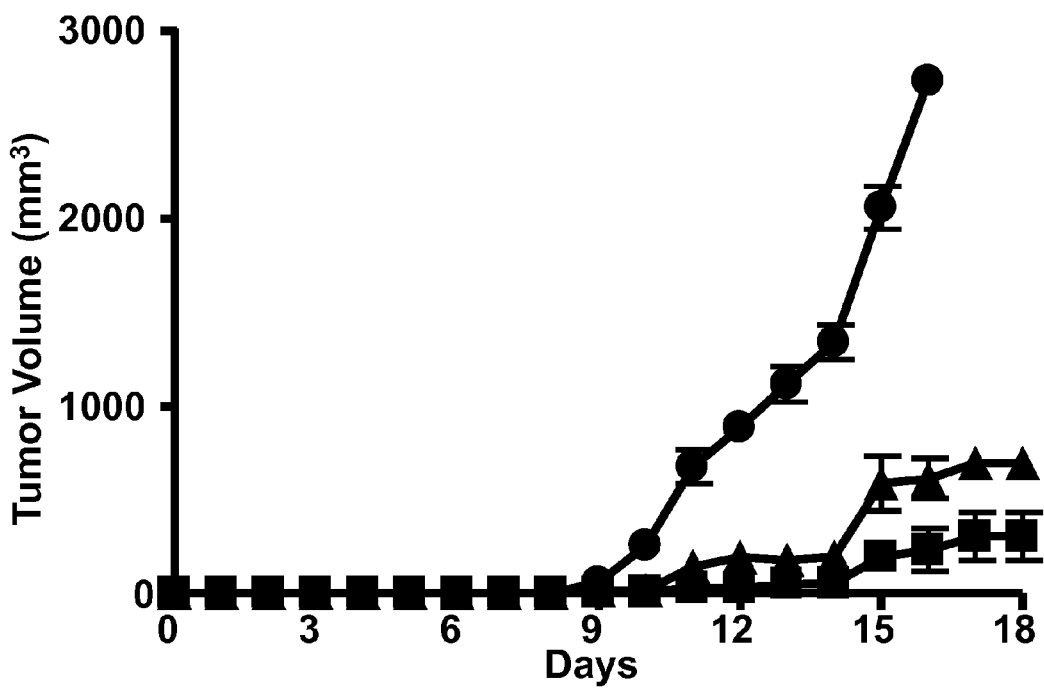
Figure 3C:
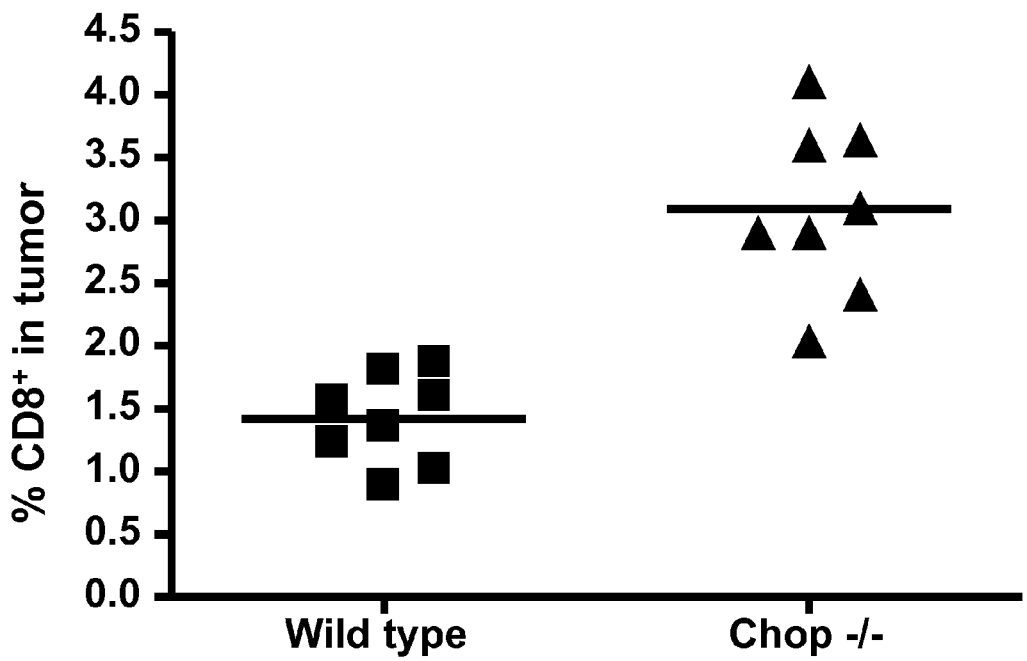
Figure 3D:
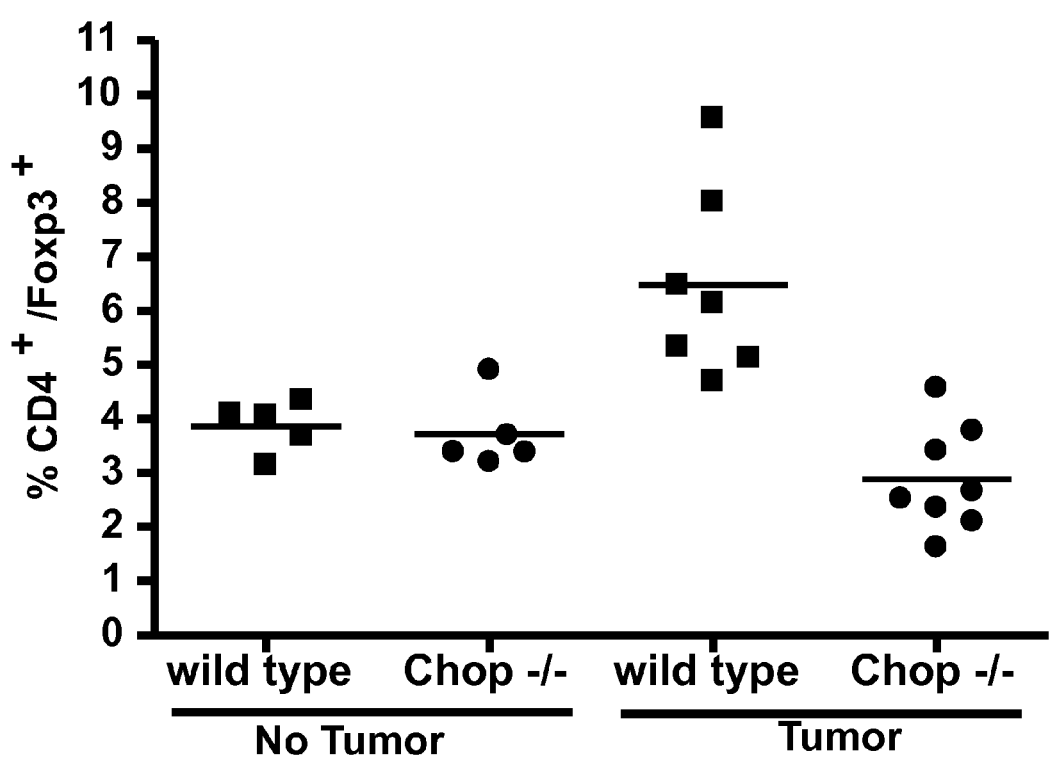
Figure 3E:
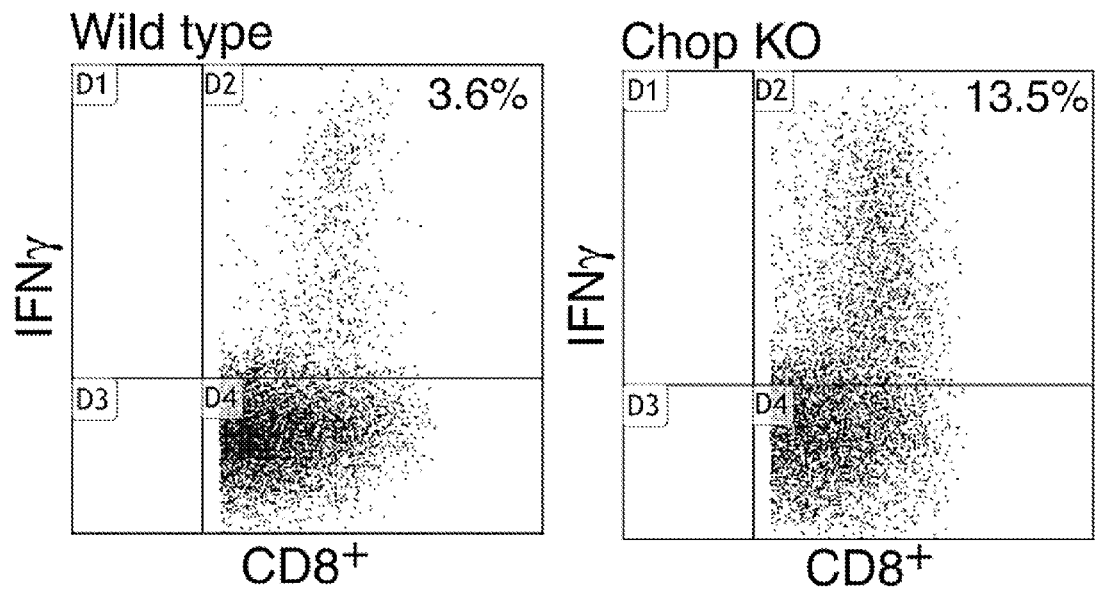
Figure 3F:
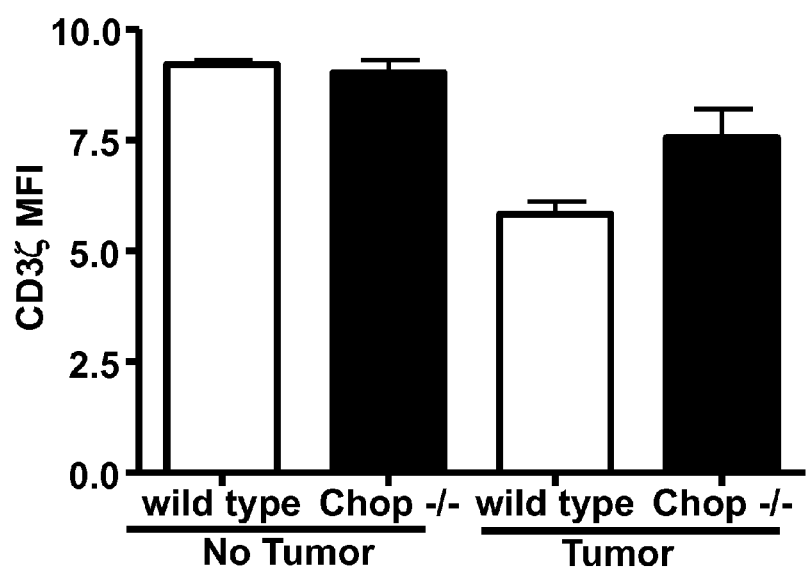

To determine the role of T cells in the anti-tumor effect induced by the absence of Chop, 3LL-bearing mice were treated with specific antibodies against $CD8^+$ or $CD4^+$ T cells. Depletion of $CD8^+$ T cells, but not $CD4^+$ cells, restored tumor growth in Chop null mice (FIG. 3A), suggesting a potential effector role of $CD8^+$ T cells. Furthermore, the anti-tumor effect found in Chop KO mice associated with an increased percentage of $CD8^+$ T cells in tumors (FIG. 3B), a low accumulation of splenic Tregs (FIG. 3C), and an elevated number of $CD8^{+\ T\ cell}$s producing IFNγ (FIG. 3D). Also, a partial recovery of CD3ζ chain expression, a key protein for T cell activation, was found in T cells from 3LL-bearing Chop −/− mice, but not in T cells from controls with tumors (FIG. 3E). These results suggest the prevention of T cell dysfunction by deletion of stromal Chop in tumor-bearing mice. However, the anti-tumor effects induced by $CD8^+$ T cells in Chop KO mice were not the result of an intrinsic effect of Chop on T cells, as they were negative for Chop expression (FIG. 1).

Example 4

Figure 4A:
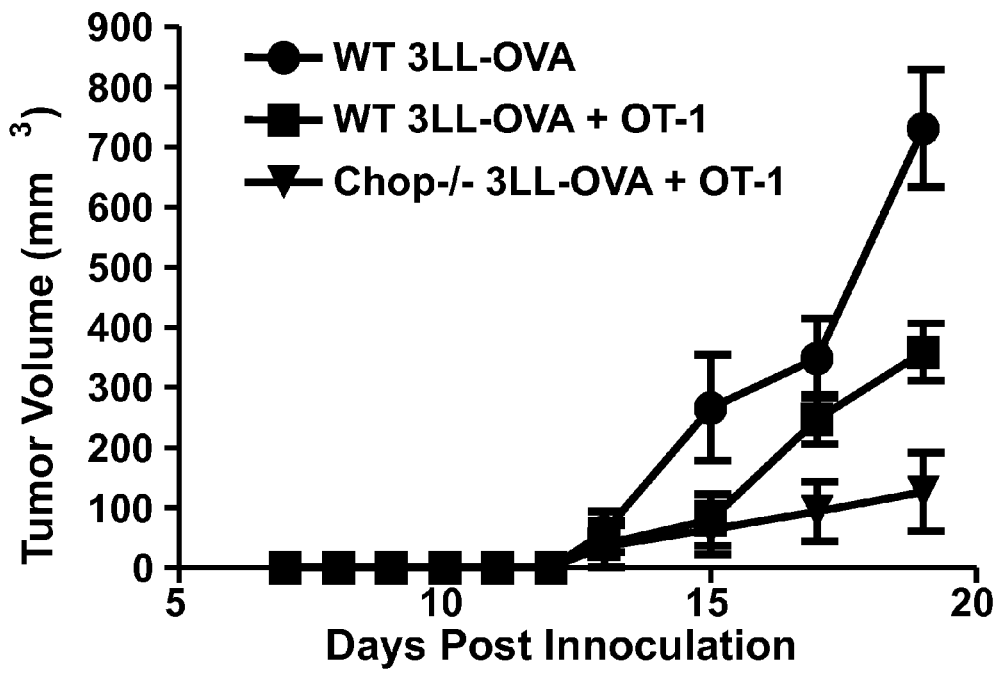
FIGS. 4A and 4B illustrate that the deletion of Chop in tumor stroma enhances efficacy of T cell-based immunotherapy.
Figure 4B:
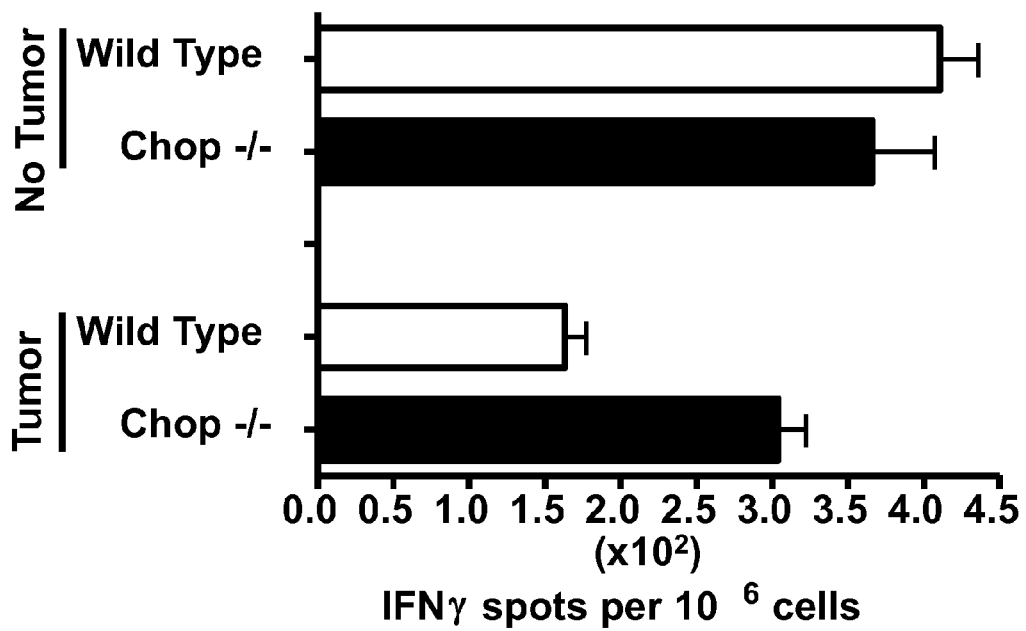

To address the role of Chop in tumor-induced tolerance, wild-type and Chop null mice were injected s.c. with 3LL tumors expressing the model tumor antigen ovalbumin (OVA). Seven days later, $1 \times 10^6$ anti-OVA transgenic $CD8^+$ T cells (OT-1) were adoptively transferred i.v. into the mice, followed by vaccination using SIINFEKL. Then, mice were followed for tumor growth and T cell function. A higher anti-tumor effect was observed in Chop-null mice receiving OT-1 cells, as compared to wild-type controls transferred with the same number of OT-1 cells (FIG. 4A). In addition, increased numbers of OT-1 cells producing IFNγ were detected in the spleens of tumor-bearing Chop null mice after vaccination and activation ex vivo with SIINFEKL, as compared to spleens from wild-type controls (FIG. 4B). This suggests the role of the stromal Chop in tumor-induced tolerance and the potential benefit of its deletion for immunotherapy.

Example 5

Chop is a Master Regulator for the Immunosuppressive Function of MDSC

Figure 5A:
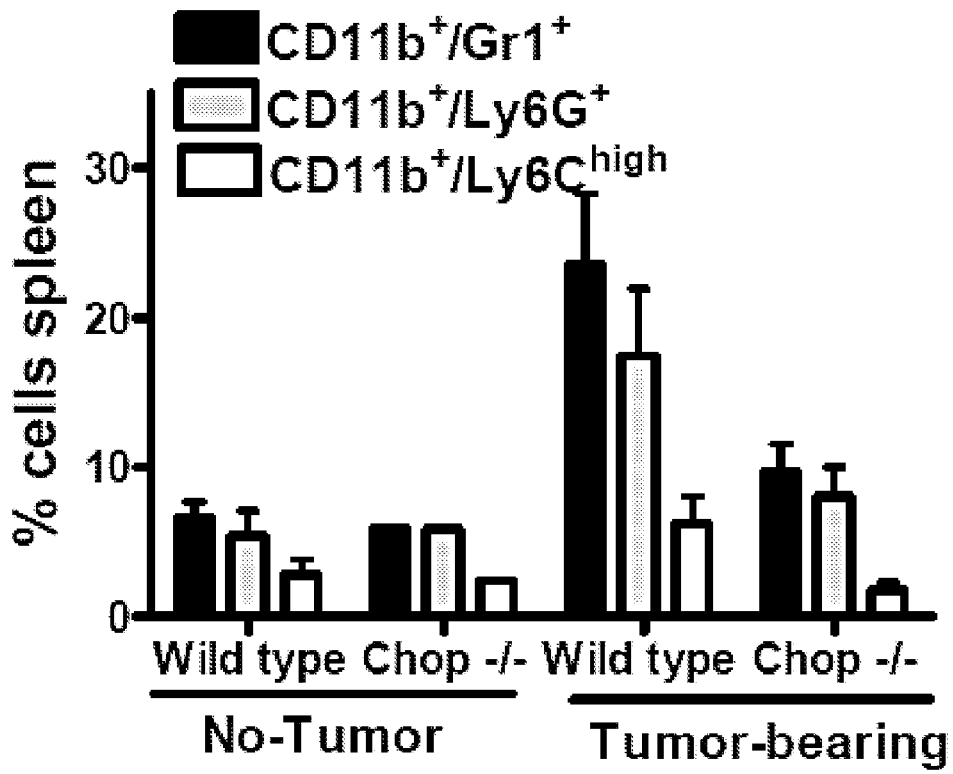
Figure 5B:
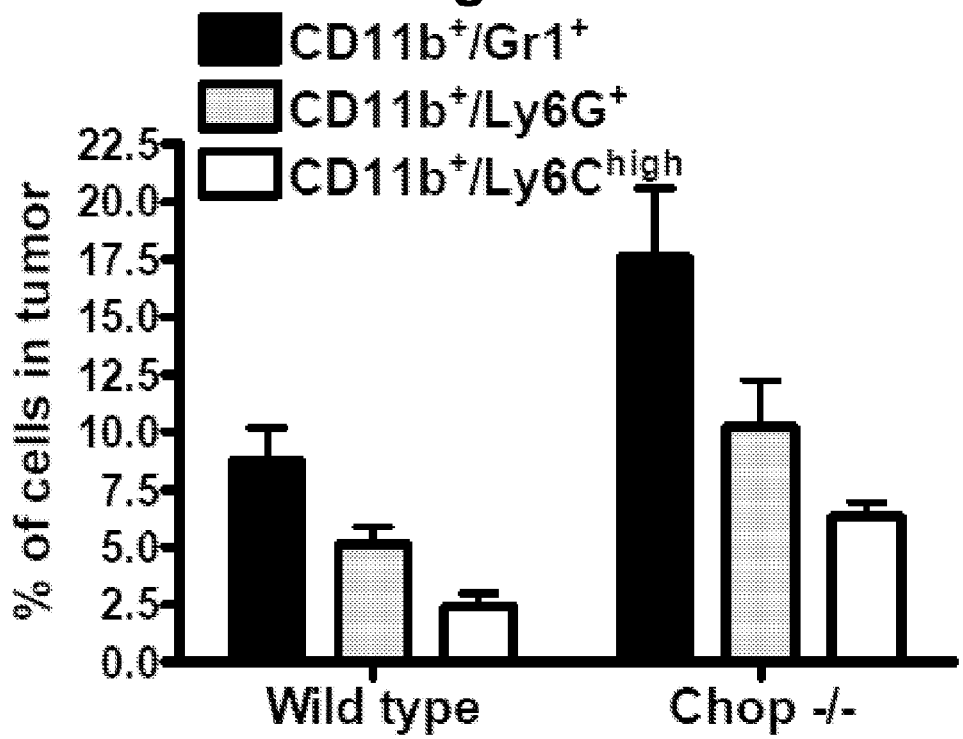
Figure 5C:
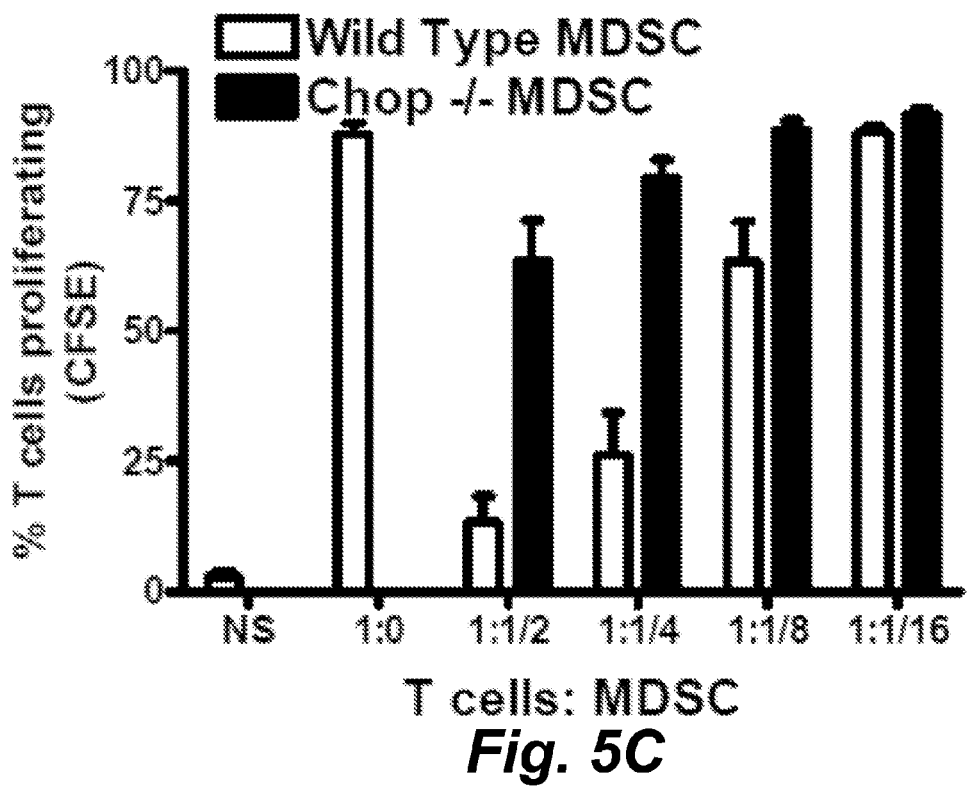
Figure 5D:
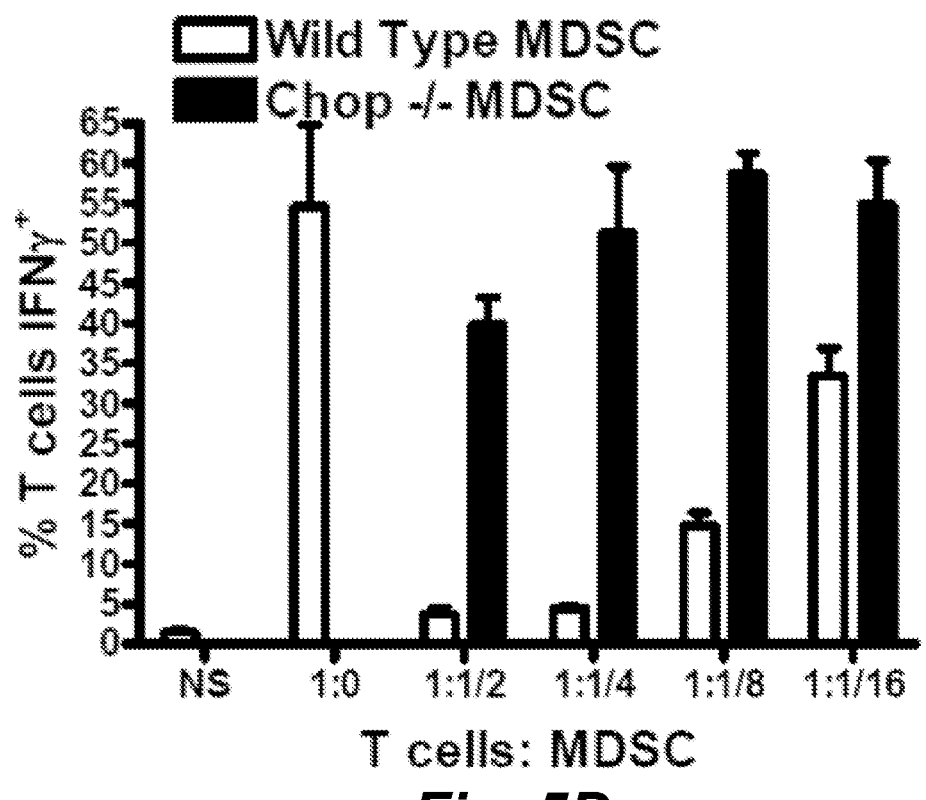

The absence of Chop in tumor stroma impairing the accumulation and the immune suppressive function of MDSC was examined. Lower percentages of both MDSC subsets were observed in the spleen of 3LL-bearing Chop KO mice, as compared to controls (FIG. 5A). Conversely, an unexpected increase in the accumulation of MDSC (G-MDSC and M-MDSC) was detected in tumors from Chop null mice, as compared to those from wild-type controls (FIG. 5B). However, the $CD11b^+Gr1^+$ cells present in tumors from Chop null mice displayed a limited ability to block T cell proliferation and IFNγ production, as compared to those from control mice (FIG. 5C-D). The low inhibitory capacity of $CD11b^+Gr1^+$ cells from Chop KO mice associated with a decrease in their expression of major molecules associated with MDSC activity, including arginase, iNOS, and $gp91^{phox}$, and a low production of PNT (FIG. 5E-F). Altogether the results suggest the master role of Chop in the suppression and accumulation of MDSC in tumors. These studies were validated using other tumors models including EL-4, MCA-38, and B16, finding similar results.

Example 6

MDSC from Chop KO Tumors Block Tumor Growth

Figure 6B:
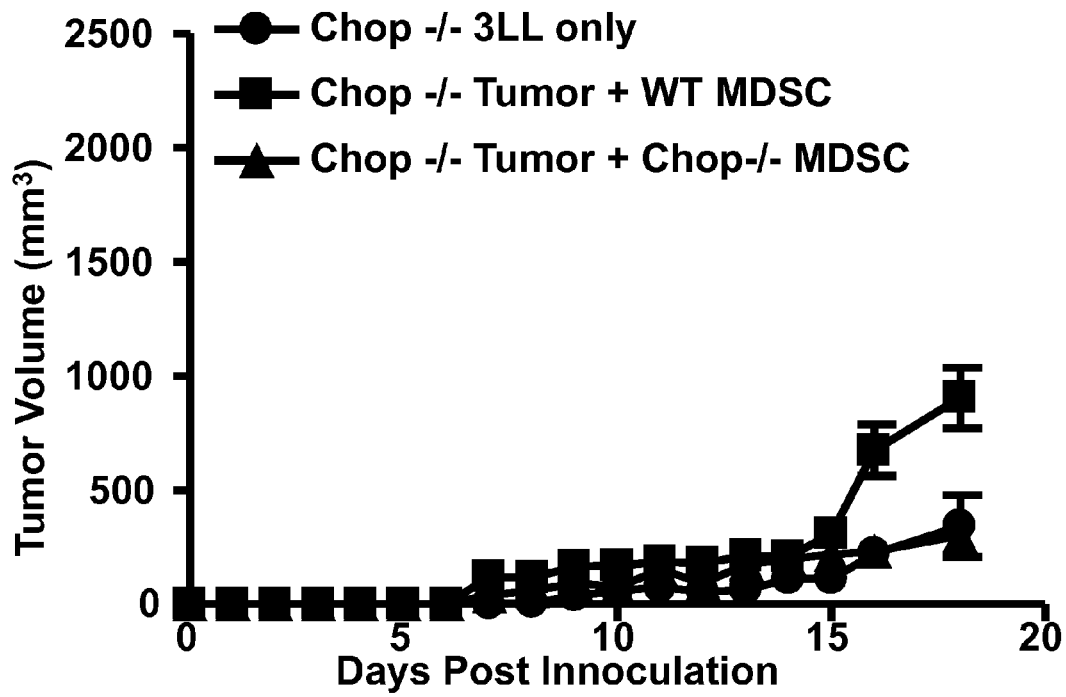
Figure 6C:
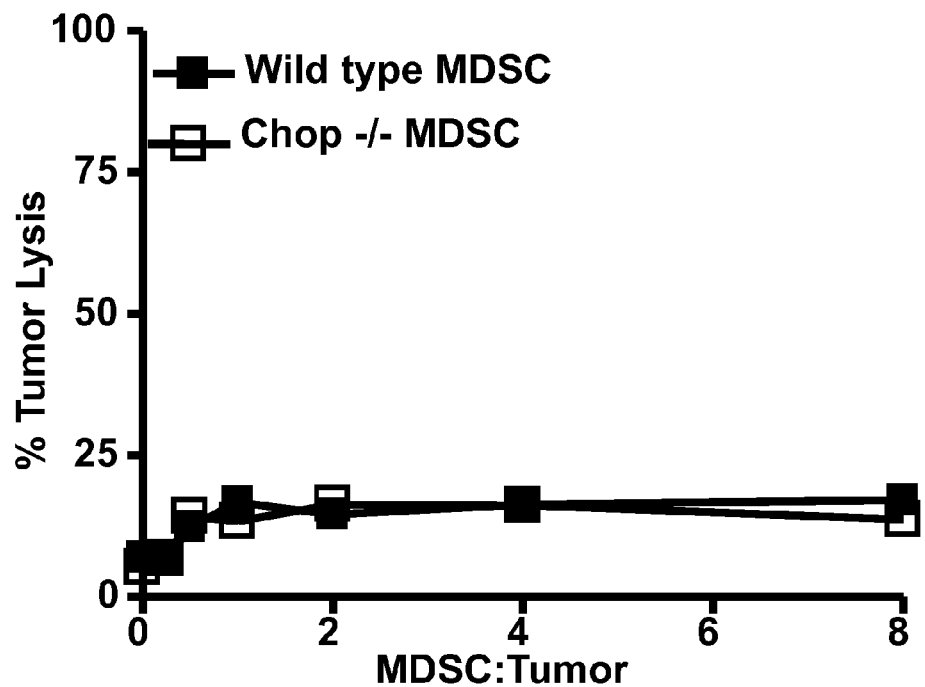

That the deletion of Chop in MDSC could not only prevent their immune suppressive activity, but also promoted anti-tumor responses, was examined. Therefore, $CD11b^+Gr1^+$ cells isolated from wild-type and Chop KO mice bearing 3LL tumors were mixed 1:1 with 3LL cells and injected s.c. into wild-type or Chop null mice. Co-injection of Chop null $CD11b^+Gr1^+$ cells into wild-type mice significantly prevented 3LL tumor growth (FIG. 6A). In addition, injection of wild-type MDSC into Chop KO mice partially rescued tumor growth, confirming the role of MDSC-Chop in tumor growth and suggesting the potential therapeutic opportunity of using Chop KO MDSC as a new anti-tumor therapy. Then, whether CD11b+Gr1+ cells from Chop KO induced direct killing of tumor cells was tested. A similar low cytotoxicity of 3LL tumor cells was found either after co-cultured with wild-type or Chop KO CD11b+Gr1+ cells (FIG. 6B), suggesting that the anti-tumor effects induced by Chop KO MDSC were not by a direct cytotoxic effect.

Example 7

Chop Null MDSC Activate Antigen-Specific T Cells

Because tumor-associated CD11b+Gr1+ cells from Chop KO mice practically lack T cell suppressive function and failed to directly kill tumor cells, whether they have the ability to prime T cells was tested. Thus, T cell proliferation was tested in CFSE-labeled OT-1 cells co-cultured in a 1:1/10 ratio with tumor-associated CD11b+Gr1+ cells previously loaded with SIINFEKL. An active proliferation was found in OT-1 cells co-cultured with Chop KO CD11b+Gr1+ cells, but not in those co-cultured with wild-type MDSC or cultured alone (FIG. 7A). Furthermore, the increased T cell proliferation effect induced by Chop KO-MDSC correlated with a higher expression of the dendritic cell marker CD11c, and MHC class II and I (FIG. 7B-C), suggesting that deletion of Chop switches MDSC into dendritic cell-like cells.

Example 8

Stress Factors Induce Chop and Promote Suppressive Function in MDSC

Whether the treatment of non-tumor MDSC with stress factors present in the tumor microenvironment would mimic the alterations found in tumor-associated MDSC, including high Chop and increased suppressive function was examined. To test this, MDSC in vitro were generated by culturing bone marrow progenitors for 4 days in the presence of G-CSF, GM-CSF, and IL-6. During the last 24 hours of differentiation, MDSC were cultured in the presence of different stress factors, including tissue conditioned medium (TCM), acidosis (pH: 6.5), arginine starvation (20 μM), PNT (250 μM), and nitric oxide (NO) donor Sin-1 (250 μM). Then, Chop expression and MDSC:T cell suppression studies were performed.

Figure 8A:
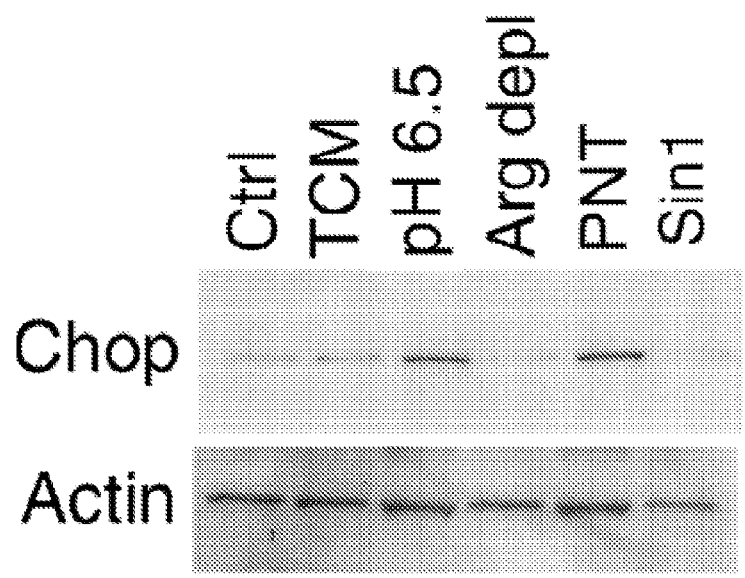
FIGS. 8A and 8B illustrate that stress increases Chop-linked suppression in MDSCs.
Figure 8B:
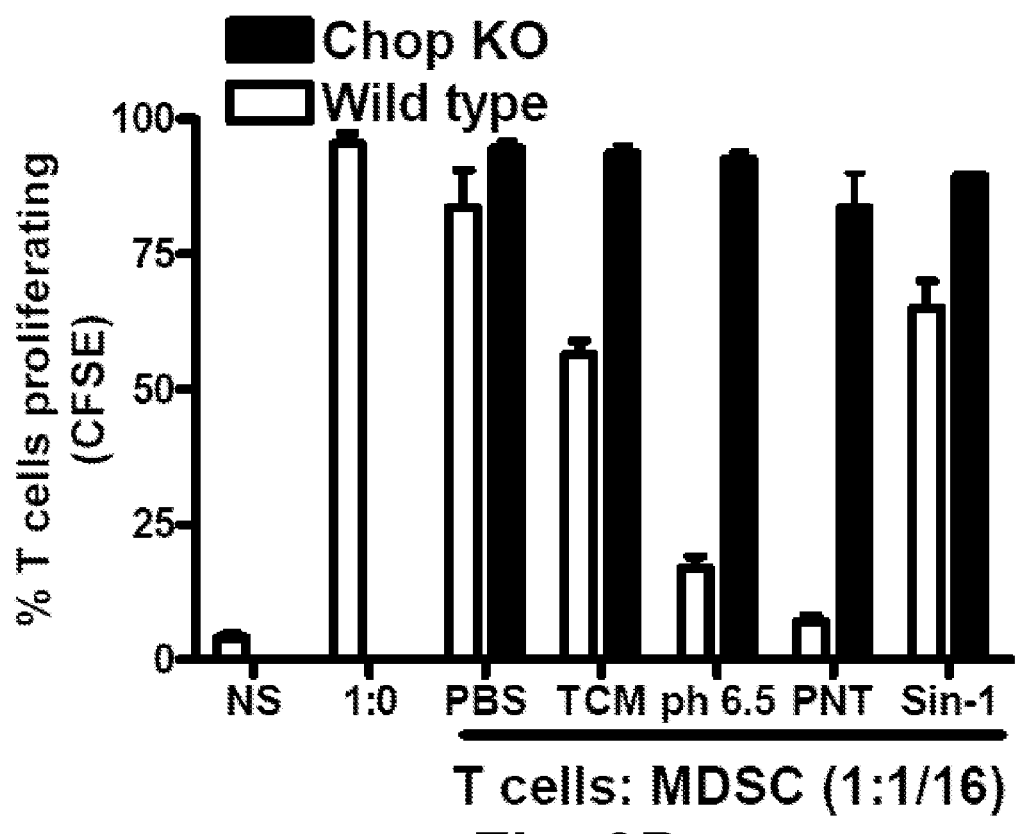

A significant increase in the expression of Chop was found in MDSC cultured under low pH or with PNT, but not after starvation with arginine, addition of TCM, or Sin-1 (FIG. 8A). In addition, the increased expression of Chop after stress-treatment correlated with an elevated ability of MDSC to block T cell proliferation at ratio 1:1/16, at which control MDSC failed to suppress (FIG. 8B). The induction of MDSC suppression by stress factors did not occur in Chop KO MDSC (FIG. 8B), indicating the significant role of Chop in the modulation of MDSC function after stress activation.

Example 9

Chop Expression Modulates C/EBPβ Signaling in MDSC

Transcription factor C/EBPβ has been previously reported as a global mediator of MDSC activity. However, the mechanisms by which C/EBPβ is regulated in MDSC are unknown.

Three isoforms of C/EBPβ with opposite functions are generated from a single mRNA through alternative initiation of translation. Isoforms liver-enriched activator proteins (LAP* and LAP) are transcriptional activators of chronic inflammation-associated genes (IL-6, TNFα, arginase), while the liver-enriched inhibitory protein (LIP) lacks transcriptional activity. The major mechanism of how LIP blocks LAP function is by competing for promoter sites. Previous studies in cell lines suggested a preferential binding of Chop to LIP, thereby promoting LAP activity. Thus, that Chop in MDSC is a regulator of C/EBPβ signaling was possible.

Figure 9A:
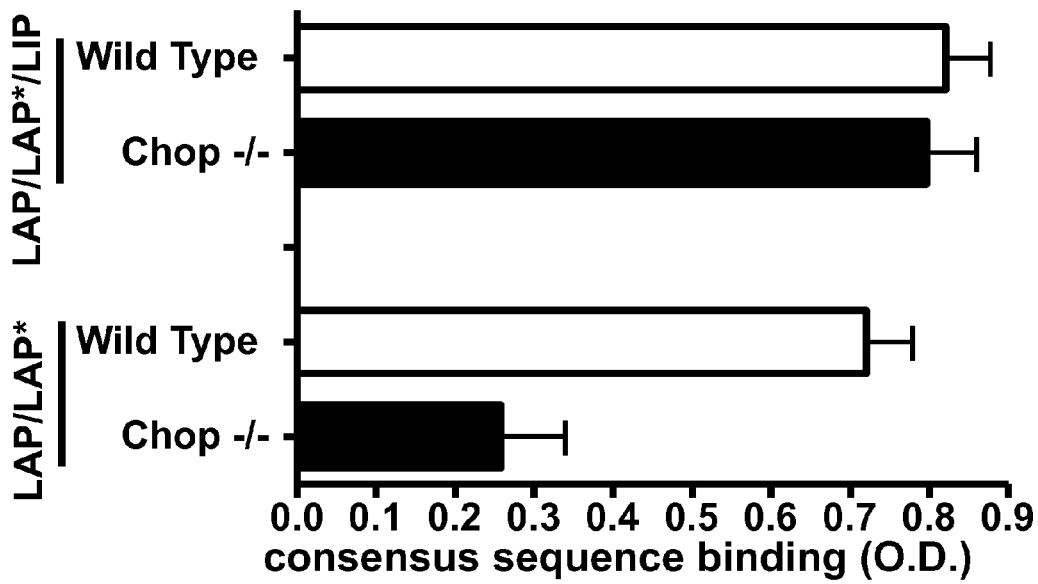
FIGS. 9A and 9B illustrate that Chop expression regulates C/EBPβ in CD11b$^+$Gr1$^+$ cells.
Figure 9B:
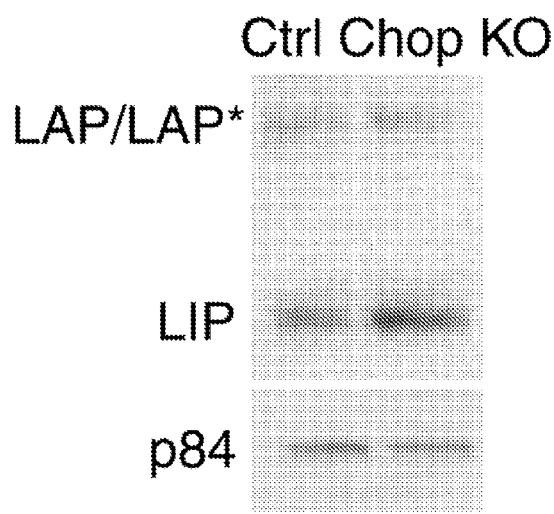

The function of LIP, LAP, and LAP* was tested by DNA-binding ELISA using antibodies against all C/EBPβ isoforms (C-19) or specific for LAP/LAP* (3087). LIP activity could not be directly measured, as no specific antibodies are currently available. A similar activity using the C-19 antibody, but a lower DNA binding by LAP/LAP*, were found in Chop KO MDSC, as compared to controls (FIG. 9A). The low activity of LAP/LAP* found in Chop KO MDSC correlated with a higher LIP expression, but no changes in LAP/LAP* (FIG. 9B), suggesting the role of LIP in the regulation of LAP/LAP* in Chop KO MDSC.

Example 10

Targeting Chop in Tumors Using a Liposomal-Encapsulated siRNA

The therapeutic targeting of Chop in tumors is limited by the absence of a specific inhibitor. As an alternative approach, the effect was tested of a novel therapy in which specific siRNAs are encapsulated into pegylated-liposomes (PEG-liposomes) and injected into tumor-bearing hosts as a means to block specific gene expression. Initial studies determined the siRNA sequence having the highest ability to block Chop expression in cells treated with the stress inducer agent tunicamycin.

Figure 10A:
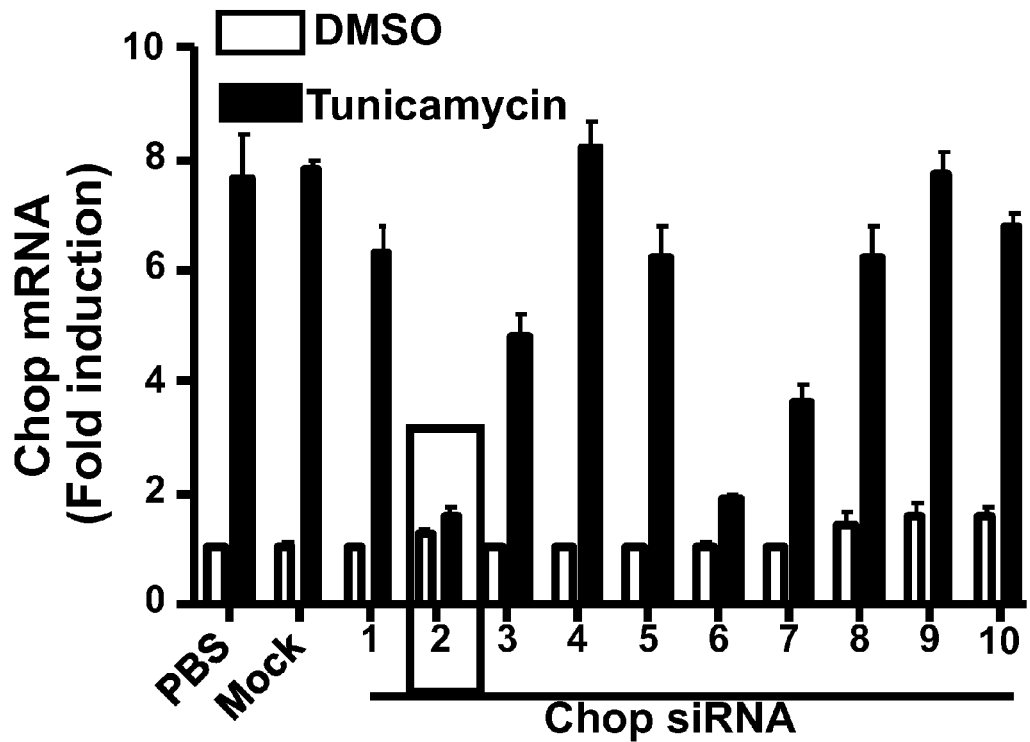
FIGS. 10A-10C illustrate that a liposomal encapsulated siRNA blocked Chop in tumors.

Using a panel of 10 different 21-nucleotide siRNA duplexes (as presented in Table 1), siRNA#2 (CCAACA-GAGGUCACACGCAdTdT (SEQ ID NO: 1) was identified as the most advantageous sequence to silence Chop expression (FIG. 10A).

TABLE 1

| siRNA | First strand (5'-3') | Second strand (5'-3') |
|---|---|---|
| 1 | GGAAGAACUAGGAAA CGGAdTdT (SEQ ID NO: 10) | UCCGUUUCCUAGUUC UUCCdTdT (SEQ ID NO: 11) |
| 2 | CCAACAGAGGUCACA CGCAdTdT (SEQ ID NO: 1) | UGCGUGUGACCUCUG UUGGdTdT (SEQ ID NO: 12) |
| 3 | GUCAGAGUUCUAUGG CCCAdTdT (SEQ ID NO: 13) | UGGGCCAUAGAACUC UGACdTdT (SEQ ID NO: 14) |
| 4 | CGGAAAGUGGCACAG CUAGdTdT (SEQ ID NO: 15) | CUAGCUGUGCCACUU UCCGdTdT (SEQ ID NO: 16) |
| 5 | GAAGAACUAGGAAAC GGAAdTdT (SEQ ID NO: 17) | UUCCGUUUCCUAGUU CUUCdTdT (SEQ ID NO: 18) |
| 6 | GUCCCUAGCUUGGCU GACAdTdT (SEQ ID NO: 19) | UGUCAGCCAAGCUAG GGACdTdT (SEQ ID NO: 20) |
| 7 | GUCACACGCACAUCC CAAAdTdT (SEQ ID NO: 21) | UUUGGGAUGUGCGUG UGACdTdT (SEQ ID NO: 22) |

TABLE 1-continued

| siRNA | First strand (5'-3') | Second strand (5'-3') |
|---|---|---|
| 8 | CUCUCCAGAUUCCAG UCAGdTdT (SEQ ID NO: 23) | CUGACUGGAAUCUGG AGAGdTdT (SEQ ID NO: 24) |
| 9 | GAGCAAGGAAGAACU AGGAdTdT (SEQ ID NO: 25) | UCCUAGUUCUUCCUU GCUCdTdT (SEQ ID NO: 26) |
| 10 | CAACAGAGGUCACAC GCACdTdT (SEQ ID NO: 27) | GUGCGUGUGACCUCU GUUGdTdT (SEQ ID NO: 28) |

Figure 10B:
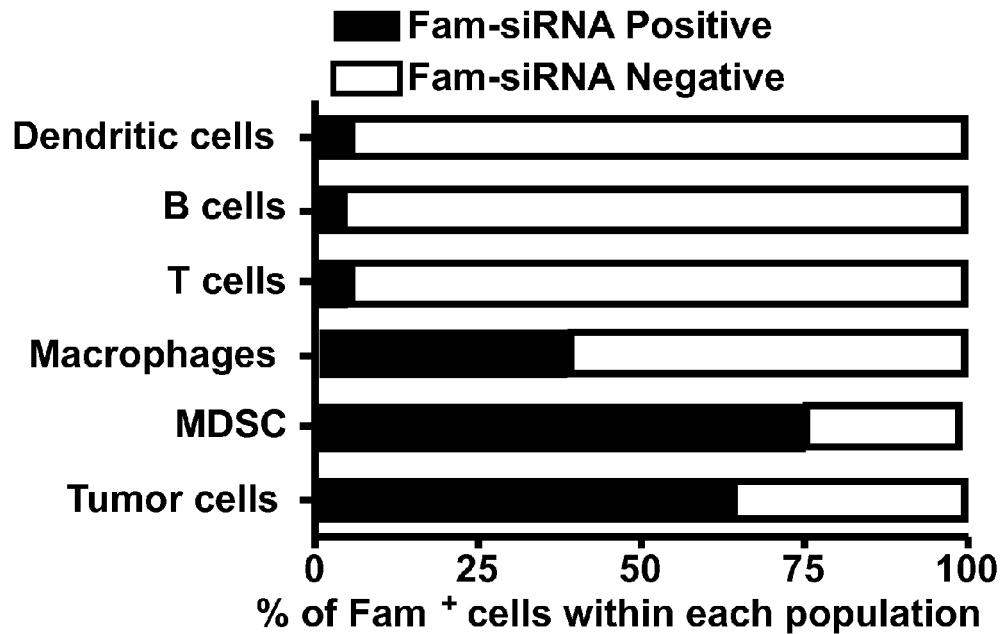

The ability of PEG-liposomes-siRNA to reach MDSC in tumors was examined. Thus, PEG-liposomes Fam-labeled mock siRNA (5 mg/kg, Altogen) were injected into mice and 3 days later, the distribution of Fam-siRNA was measured in tumor suspensions by flow cytometry. Fam-siRNA was more efficiently incorporated within MDSC (76% of all MDSC were positive for FAM), tumor cells (64%), and macrophages (39%), as compared to T cells (6%), B cells (4%), and dendritic cells (5%) (FIG. 10B). Accordingly, this therapy targeted the major populations of cells expressing Chop in tumors.

Figure 10C:
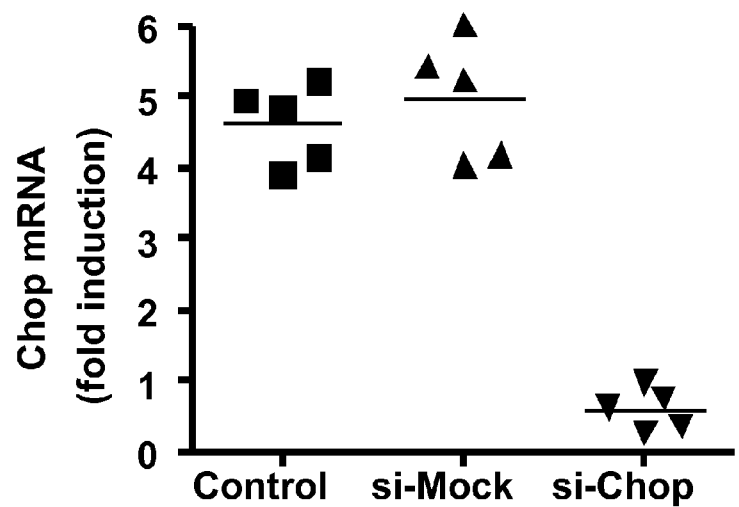
Figure 10D:
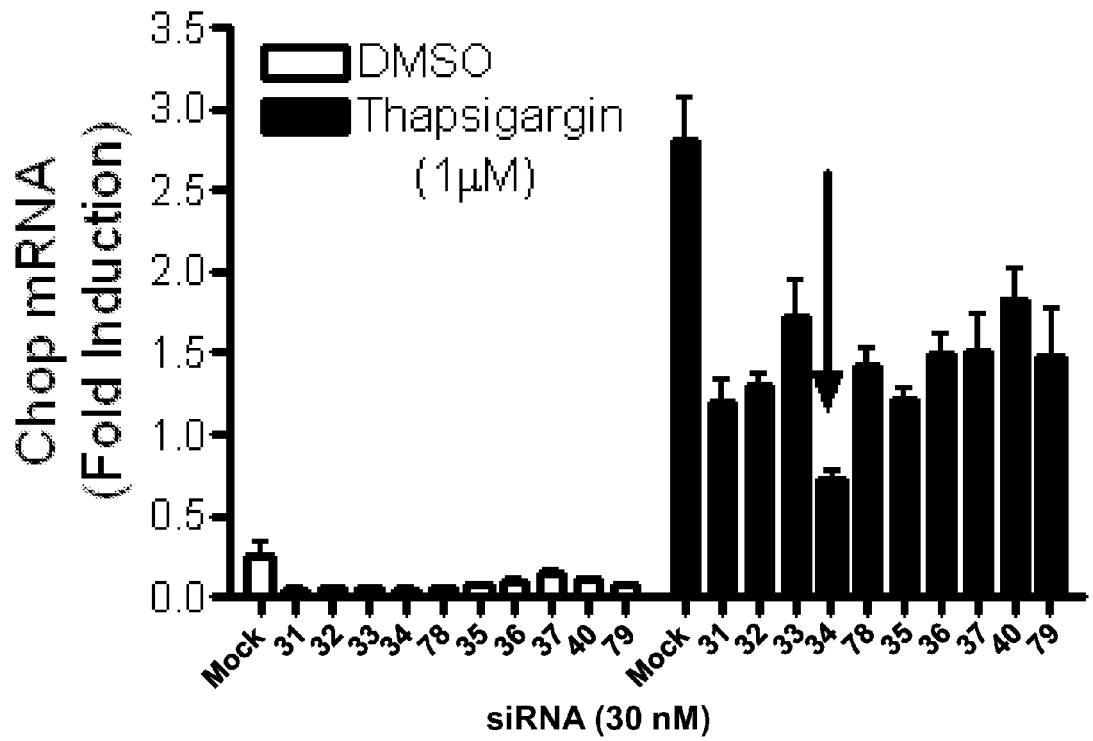
FIGS. 10D and 10E illustrate that when cells were treated with thapsigargin there was induction of Chop expression that was decreased by transfection with anti-Chop siRNA (duplex with SEQ ID NO: 1) (FIG. 10D). Chop mRNA and protein were decreased as measured by q PCR and western blot analysis (FIG. 10E).
Figure 10E:
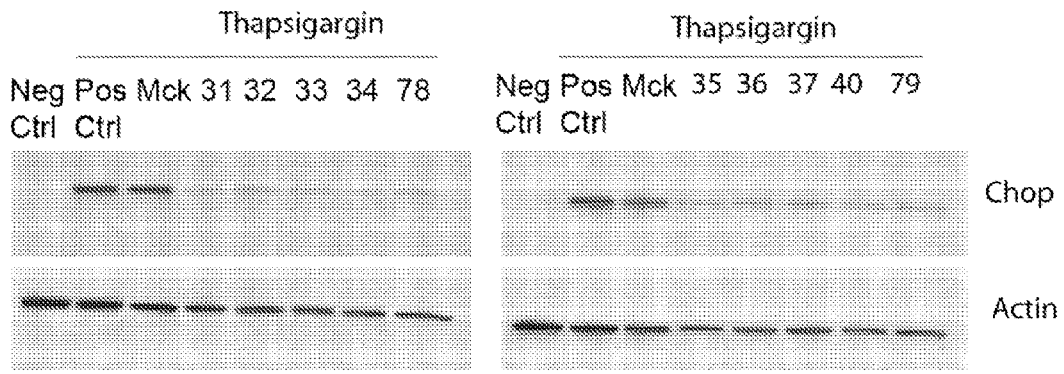
Figure 10F:
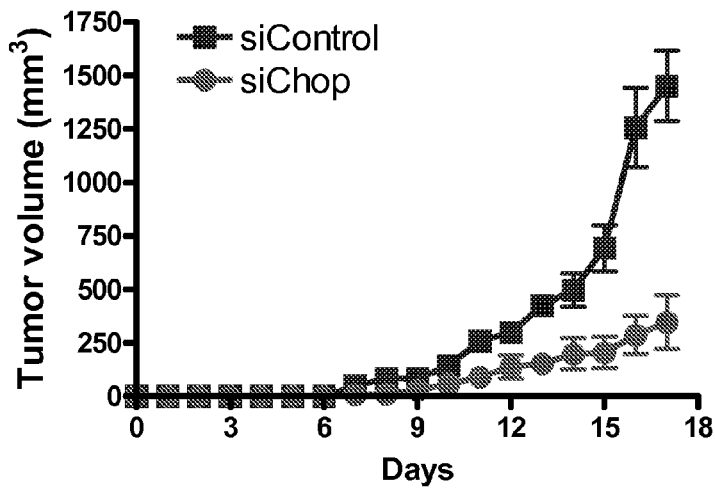
FIG. 10F illustrates 3LL-bearing mice treated with anti-Chop siRNA (every other day) resulting in a reduction in tumor volume. (5 mice per group).
Figure 10G:
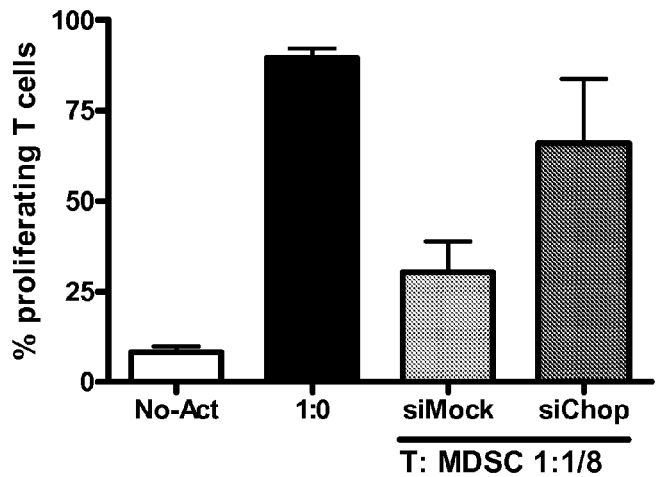
FIG. 10G illustrates MDSC treated with anti-Chop siRNA tested for their ability to block T cell proliferation.
Figure 11:
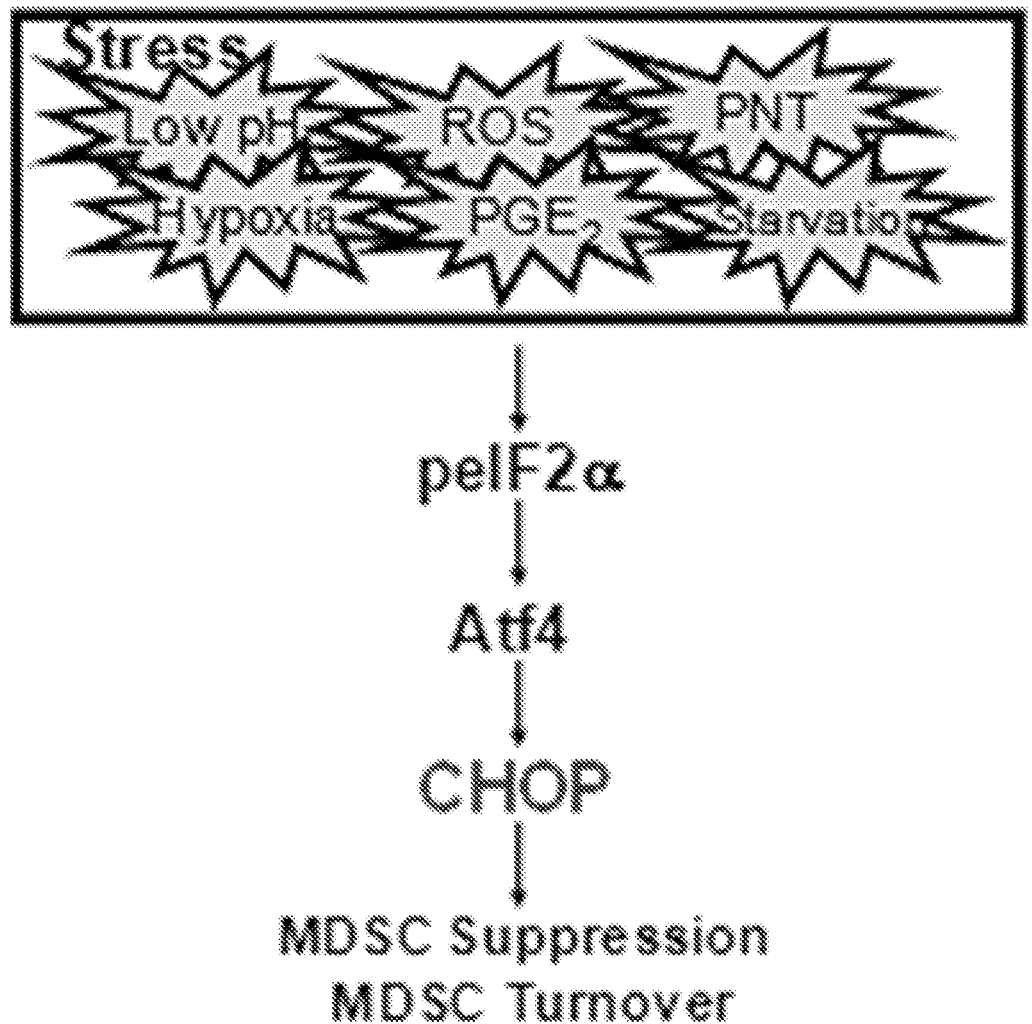
FIG. 11 schematically illustrates a pathway responsible for Chop induction in MDSC.

Whether injection of PEG-liposomes Chop siRNA #2 (5 mg/kg) modulated the expression of Chop in tumors was examined. Mice bearing tumors for 14 days received a single dose of anti-Chop or mock siRNA (5 mg/kg) and 3 days later, the tumors were tested for the expression of Chop. A significant down-regulation in the expression of Chop was found in mice treated with Chop siRNA, as compared to those receiving mock control (FIG. 10C). This indicates the potential therapeutic effect of this approach as a way to silence Chop in tumors.

Example 11

Animals, Cell Lines, and Reagents

C57BL/6 mice (6 to 8-wk-old female) were obtained from Harlan (Indianapolis, Ind.). OT-1, Ddit3$^{-/-}$, CD45.1, Gp91$^{Phox-/-}$, and Atf4$^{+/-}$ mice were purchased from the Jackson Laboratories (Bar Harbor, Me.). 3LL Lewis lung carcinoma, B16 melanoma, MCA-38 colon carcinoma, and EL-4 thymoma cells (American Type Culture Collection, Manassas, Va.) were injected into the mice, as we described (Raber et al., 2013). Ovalbumin or IL-6-expressing 3LL cells (3LL-OVA, or 3LL-IL-6) were generated by transfection using Lipofectamine 2000 (Life Technologies) with vectors coding for cytosolic chicken ovalbumin (Yang et al., 2010) or IL-6 (Manderson et al., 2007), and harboring a neomycin resistance cassette (Addgene). 3LL clones were selected in medium supplemented with 500 µg/ml Geneticin. Bone marrow-derived MDSCs (BM-MDSCs) were generated by culturing BM cells for 3 days in the presence of G-CSF (100 ng/mL) and GM-CSF (20 ng/mL).

For MDSCs depletion experiments, depleting antibody to Gr-1 (clone RB6-8C5, BioXcell) was administered i.p. 200 µg/dose on day 0 and every fourth day until tumor endpoint. For CD4$^+$ or CD8$^+$ T cell depletion studies, mice were pre-treated 24 hours before tumor injection with 400 µg anti-CD4 (clone GK1.5) or anti-CD8 (clone 53.6.72). Maintenance doses of the depleting antibodies were given twice a week. Cytotoxic effects of tumor MDSCs on 3LL cells in vitro were determined by non-radioactive cytotoxicity assay using LDH (Promega, Madison, Wis.). L-NAC (1 mg/kg/day) was injected i.p. starting at day 1 post-tumor injection. Tumor volume was measured using calipers and calculated using the formula [(small diameter)$^2$×(large diameter)×0.5].

Example 12

Antibodies

Purified antibodies against arginase I (clone 19) and iNOS (54/iNOS), fluorochrome conjugated antibodies against CD3 (G-3), CD8 (53-6.7), CD25 (PC61), Foxp3 (MF23), CD49f (GoH3), CD45.1 (A20), Gr-1 (RB6-8C5), CD11b (M1/70), CD11b (ICRF44), CD45.2 (104), Ly6G (1A8), Ly6C (AL-21), IFNγ (XMG1.2), MHCI (KH95), MHCII (AF6-120.1), CD11c (HL3), and 5-bromo-2-deoxyuridine (BrdU) labeling kit were obtained from Becton Dickinson Biosciences (BD Biosciences, San Jose, Calif.). Anti-β-actin antibody (AC-74) was obtained from Sigma-Aldrich (St. Louis, Mo.). Anti-C/EBPβ (C-19) and Chop (R-20) were obtained from Santa Cruz Biotechnology (Dallas, Tex.). Anti-eIF2α (eIF2α) was obtained from Life Technologies. Antibodies against peIF2α (E90), and p84 (5E10) were purchased from Abcam (Cambridge, Mass.). Antibodies against cleaved caspase 3 (5A1E), caspase 3 (8G10), p-STAT3 (3E2), STAT3 (124h6), and Atf4 (D4B8) were obtained from Cell Signaling (Beverly, Mass.). Anti-Chop (9C8) was obtained from Thermo Scientific. Antibodies against CD126 (D7715A7), CD130 (KPG130), IL-6 (MP5-20F3), CD33 (WM-53), HLA-DR (L243) were obtained from ebioscience, while anti-F4/80 (BM8) was purchased from Biolegend (San Diego, Calif.).

Example 13

Bone Marrow Chimeras

Recipient mice lethally irradiated with 950 rads (2 rounds of 475 rads during the same day) were reconstituted with 1×10$^7$ bone marrow cells and 1×10$^6$ splenocytes from donor mice. Chimeric engraftment was verified in peripheral blood 7 weeks after transplantation by monitoring the corresponding switch from CD45.1$^+$ cells into CD45.2$^+$ or from CD45.2$^+$ into CD45.1$^+$ using flow cytometry. A week later, mice were injected s.c. with 3LL tumor cells and tumor growth kinetics and MDSCs suppressive activity evaluated.

Example 14

Tolerogenic Effect of MDSCs

To determine the effect of Chop in the tolerogenic activity of MDSCs in vivo, a model previously described Dolcetti et al., ((2010) Curr. Protoc. Immunol. 14, Unit, 14.17) was used. Briefly, CD8$^+$ T cells (5×10$^6$) from CD45.2$^+$ OT-1 mice were adoptively transferred via tail vein into CD45.1$^+$ mice. Two days later MDSCs were sorted from 3LL tumor-bearing wild-type or Ddit3$^{-/-}$ mice, pulsed with 2 µg/mL SIINFEKL for 1 h, and 5×10$^6$ MDSCs transferred i.v. into the mice previously injected with OT-1. The same day, mice received s.c. vaccination with 4×10$^6$ DCs generated from bone marrow cells cultured in medium containing GM-CSF (20 ng/mL) and IL-4 (10 ng/mL) for 6 days. During the final 24 hours of culture, DCs were exposed to 2 µg/mL SIIN-FEKL and 1 µg/mL LPS. Mice received a second injection with SIINFEKL-pulsed MDSCs 5 days later. Twelve days after the initial DCs immunization, draining lymph nodes were recovered and challenged with SIINFEKL for 24 h, after which they were monitored for IFNγ production by Elispot (R & D systems).

Example 15

Adoptive Cellular Therapy

For T cell immunotherapy experiments, CD45.2$^+$ wild-type or Ddit3$^{-/-}$ mice were injected with 3LL-OVA cells (1×10$^6$) at day 0 or at stratified time points to achieve tumor of similar palpable volume. Mice then received adoptive transfer of 5×10$^6$ CD45.1$^+$ CD8$^+$ OT-1 cells via tail vein injection. The following day, mice were vaccinated s.c. with 100 µg of SIINFEKL peptide in 0.2 mL of PBS. Ten days later spleens and tumors were tested for transferred OT-1 cells and function.

Example 16

Chromatin Immunoprecipitation

ChIP assays were performed using SimpleChip kits (Cell Signaling). Chromatin was prepared from 4×10$^6$ cells MDSCs positively selected from tumor and spleens of wild-type and Ddit3$^{-/-}$ bearing 3LL tumors or splenic iMCs from control mice. Chromatin was immunoprecipitated with antibodies against Atf4, C/EBPβ, Histone H3, or rabbit IgG. Eluted and purified DNA was analyzed by qPCR with pre-validated primers against the Chop promoter (Atf4), IL-6 promoter (C/EBPβ) and Arginase I promoter (C/EBPβ) purchased from Qiagen.

Example 17

Sorting of Cells

Tumors were digested with DNAse and Liberase (Roche USA, Branchburg, N.J.). Tumor digest were then used to isolated different tumor populations by flow cytometry. 3LL tumor cells were recovered by sorting CD49f$^+$ CD45$^-$ cells. Tumor leukocytes were gated as CD49f$^-$ CD45$^+$, and sub-divided into the following: CD11b$^+$ Gr1$^+$, CD11b$^+$ Gr1$^-$, CD11b$^+$ CD11c$^+$, CD11b$^+$ F4/80$^+$, B220$^+$, and CD3$^+$. For functional assays, MDSCs were isolated as described (Rodriguez et al., 2005). Purity for each population ranged from 90%-99%, as measured by flow cytometry. In MDSCs co-injection experiments, 1×10$^6$ tumor-derived MDSCs were injected with 1×10$^6$ 3 LL cells s.c. For MDSCs adoptive transfer experiments, 3LL tumor-bearing control mice received control or Ddit3$^{-/-}$ tumor MDSCs (3×10$^6$ i.v.) on days 3 and 6 after tumor injection.

Example 18

BM-MDSCs Models

Bone marrow-derived MDSCs (BM-MDSCs) were generated by culturing BM cells for 3 days in the presence of G-CSF (100 ng/mL) and GM-CSF (20 ng/mL). BM-MDSCs were exposed to tumor derived stress factors by the addition of 40% 3LL tumor explants supernatant (TES) for 24 hours on day 3 of the BM-MDSCs protocol. TES was produced by from 3LL tumors digested at 17 days after injection. Digested tumors were depleted of red blood cells, plated at a 1×10$^7$ tumor cells/mL and cultured overnight. Supernatants were removed, centrifuged to remove non-adherent cells, syringe filtered to remove cell debris, and stored at −80 C until use. L-NAC (2 mM), MnTBAP (100 µM), or PTIO (100 µM) were added to BM-MDSCs cultures on day 3.

Example 19

T Cell Proliferation

T cell proliferation was measured using Carboxyfluorescein succinimidyl ester (CFSE) (Life Technologies), as described (Raber et al., 2013). Data is expressed as the percentage of T cells proliferating as tested by the dilution of CFSE fluorescence compared with non-activated T cells.

Example 20

Western Blot and ELISA

Cell lysates were electrophoresed in TrisGlycine gels, transferred to PVDF membranes, and immunoblotted with antibodies against peIF2α, eIF2α, Chop, C/EBPβ, arginase I, p84, p-STAT3, STAT3, and β-actin diluted at (all 1:500). Membrane-bound immune complexes were detected using ECL detection reagent (GE Healthcare). ELISA for nitrosylated protein (Millipore), and IL-6 (eBioscience) were performed on lysates from sorted MDSCs. Densitometry of C/EBPβ isoforms normalized to nuclear p84 was calculated using NIH Image J.

Example 21

IL-6 Production in MDSCs

For analysis of IL-6 production in MDSCs, tumor-bearing mice were injected i.p. with 0.25 mg of Brefeldin A for 6 hours, after which tumors were isolated and MDSCs tested for IL-6 by flow cytometry. To assess integrity of the IL-6 signaling pathway in MDSCs, BM-MDSCs were developed using BM cells from wild-type, and Ddit3$^{-/-}$ mice. On protocol day 3, mouse recombinant IL-6 (R&D Systems) was supplemented to the culture at 50 ng/mL for 8 hours.

Example 22

MDSCs Suppressive Mechanism Assays

Superoxide production was quantified in freshly isolated MDSCs using the Superoxide Anion Assay Kit (Sigma). Peroxynitrite levels were determined in tissue or MDSCs lysates using a Nitrotyrosine ELISA Assay (EMD Millipore).

Example 23

C/EBPβ Activity

Nuclear extracts from MDSCs were tested for C/EBPβ DNA binding activity using the TransAM C/EBPβ DNA-binding ELISA kit (Active Motif, Carlsbad, Calif.).

Example 24

Antigen Presentation Assay

Exogenous presentation of antigen was determined using tumor MDSCs sorted from tumor-bearing control or Ddit3$^{-/-}$ mice. MDSCs were pulsed with SIINFEKL peptide (2 µg/mL for 3 hours), washed twice with PBS, then plated with naïve CFSE labeled OT-1 cells at decreasing dilutions (1:1/2-1:1/16, OT-1:MDSCs). OT-1 cell proliferation was evaluated after 72 hours of co-culture.

Example 25

Quantitative PCR

Total RNA was isolated from tumor-derived MDSCs using TRIzol (Invitrogen, Life Technologies). RNA was then converted to cDNA using a Bio-Rad iScript cDNA synthesis kit (Bio-Rad, Hercules, Calif.). Quantitative PCR was performed on an Applied Biosystems thermocycler (7900 HT) using Bio-Rad SYBR green supermix with primers against murine Chop forward (GGAGCTGGAAGCCTGGTATG (SEQ ID NO: 2)), reverse (GGATGTGCGTGTGACCTCTG (SEQ ID NO: 3)), Atf4 forward (GCCTGACTCTGCTGCTTACA (SEQ ID NO: 4)) reverse (CTTGCCTTACGGACCTCTTC (SEQ ID NO: 5)), and C/EBPβ forward (GACAAGCTGAGCGACGAGTA (SEQ ID NO: 6)) reverse (AGCTGCTCCACCTTCTTCTG (SEQ ID NO: 7)). Relative expression was calculated using the delta-delta Ct method and normalized to the reference gene Actb forward (TGTGATGGTGGGAATGGGTCAGAA (SEQ ID NO: 8)) reverse (TGTGGTGCCAGATCTTCTCCATGT (SEQ ID NO: 9)). For miRNA experiments, total RNA was isolated using TRIzol and converted to cDNA using miScript II RT Kit (Qiagen). Quantitative PCR was performed using miScript SYBR Green PCR Kit using primers against miR-142-3p and RNU6-2 (Qiagen).

Example 26

Statistical Analysis

Statistical analyses were carried in SAS 9.3 (SAS Institute, Cary, N.C.). Tests were conducted at 5% significance level. Continuous data were checked for unequal variances with the Brown-Forsythe and Levene tests. Percentage data were arcsine transformed and further checked for unequal variances. Experimental groups differences of endpoints were assessed by ANOVA with the Satterthwaite correction for unequal variances using the MIXED procedure. Means comparisons were carried out with the Tukey procedure for all comparisons or with the Dunnet procedure for comparisons with the control group.

---

What is claimed:

1. A method of reducing the level of activity of C/EBP-homologous protein (Chop) in a myeloid-derived suppressor cell (MDSC) or population of said cells, said method comprising delivering to a recipient MDSC or population of said recipient cells a composition comprising an siRNA, wherein the siRNA is an isolated double-stranded ribonucleic acid (dsRNA) molecule having either no overhang regions or at least one overhang region, wherein each overhang region contains six or fewer nucleotides, and wherein the dsRNA inhibits expression by a cell of a Chop protein, and wherein a first strand of the dsRNA is substantially identical to the sequence according to SEQ ID NO: 1, and a second strand is substantially complementary to the first that reduces the activity of Chop in the cell(s), and a vehicle for delivery of the agent to the interior of the recipient cell.

2. The method of claim 1, wherein the agent is an siRNA and results in gene silencing of the Chop gene in the recipient MDSC or population of MDSCs.

3. The method of claim 1, wherein the first strand of the dsRNA has a nucleotide sequence comprising SEQ ID NO: 1.

4. The method of claim 1, wherein the vehicle is a liposome.

5. The method of claim 1, wherein the vehicle is a pegylated-liposome.

6. The method of claim 1, wherein the composition further comprises a pharmaceutically acceptable carrier.

7. The method of claim 1, wherein the recipient MDSC or population of said recipient cells are isolated from an animal or human subject.

8. The method of claim 7, wherein the isolated MDSC or population of said recipient cells are cultured cells.

9. A composition comprising an siRNA agent that when delivered to a myeloid-derived suppressor cell (MDSC) or population of said cells reduces the level of expression of a Chop-encoding gene, thereby reducing the level of Chop in the cell or cells, wherein the siRNA is an isolated double-stranded ribonucleic acid (dsRNA) molecule having either no overhang regions or at least one overhang region, wherein each overhang region contains six or fewer nucleotides, and wherein the dsRNA inhibits expression by a cell of a Chop protein, and wherein a first strand of the dsRNA is substantially identical to the sequence according to SEQ ID NO: 1, and a second strand is substantially complementary to the first.

10. The composition of claim 9, further comprising a vehicle suitable for the delivery of the agent to the interior of the cell or cells.

11. The composition of claim 10, wherein the vehicle is a liposome.

12. The composition of claim 10, wherein the vehicle is a pegylated-liposome.

13. The composition of claim 9, wherein the first strand of the dsRNA has the nucleotide sequence SEQ ID NO: 1.

* * * * *